(12) United States Patent
  Sappenfield

(10) Patent No.: US 9,382,973 B2
(45) Date of Patent: Jul. 5, 2016

(54) ROTARY UNITS, ROTARY MECHANISMS, AND RELATED APPLICATIONS

(71) Applicant: Christopher C. Sappenfield, San Diego, CA (US)

(72) Inventor: Christopher C. Sappenfield, San Diego, CA (US)

( * ) Notice: Subject to any disclaimer, the term of this patent is extended or adjusted under 35 U.S.C. 154(b) by 230 days.

(21) Appl. No.: 14/327,519

(22) Filed: Jul. 9, 2014

(65) Prior Publication Data

US 2014/0323263 A1    Oct. 30, 2014

Related U.S. Application Data

(63) Continuation-in-part of application No. 14/187,302, filed on Feb. 23, 2014, now Pat. No. 8,956,258, which is a continuation of application No. 13/451,468, filed on Apr. 19, 2012, now Pat. No. 8,684,883, which is a
(Continued)

(51) Int. Cl.
  *F16H 1/46* (2006.01)
  *B23P 15/14* (2006.01)
  *F16H 37/08* (2006.01)
  *A61C 17/26* (2006.01)

(52) U.S. Cl.
  CPC . *F16H 1/46* (2013.01); *B23P 15/14* (2013.01); *F16H 37/0813* (2013.01); *A61C 17/26* (2013.01); *Y10T 29/49465* (2015.01); *Y10T 74/19642* (2015.01)

(58) Field of Classification Search
  CPC ....... B23P 15/14; F16H 1/46; F16H 37/0813; Y10T 29/49465
  See application file for complete search history.

(56) References Cited

U.S. PATENT DOCUMENTS

| 75,676 A | 3/1868 | Goodwin |
| 845,103 A | 2/1907 | Ljungstrom |
| 1,059,450 A | 4/1913 | Foote |
| 1,489,817 A | 4/1924 | Campbell |
| 1,887,429 A | 11/1932 | Price |

(Continued)

FOREIGN PATENT DOCUMENTS

| CA | 2737322 | 3/2015 |
| CN | 2619094 | 6/2004 |
| JP | 05332413 | 12/1993 |
| WO | WO0011372 | 3/2000 |
| WO | WO2010042934 | 4/2010 |

OTHER PUBLICATIONS

Notice of Allowance mailed Jan. 26, 2015 for U.S. Appl. No. 14/187,252.
(Continued)

*Primary Examiner* — Derek D Knight
(74) *Attorney, Agent, or Firm* — Christopher C. Sappenfield

(57) ABSTRACT

The invention relates to devices including rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate.

20 Claims, 34 Drawing Sheets

Related U.S. Application Data continuation-in-part of application No. 13/423,413, filed on Mar. 19, 2012, now Pat. No. 8,672,799, which is a continuation-in-part of application No. 13/219,683, filed on Aug. 28, 2011, now Pat. No. 8,715,133, which is a continuation-in-part of application No. 13/184,332, filed on Jul. 15, 2011, now Pat. No. 8,668,618, which is a continuation-in-part of application No. 12/577,326, filed on Oct. 12, 2009, now Pat. No. 8,152,679, which is a continuation of application No. PCT/US2009/060386, filed on Oct. 12, 2009.

(60) Provisional application No. 61/365,290, filed on Jul. 16, 2010, provisional application No. 61/376,725, filed on Aug. 25, 2010, provisional application No. 61/104,748, filed on Oct. 12, 2008.

(56) References Cited

U.S. PATENT DOCUMENTS

| | | | |
|---|---|---|---|
| 2,583,872 | A | 1/1952 | Newcomb |
| 2,851,905 | A | 9/1958 | Clark |
| 2,905,451 | A | 9/1959 | Callanen et al. |
| 2,950,634 | A | 8/1960 | Clark |
| 3,088,414 | A | 5/1963 | Cahit |
| 3,222,533 | A | 12/1965 | Mackay |
| 3,507,113 | A | 4/1970 | Herrmann et al. |
| 3,892,278 | A | 7/1975 | Smith et al. |
| 3,913,415 | A | 10/1975 | Herr |
| 4,044,841 | A | 8/1977 | Smith et al. |
| 4,132,131 | A | 1/1979 | DeBruyne |
| 4,159,624 | A | 7/1979 | Gruner |
| 4,334,440 | A | 6/1982 | Fonck |
| 4,365,525 | A | 12/1982 | Imazaike |
| 4,464,095 | A | 8/1984 | Iida |
| 4,535,653 | A | 8/1985 | Coburn |
| 4,611,504 | A | 9/1986 | Rundle |
| 4,627,310 | A | 12/1986 | Coburn |
| 4,683,897 | A | 8/1987 | McBride |
| 4,732,053 | A | 3/1988 | Gleasman |
| 4,763,031 | A | 8/1988 | Wang |
| 4,825,723 | A | 5/1989 | Martin |
| 4,825,727 | A | 5/1989 | Komuro |
| 4,896,567 | A | 1/1990 | Zhou et al. |
| 4,926,715 | A | 5/1990 | Hirt et al. |
| 4,964,844 | A | 10/1990 | Bagnall |
| 5,014,428 | A | 5/1991 | Yamashita |
| 5,426,806 | A | 6/1995 | Johnson et al. |
| 5,595,147 | A | 1/1997 | Feuling |
| 5,679,089 | A | 10/1997 | Levendahl |
| 5,724,867 | A | 3/1998 | Jordan |
| 5,870,790 | A | 2/1999 | Root |
| 6,032,313 | A | 3/2000 | Tsang |
| 6,170,503 | B1 | 1/2001 | Taghavi-Khanghah |
| 6,176,804 | B1 | 1/2001 | Kekki et al. |
| 6,213,224 | B1 | 4/2001 | Furuta |
| 6,222,293 | B1 | 4/2001 | Ikeda et al. |
| 6,357,118 | B1 | 3/2002 | Eichhorn et al. |
| 6,379,276 | B1 | 4/2002 | Cheng |
| 6,418,810 | B1 | 7/2002 | Kerr |
| 6,492,743 | B1 | 12/2002 | Appa |
| 6,626,792 | B2 | 9/2003 | Vranish |
| 6,669,594 | B2 | 12/2003 | Kerr |
| 6,672,538 | B2 | 1/2004 | Millea et al. |
| 6,732,603 | B1 | 5/2004 | Hsu et al. |
| 6,799,579 | B2 | 10/2004 | Joseph |
| 6,829,457 | B2 | 12/2004 | Ryuzaki et al. |
| 6,859,976 | B2 | 3/2005 | Plankenhorn |
| 7,021,851 | B1 | 4/2006 | King |
| 7,022,042 | B2 | 4/2006 | Fleytman |
| 7,063,173 | B2 | 6/2006 | Herla |
| 7,108,629 | B2 | 9/2006 | Hiraiwa |
| 7,118,340 | B2 | 10/2006 | D'Anna |
| 7,153,004 | B2 | 12/2006 | Galli |
| 7,181,799 | B2 | 2/2007 | Gavney |
| 7,182,708 | B2 | 2/2007 | Winzeler |
| 7,296,495 | B2 | 11/2007 | Quinn |
| 7,413,025 | B2 | 8/2008 | Provost |
| 7,555,363 | B2 | 6/2009 | Augenbraun et al. |
| 7,784,731 | B2 | 8/2010 | Lin |
| 7,967,740 | B2 | 6/2011 | Mertens |
| 7,993,067 | B2 | 8/2011 | Hall et al. |
| 8,042,217 | B2 | 10/2011 | Sorrentino |
| 8,046,861 | B2 | 11/2011 | Joseph |
| 8,056,175 | B2 | 11/2011 | Kunita et al. |
| 8,087,843 | B2 | 1/2012 | Ottaviani et al. |
| 8,152,679 | B2 | 4/2012 | Sappenfield |
| 8,250,694 | B2 | 8/2012 | Gatzemeyer |
| 8,264,096 | B2 | 9/2012 | Micu |
| 8,276,231 | B2 | 10/2012 | Gavney |
| 8,277,358 | B2 | 10/2012 | Gasparrini |
| 8,302,238 | B2 | 11/2012 | Biro |
| 8,316,496 | B2 | 11/2012 | Al-Qaffas |
| 8,358,029 | B2 | 1/2013 | Burkart |
| 8,662,781 | B2 | 3/2014 | Sappenfield |
| 8,668,618 | B2 | 3/2014 | Sappenfield |
| 8,668,619 | B2 | 3/2014 | Sappenfield |
| 8,672,798 | B2 | 3/2014 | Sappenfield |
| 8,672,799 | B2 | 3/2014 | Sappenfield |
| 8,684,883 | B2 | 4/2014 | Sappenfield |
| 8,715,133 | B2 | 5/2014 | Sappenfield |
| 8,742,608 | B2 | 6/2014 | Micu |
| 8,814,505 | B2 | 8/2014 | Bellis |
| 8,834,315 | B2 | 9/2014 | Sappenfield |
| 8,956,258 | B2 | 2/2015 | Sappenfield |
| 8,979,703 | B2 | 3/2015 | Sappenfield |
| 9,057,325 | B2 | 6/2015 | Sappenfield |
| 2003/0113133 | A1 | 6/2003 | Ryuzaki |
| 2003/0220169 | A1* | 11/2003 | Norman ............ B25J 9/102 475/331 |
| 2006/0103246 | A1 | 5/2006 | Umeda et al. |
| 2007/0020020 | A1 | 1/2007 | Bobrosky et al. |
| 2007/0249460 | A1 | 10/2007 | Schulz et al. |
| 2008/0070739 | A1 | 3/2008 | Nakamura et al. |
| 2008/0134513 | A1 | 6/2008 | Oh |
| 2008/0205970 | A1 | 8/2008 | LaFlamme et al. |
| 2008/0233815 | A1 | 9/2008 | Nakamura et al. |
| 2009/0136285 | A1 | 5/2009 | Hall et al. |
| 2010/0041504 | A1 | 2/2010 | Palmer |
| 2010/0089200 | A1* | 4/2010 | Sappenfield ........ F16H 37/0813 74/665 Q |
| 2010/0175214 | A1 | 7/2010 | Payet |
| 2010/0272500 | A1 | 10/2010 | Martin et al. |
| 2011/0232013 | A1 | 9/2011 | Sappenfield |
| 2011/0290052 | A1* | 12/2011 | Sappenfield ............ A46B 13/02 74/413 |
| 2011/0308351 | A1* | 12/2011 | Sappenfield ........ F16H 37/0813 74/665 F |
| 2012/0010039 | A1* | 1/2012 | Sappenfield ........ F16H 37/0806 475/331 |
| 2012/0010040 | A1* | 1/2012 | Sappenfield ........ F16H 37/0806 475/331 |
| 2012/0180586 | A1* | 7/2012 | Sappenfield ............ A61C 17/26 74/412 R |
| 2012/0196719 | A1 | 8/2012 | Sappenfield |
| 2012/0202641 | A1* | 8/2012 | Sappenfield ............ A61C 17/26 475/337 |
| 2013/0214627 | A1* | 8/2013 | Sappenfield ............ H02K 7/116 310/83 |
| 2014/0066246 | A1* | 3/2014 | Sappenfield ........ F16H 37/0813 475/149 |
| 2014/0166701 | A1* | 6/2014 | Sappenfield ............ A61C 17/26 222/323 |
| 2015/0369174 | A1* | 12/2015 | Sappenfield ........ F16H 37/0813 60/39.162 |

OTHER PUBLICATIONS

Notice of Allowance mailed Jan. 13, 2015 for CN Application No. 200980152835.6.
European Examination Report mailed on Apr. 9, 2015 for Application No. EP2009820037.1 filed Dec. 5, 2011.
Notice of Allowance mailed Mar. 30, 2015 for U.S. Appl. No. 14/341,804.

(56) References Cited

OTHER PUBLICATIONS

Office Action mailed Jun. 18, 2015 for U.S. Appl. No. 14/176,119, filed Feb. 2, 2014.
U.S. Appl. No. 14/740,115.
Office Action mailed Jun. 17, 2015, for U.S. Appl. No. 14/302,408, filed Jun. 6, 2014.
U.S. Appl. No. 62/186,229.
Office Action mailed Apr. 16, 2015 for U.S. Appl. No. 13/832,520, filed Mar. 15, 2013.
U.S. Appl. No. 62/197,092.
Final Office Action mailed Sep. 2, 2015 for U.S. Appl. No. 13/832,520, filed Mar. 15, 2013.
Notice of Allowance mailed Nov. 24, 2014 for U.S. Appl. No. 14/187,302.
Office Action mailed Nov. 20, 2014 for U.S. Appl. No. 14/187,252, filed Feb. 22, 2014.
U.S. Appl. No. 61/104,748.
U.S. Appl. No. 61/365,290.
U.S. Appl. No. 61/376,725.
U.S. Appl. No. 61/640,530.
Notice of Abandonment mailed Mar. 14, 2014 for U.S. Appl. No. 13/442,850.
Examiner Interview Summary mailed Dec. 30, 2011 for U.S. Appl. No. 12/577,326.
Notice of Allowance mailed Feb. 24, 2012 for U.S. Appl. No. 12/577,326.
Office Action mailed Jun. 7, 2012 for Canadian Patent Application No. 2,740,358 filed Oct. 12, 2009.
European Search Opinion and Supplementary European Search Report for Application No. EP2009820037.1, mailed on Aug. 14, 2012.
U.S. Appl. No. 61/646,348.
International Search Report for International (PCT) Patent Application No. PCT/US2009/060386, mailed Nov. 25, 2009.
Written Opinion for International (PCT) Patent Application No. PCT/US2009/060386, mailed Nov. 25, 2009.
International Preliminary Report on Patentability for International (PCT) Patent Application No. PCT/US2009/060386, mailed Apr. 21, 2011.
Office Action mailed Nov. 21, 2011 for U.S. Appl. No. 12/577,326.
Notice of Abandonment mailed Dec. 10, 2013 for Canadian Patent Application No. 2,740,358 filed Oct. 12, 2009.
Co-pending U.S. Appl. No. 14/187,252, filed Feb. 22, 2014.
Co-pending U.S. Appl. No. 14/302,408, filed Jun. 11, 2014.
Co-pending U.S. Appl. No. 14/339,382, filed Jul. 23, 2014.
Co-pending U.S. Appl. No. 14/341,804, flied Jul. 26, 2014.
Co-pending U.S. Appl. No. 14/187,302, filed Feb. 23, 2014.
Further Processing Decision for Application No. EP2009820037.1, mailed on Jul. 16, 2013.
Office Action mailed Jul. 12, 2013 for U.S. Appl. No. 13/219,683, filed Aug. 28, 2011.
Office Action mailed Nov. 12, 2013 for U.S. Appl. No. 13/219,683, filed Aug. 28, 2011.
Office Action mailed Jul. 8, 2013 for U.S. Appl. No. 13/184,332, filed Jul. 15, 2011.
Office Action mailed Oct. 18, 2013 for U.S. Appl. No. 13/184,332, filed Jul. 15, 2011.
Office Action mailed Aug. 14, 2013 for U.S. Appl. No. 13/423,413, filed Mar. 19, 2012.
Office Action mailed Oct. 18, 2013 for U.S. Appl. No. 13/218,145, filed Aug. 25, 2011.
Office Action mailed Jul. 1, 2013 for U.S. Appl. No. 13/218,145, filed Aug. 25, 2011.
Office Action mailed Sep. 4, 2013 for Chinese Patent Application No. 200980152835.6 filed Oct. 12, 2009.
Examiner Interview Summary mailed Dec. 16, 2013 for U.S. Appl. No. 13/221,890.
Office Action mailed Apr. 17, 2013 for U.S. Appl. No. 13/442,850, filed Apr. 9, 2012.
Office Action mailed Sep. 9, 2013 for U.S. Appl. No. 13/442,850, filed Apr. 9, 2012.
Office Action mailed Jan. 30, 2013 for Canadian Patent Application No. 2,737,322 filed Apr. 14, 2011.
Office Action mailed Oct. 3, 2013 for Canadian Patent Application No. 2,737,322 filed Apr. 14, 2011.
Office Action mailed May 6, 2013 for U.S. Appl. No. 13/221,890, filed Aug. 30, 2011.
Office Action mailed Aug. 22, 2013 for U.S. Appl. No. 13/221,890, filed Aug. 30, 2011.
Office Action mailed Jul. 22, 2013 for U.S. Appl. No. 13/451,468, filed Apr. 19, 2012.
Notice of Allowance mailed Jan. 31, 2014 for U.S. Appl. No. 13/451,468, filed Apr. 19, 2012.
Examiner Interview Summary mailed Jan. 8, 2014 for U.S. Appl. No. 13/219,683.
Notice of Allowance mailed Jan. 7, 2014 for U.S. Appl. No. 13/184,332, filed Jul. 15, 2011.
Notice of Allowance mailed Jan. 6, 2014 for U.S. Appl. No. 13/221,890, filed Aug. 30, 2011.
Notice of Allowance mailed Jan. 9, 2014 for U.S. Appl. No. 13/423,413, filed Mar. 19, 2012.
Notice of Allowance mailed Dec. 24, 2013 for U.S. Appl. No. 13/072,656, filed Mar. 25, 2011.
Notice of Allowance mailed Jan. 7, 2014 for U.S. Appl. No. 13/218,145, filed Aug. 25, 2011.
Office Action mailed Feb. 19, 2014 for U.S. Appl. No. 13/219,683, filed Aug. 28, 2011.
Examiner Interview Summary mailed Feb. 27, 2014 for U.S. Appl. No. 13/219,683.
Notice of Allowance mailed Mar. 4, 2014 for U.S. Appl. No. 13/219,683.
European Examination Report mailed on Feb. 27, 2014 for Application No. EP2009820037.1 filed Dec. 5, 2011.
Office Action mailed Mar. 5, 2014 for Chinese Patent Application No. 200980152835.6 filed Oct. 12, 2009.
Co-pending U.S. Appl. No. 14/176,119, filed Feb. 9, 2014.
Notice of Allowance mailed Jan. 31, 2014 for U.S. Appl. No. 13/451,468.
Office Action mailed Jun. 11, 2014 for Chinese Patent Application No. 200980152835.6 field Oct. 12, 2009.
Notice of Allowance mailed Jun. 11, 2014 for U.S. Appl. No. 13/832,575.
Notice of Allowance mailed Jun. 19, 2014 for CA Application No. 2737322.

* cited by examiner

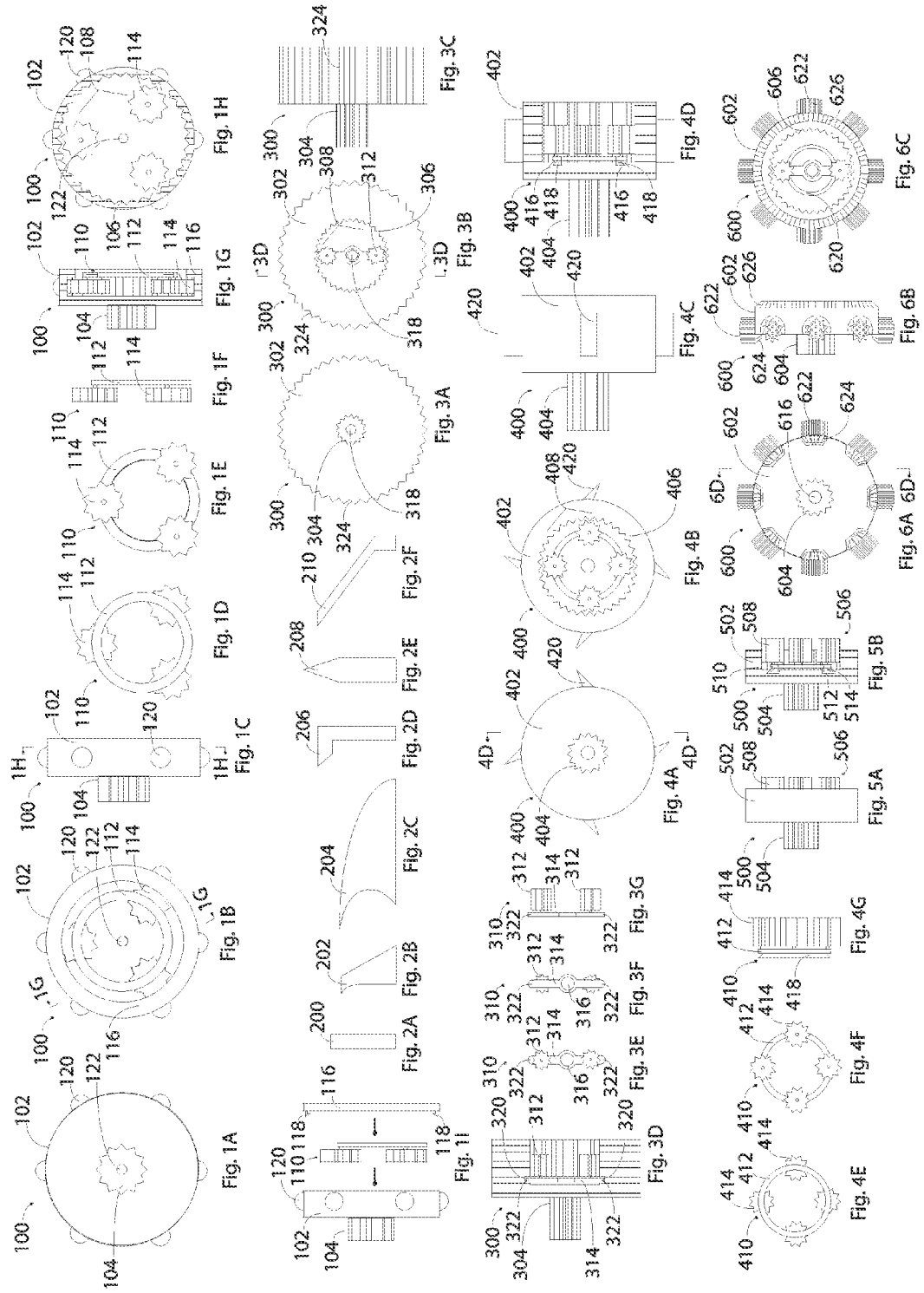

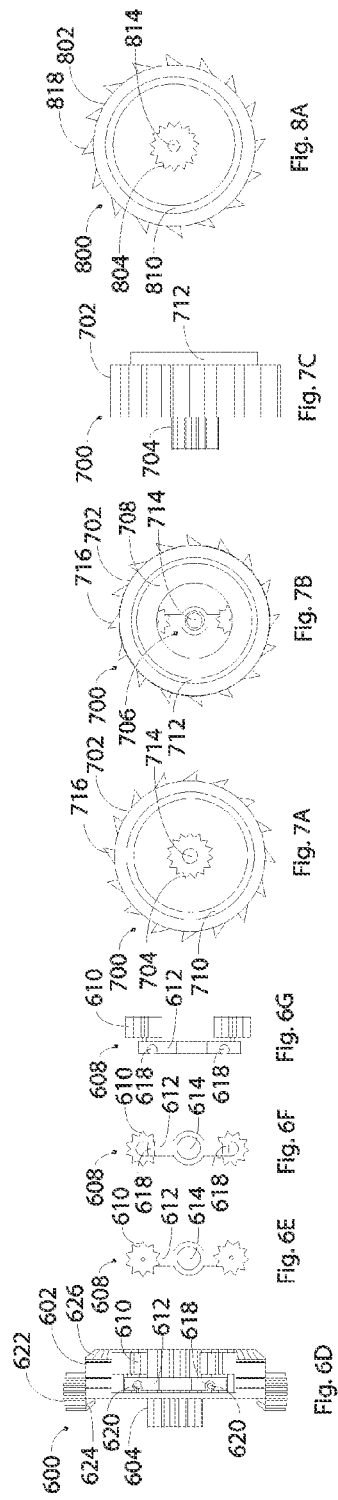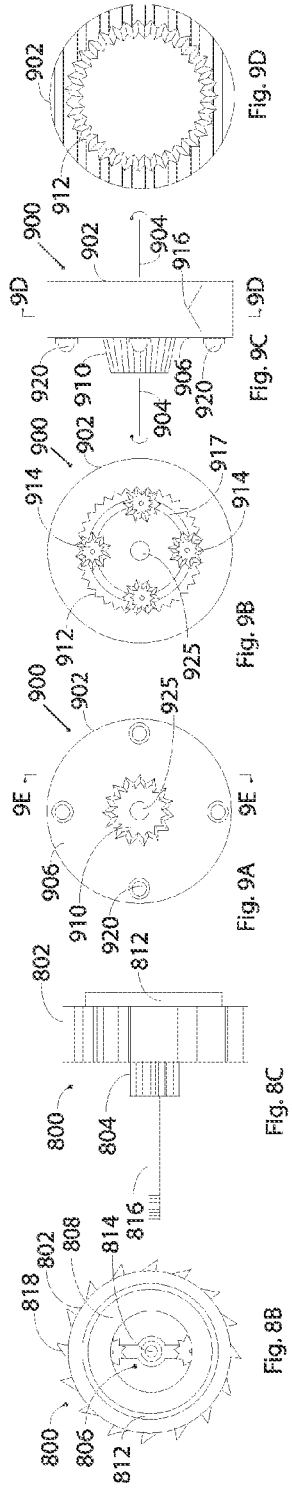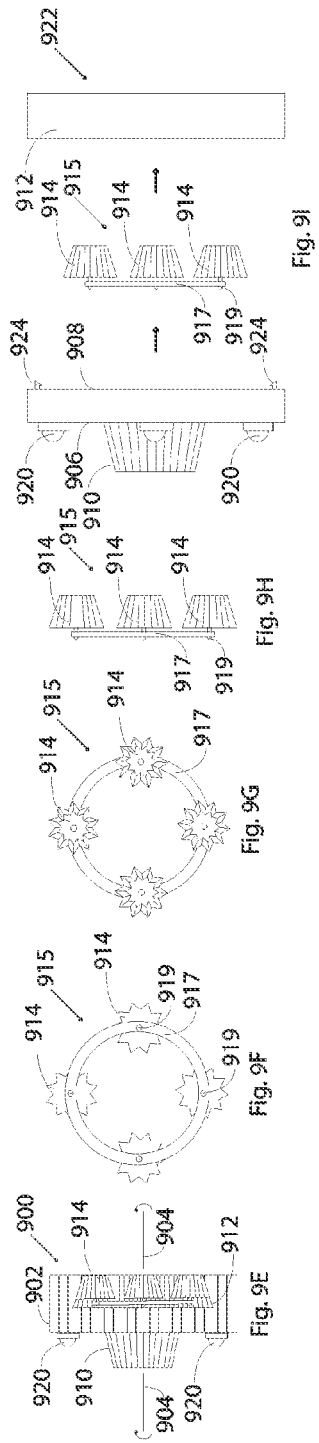

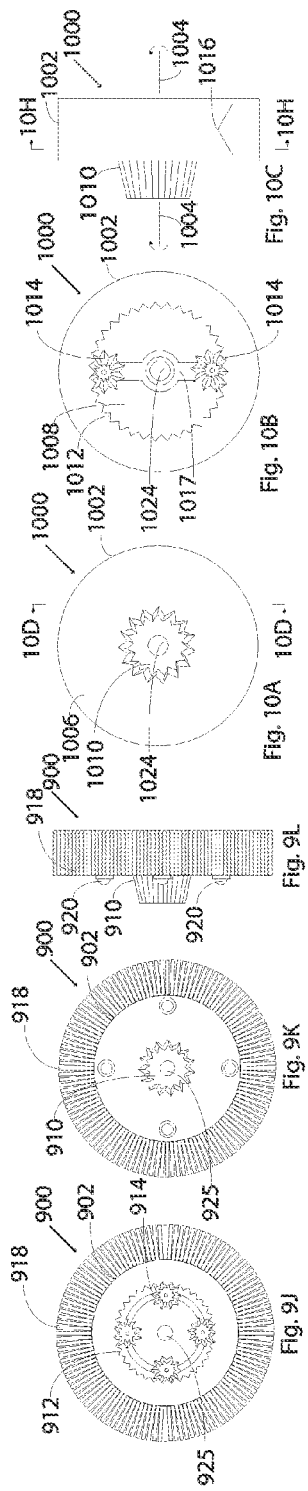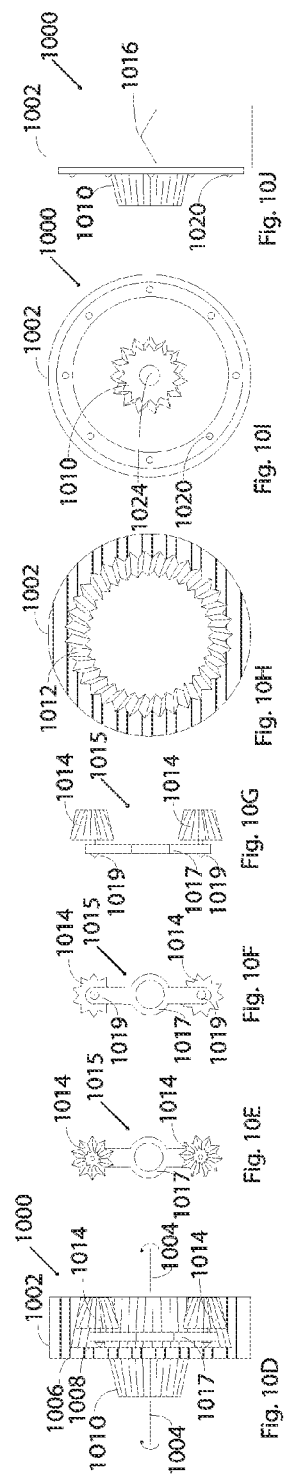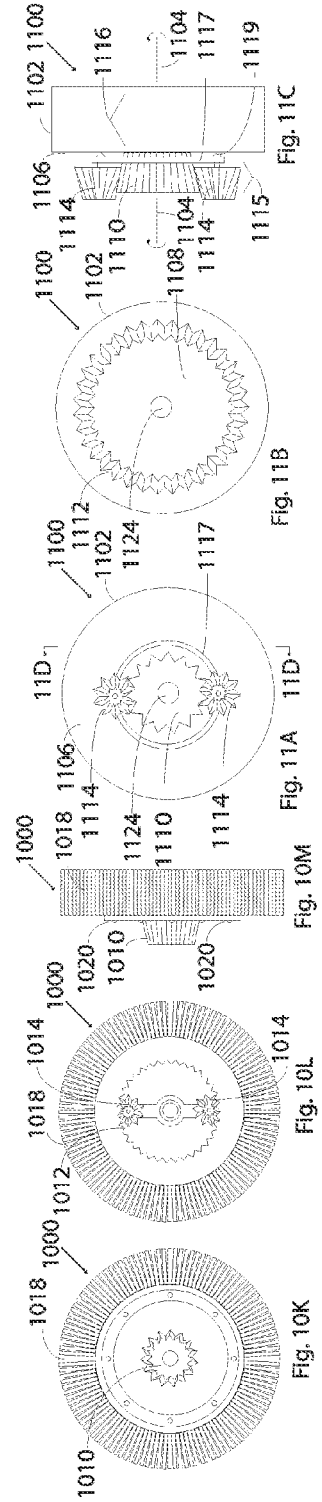

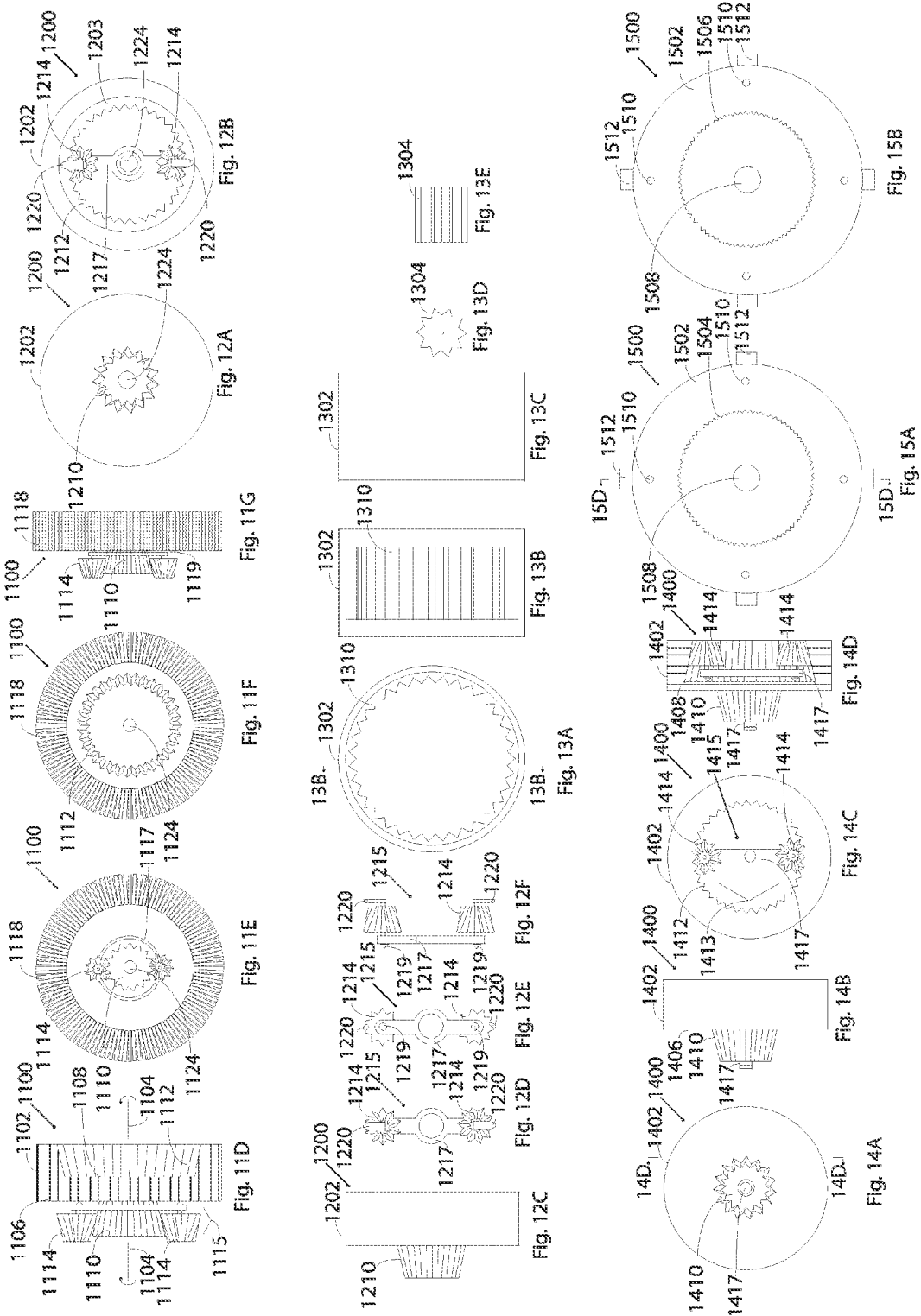

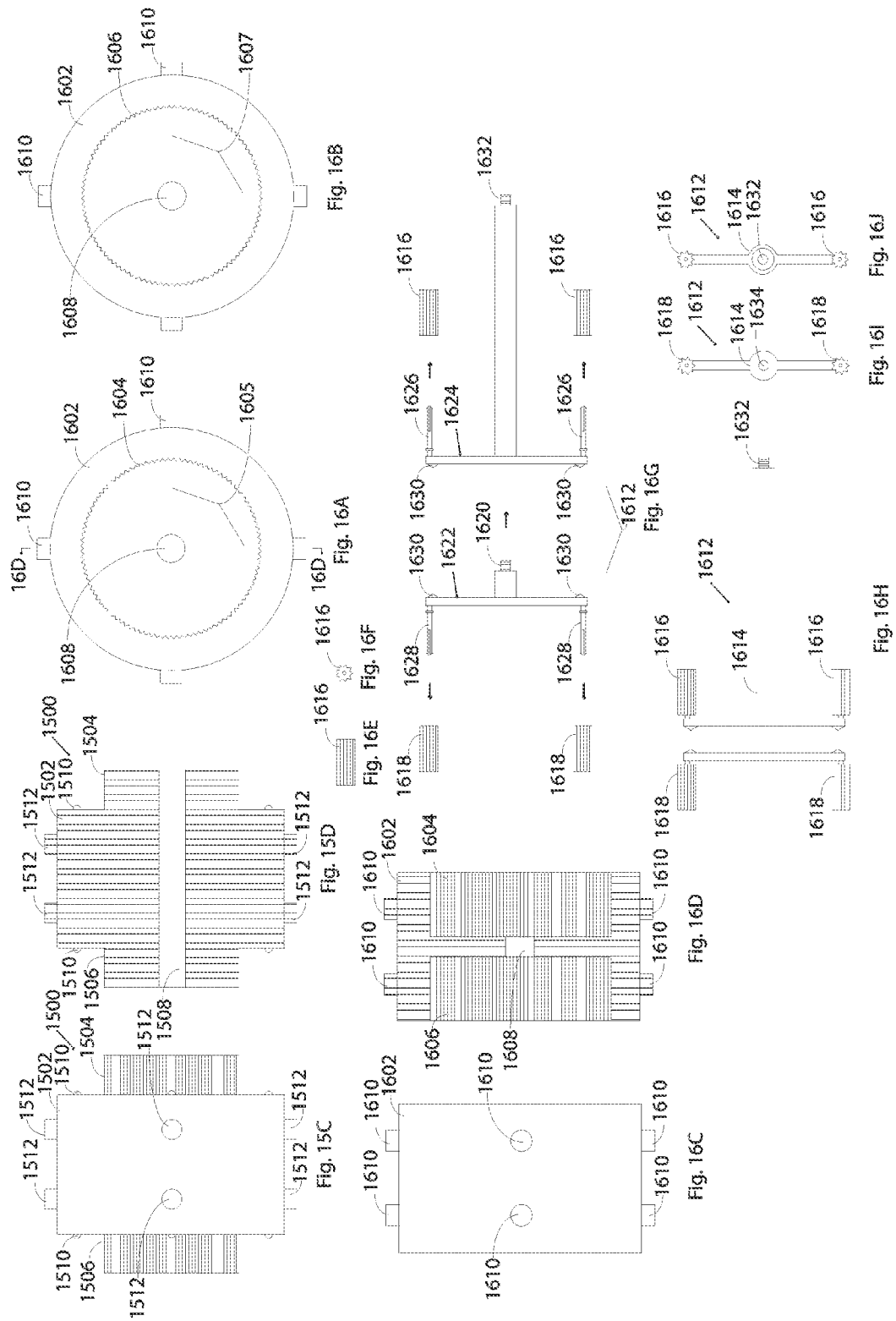

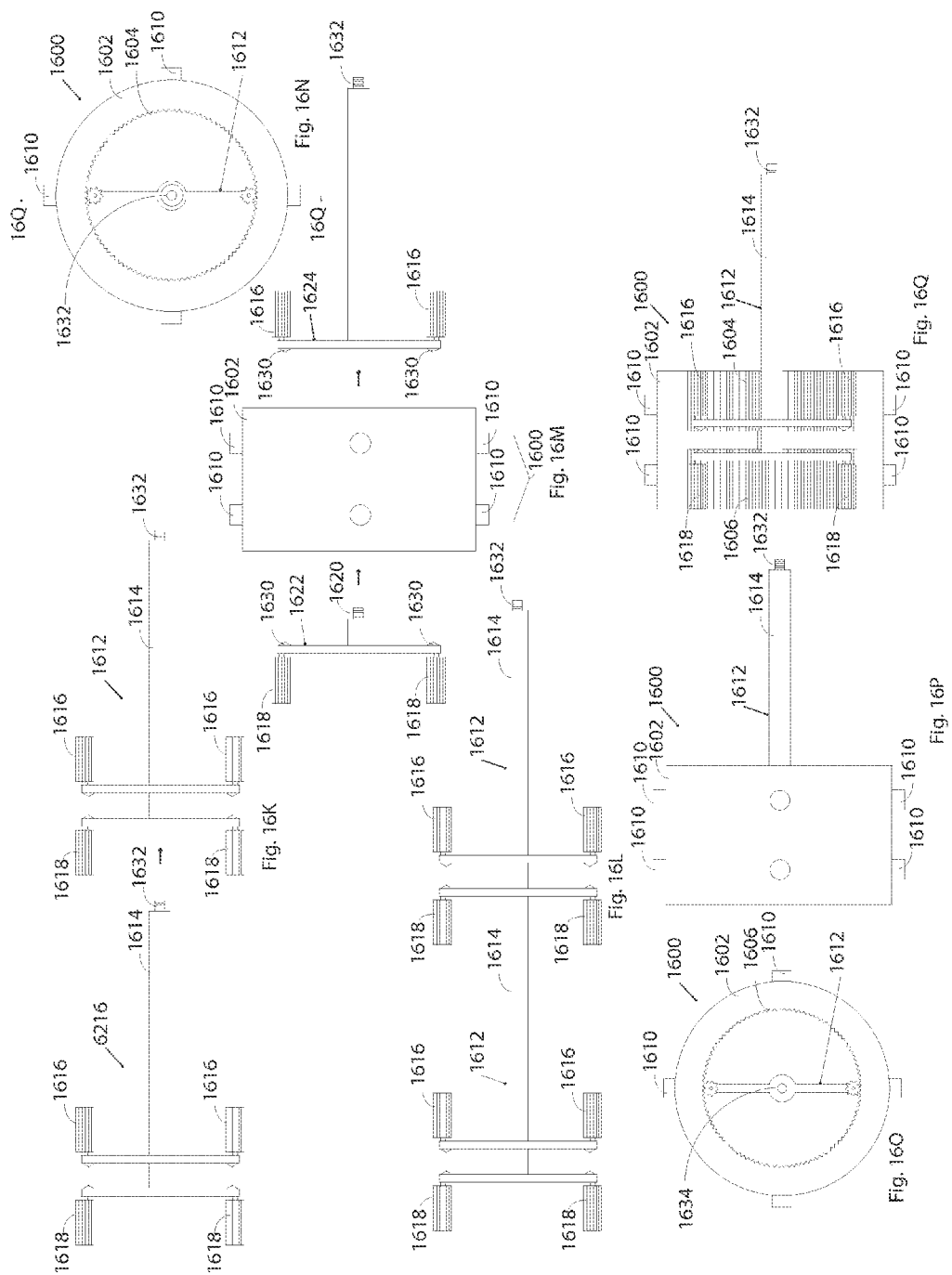

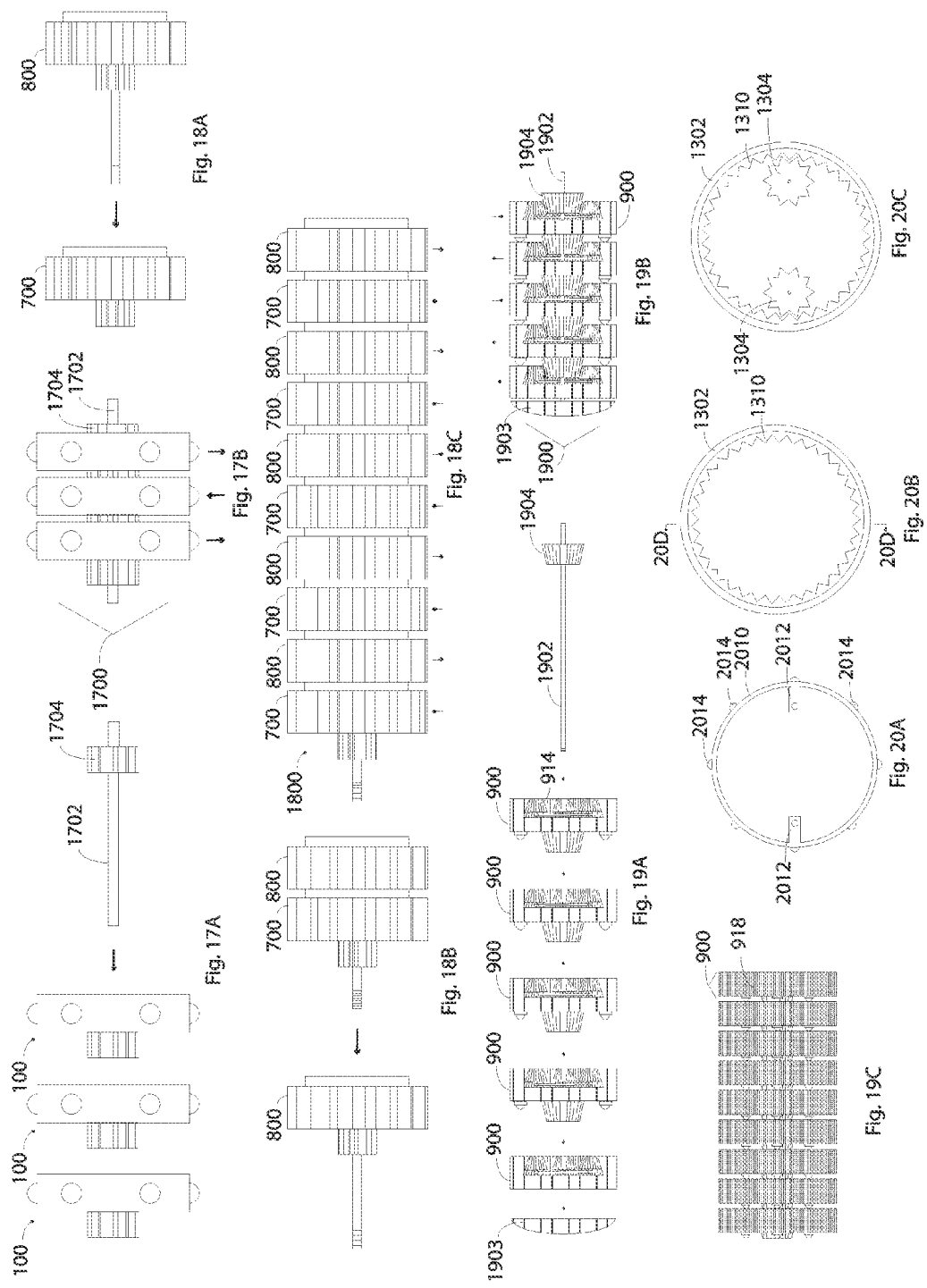

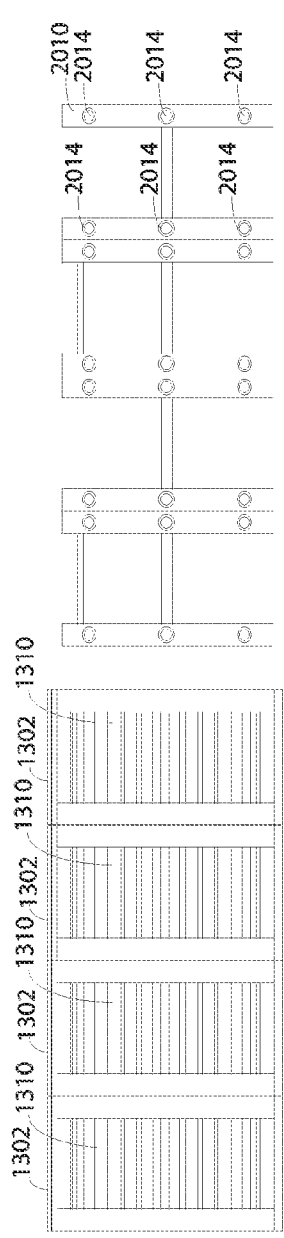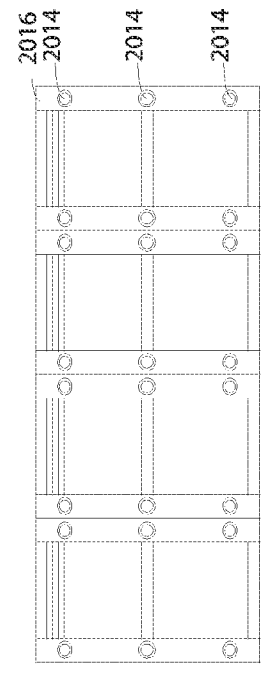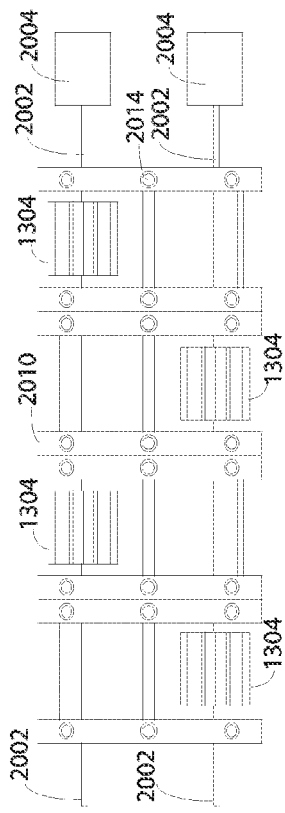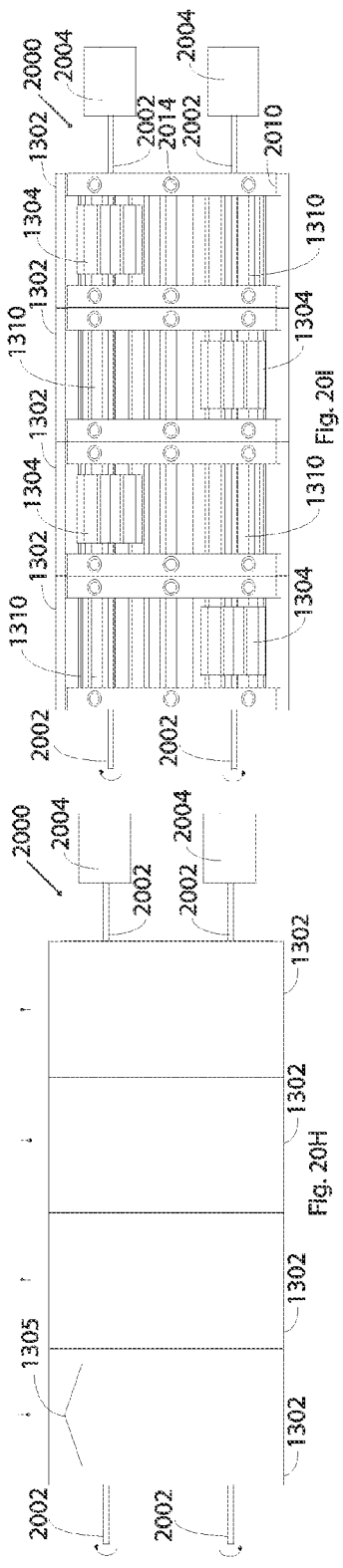

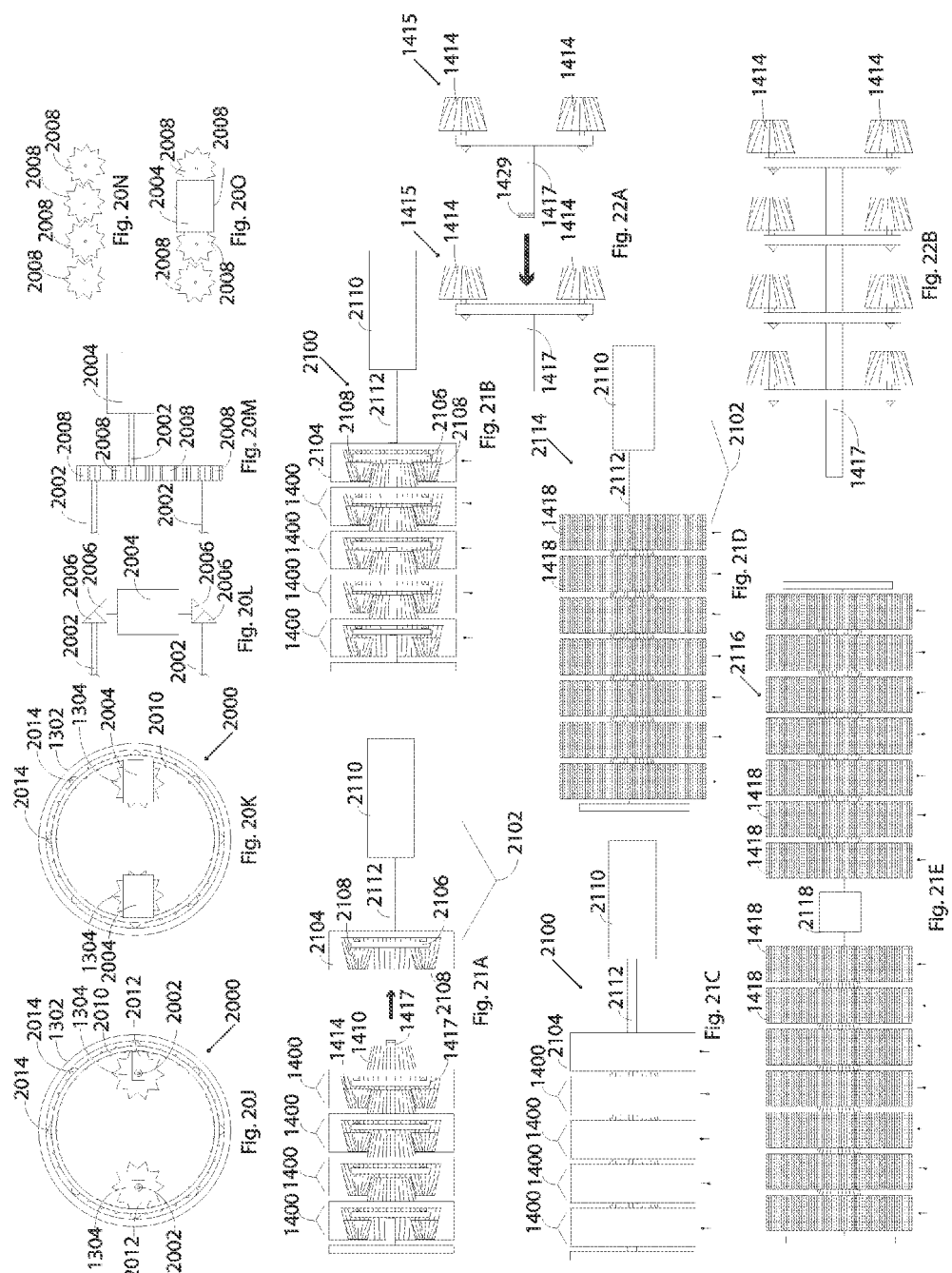

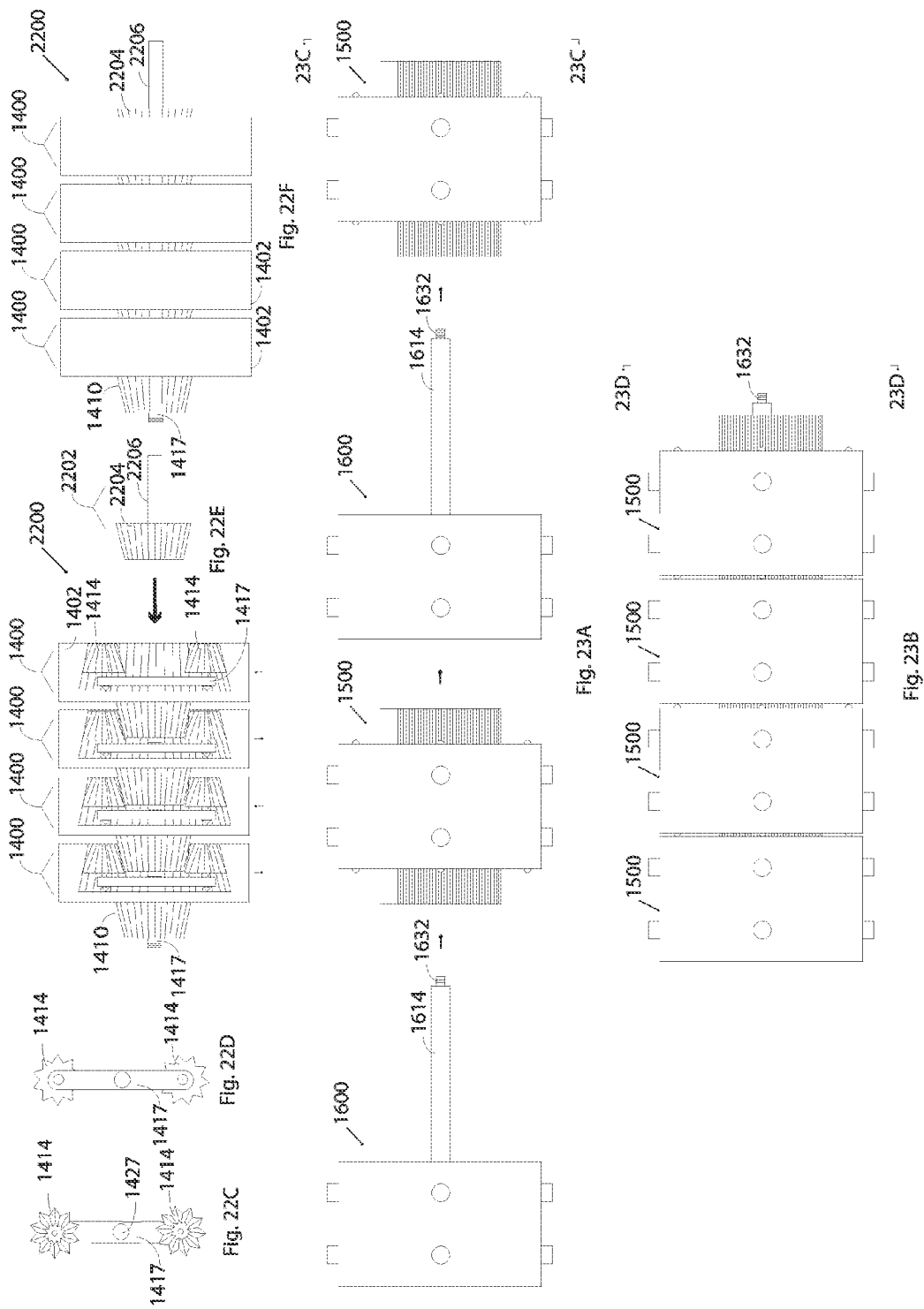

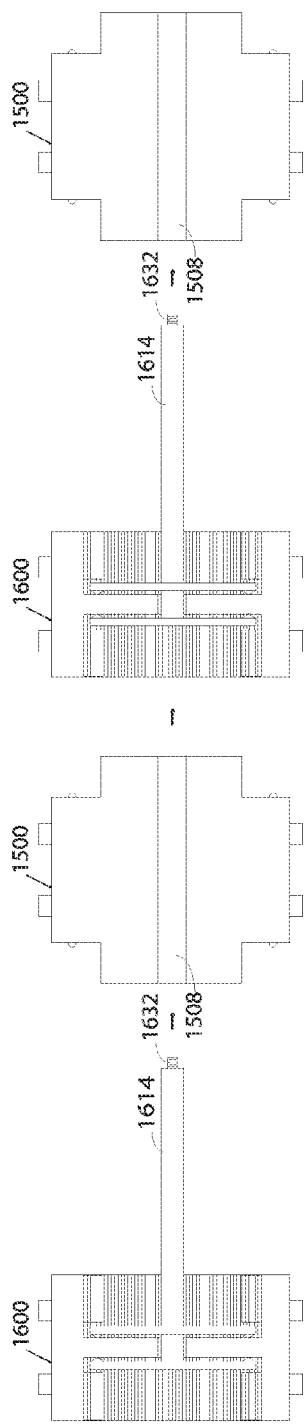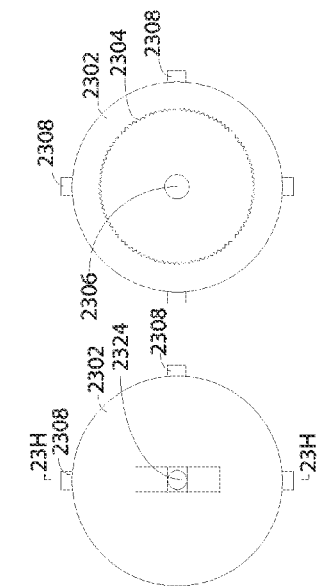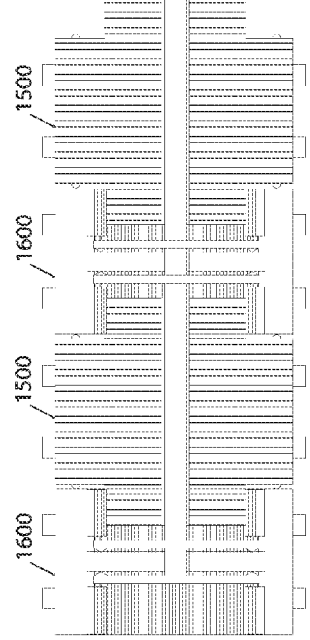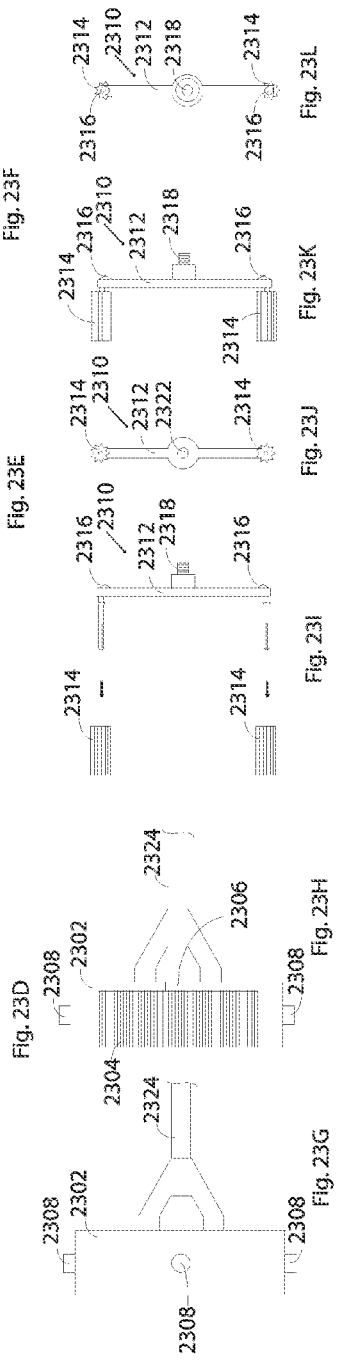

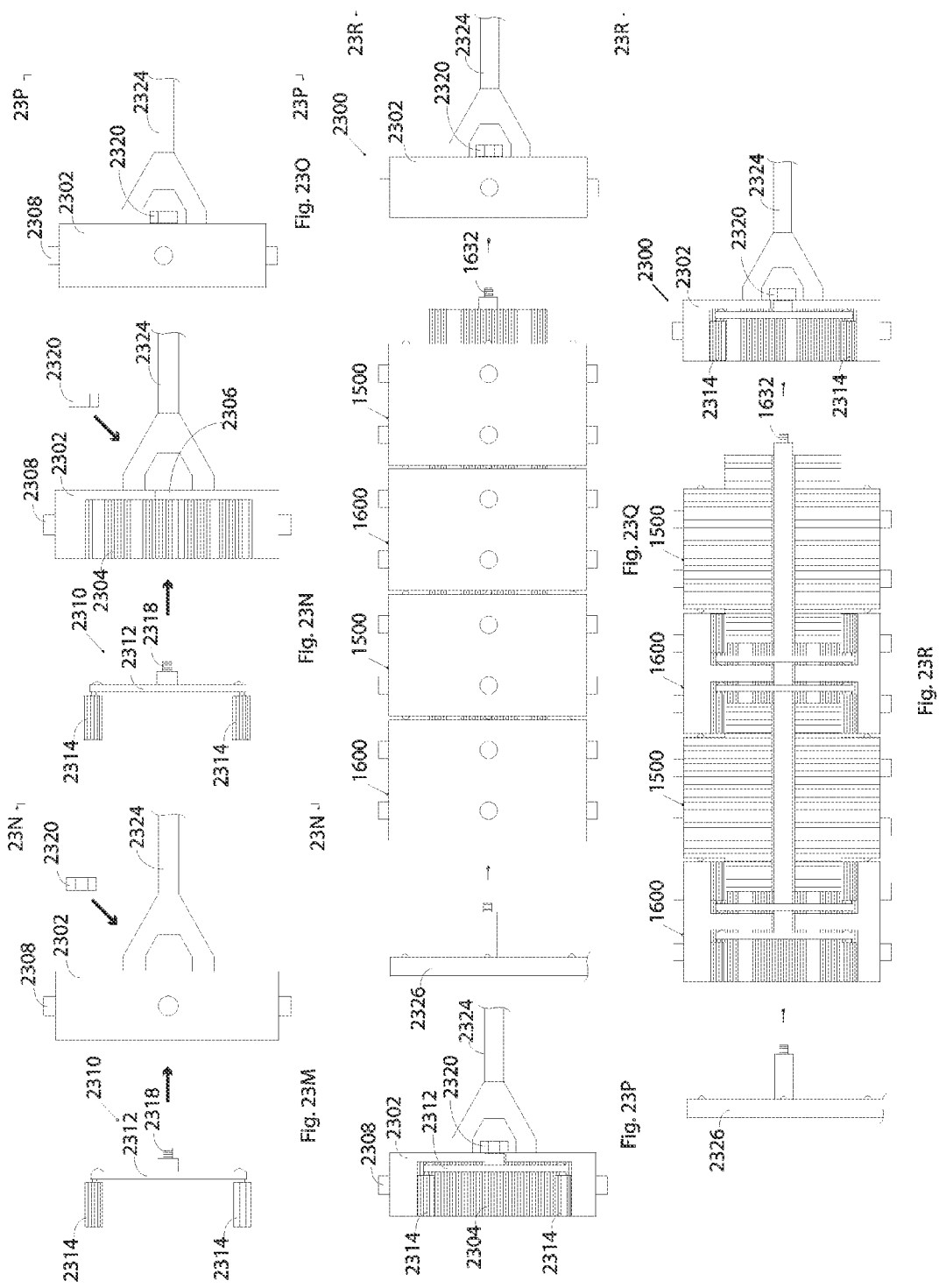

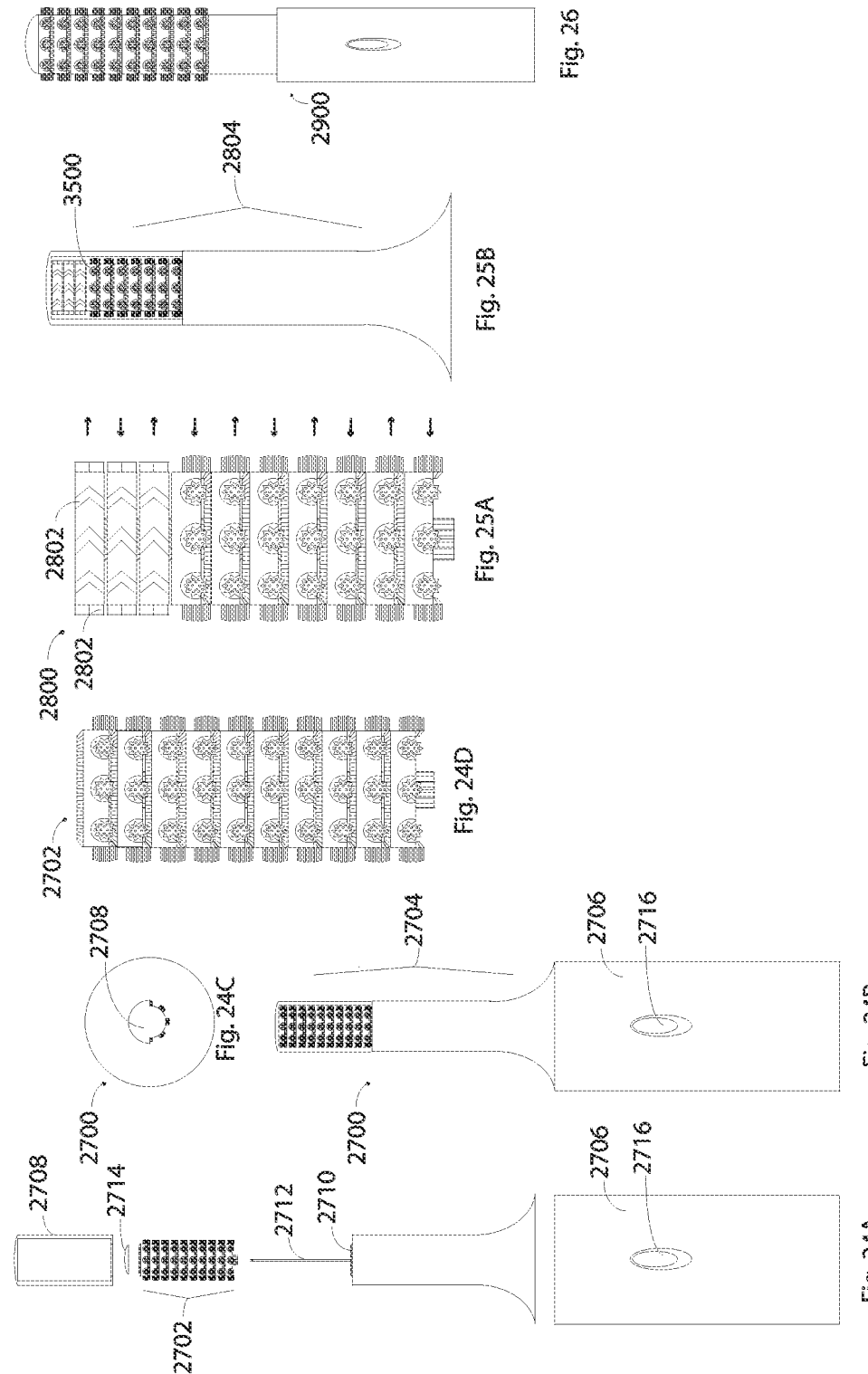

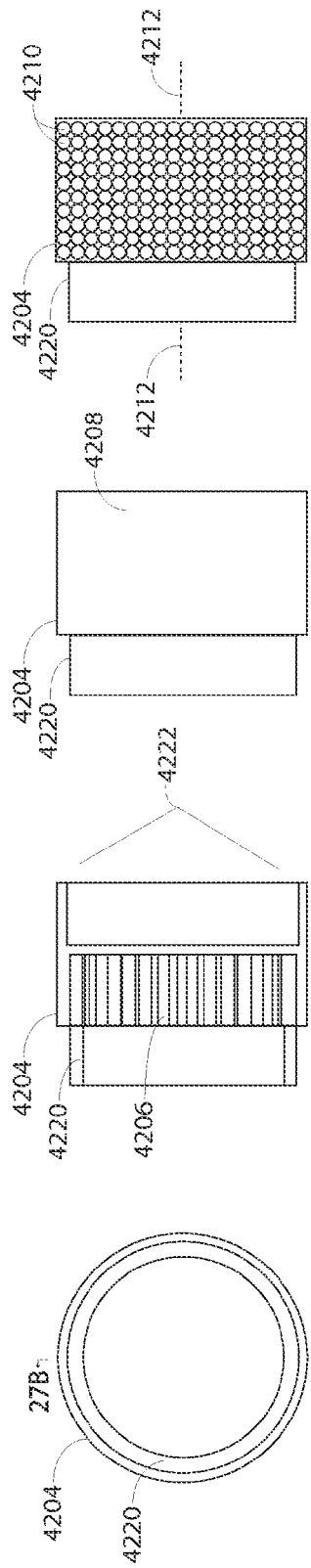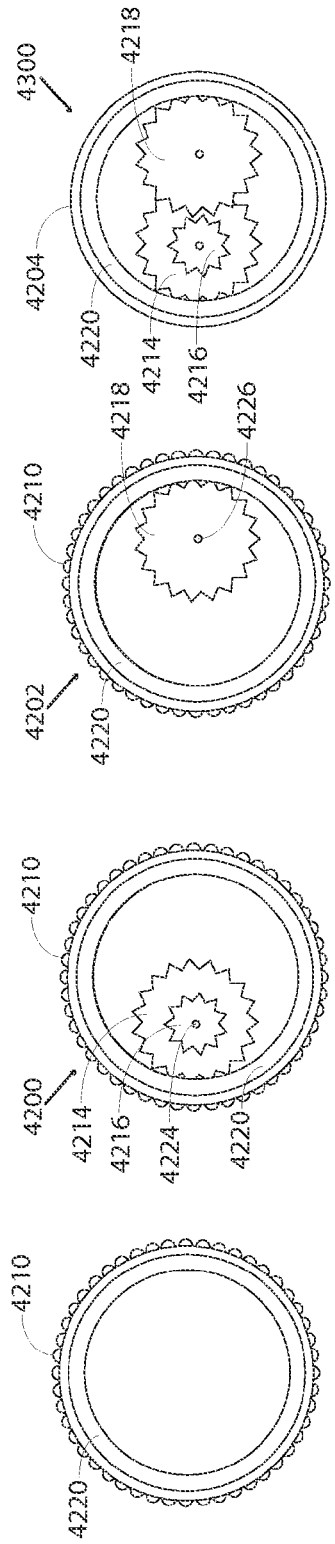

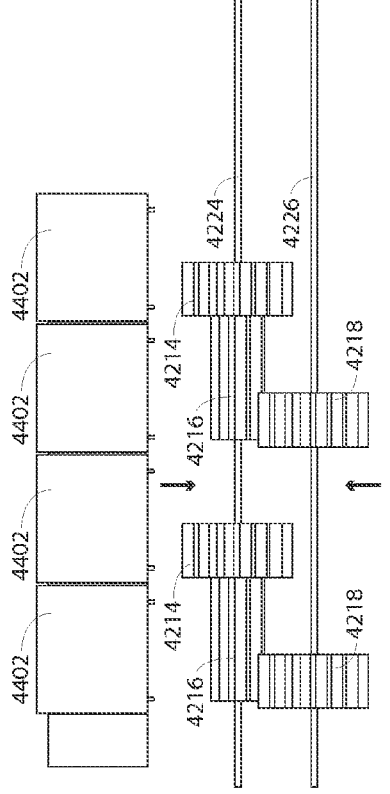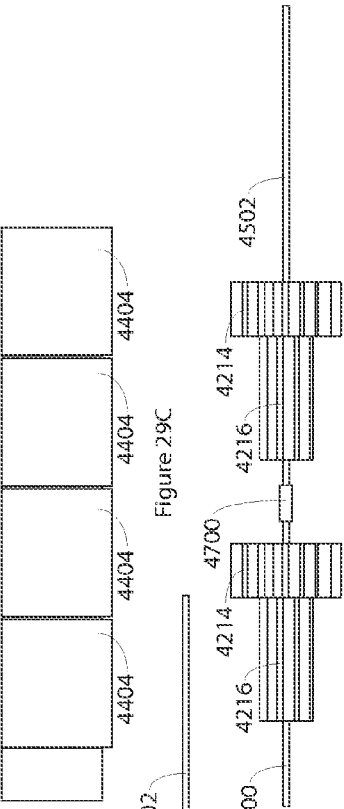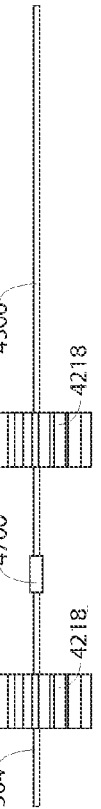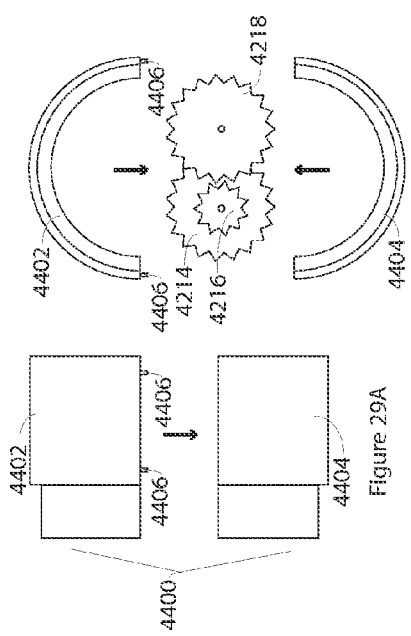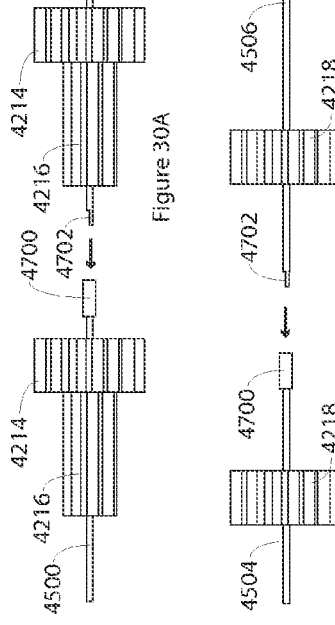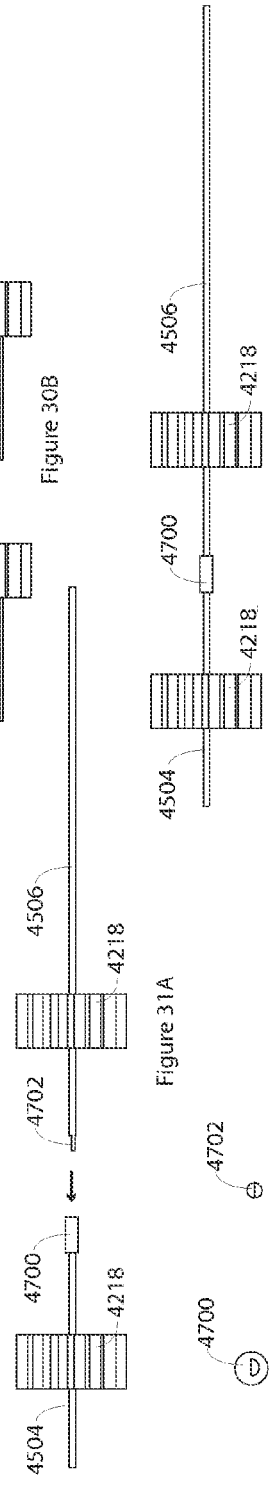
Figure 29A, Figure 29B, Figure 29C, Figure 30A, Figure 30B, Figure 31A, Figure 31B, Figure 32A, Figure 32B

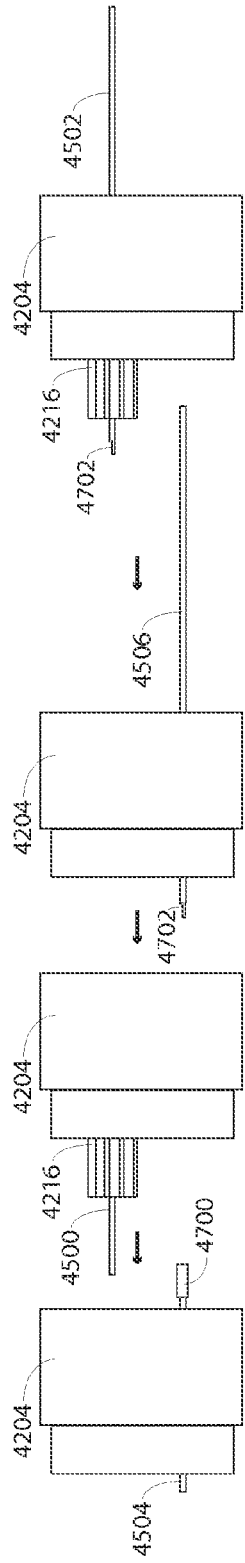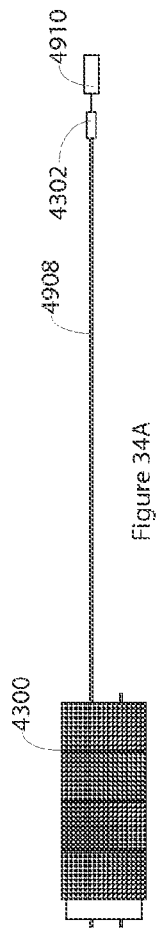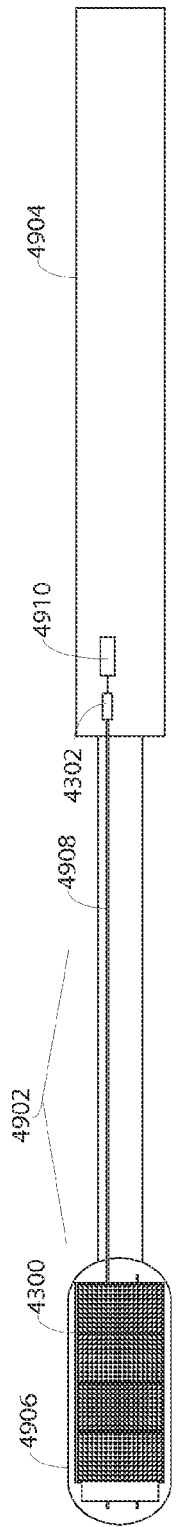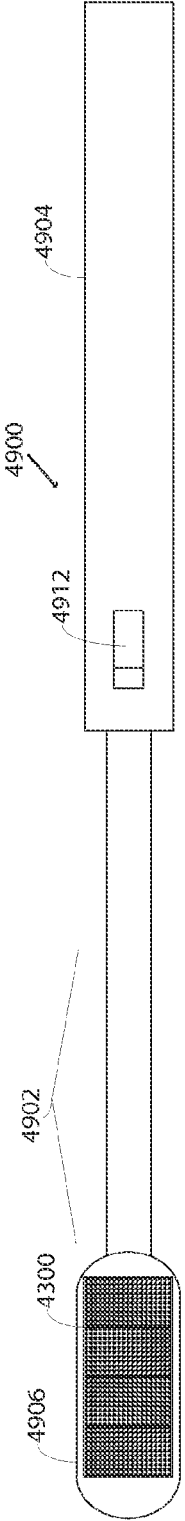
Figure 33
Figure 34A
Figure 34B
Figure 34C

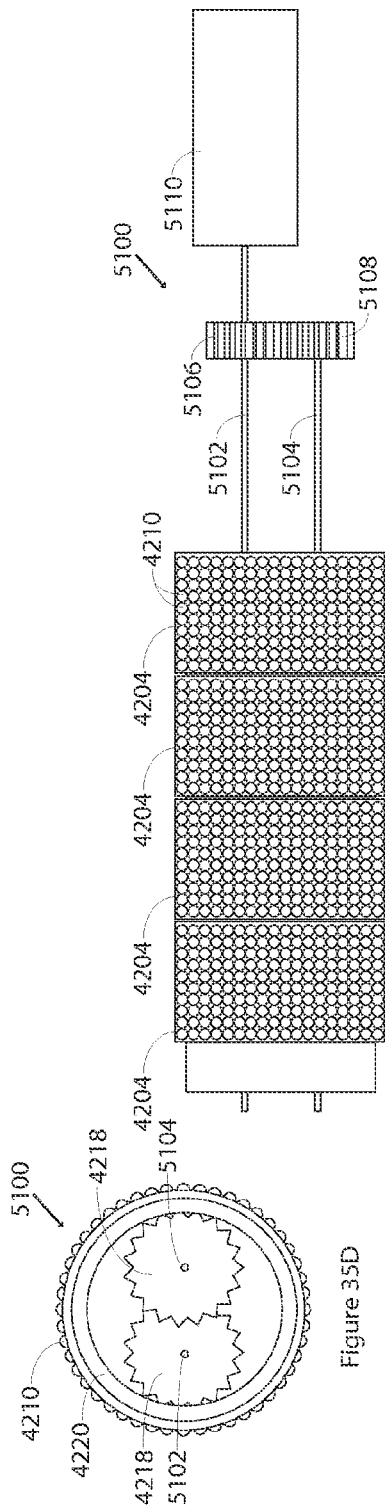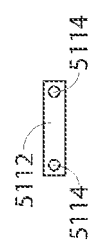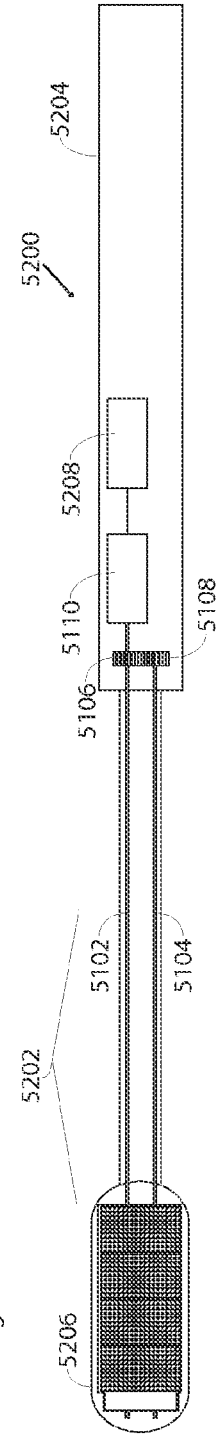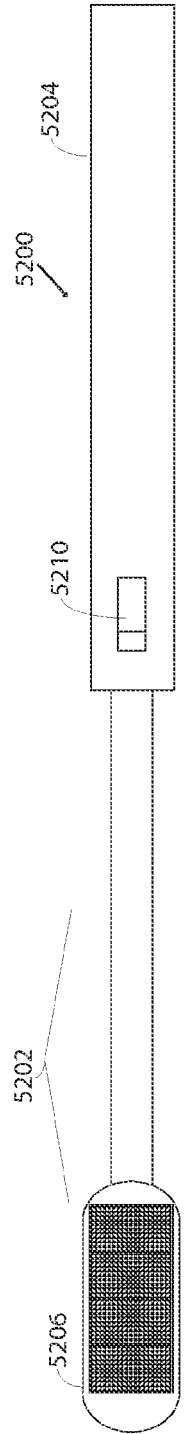
Figure 35E
Figure 35D
Figure 35F
Figure 36A
Figure 36B

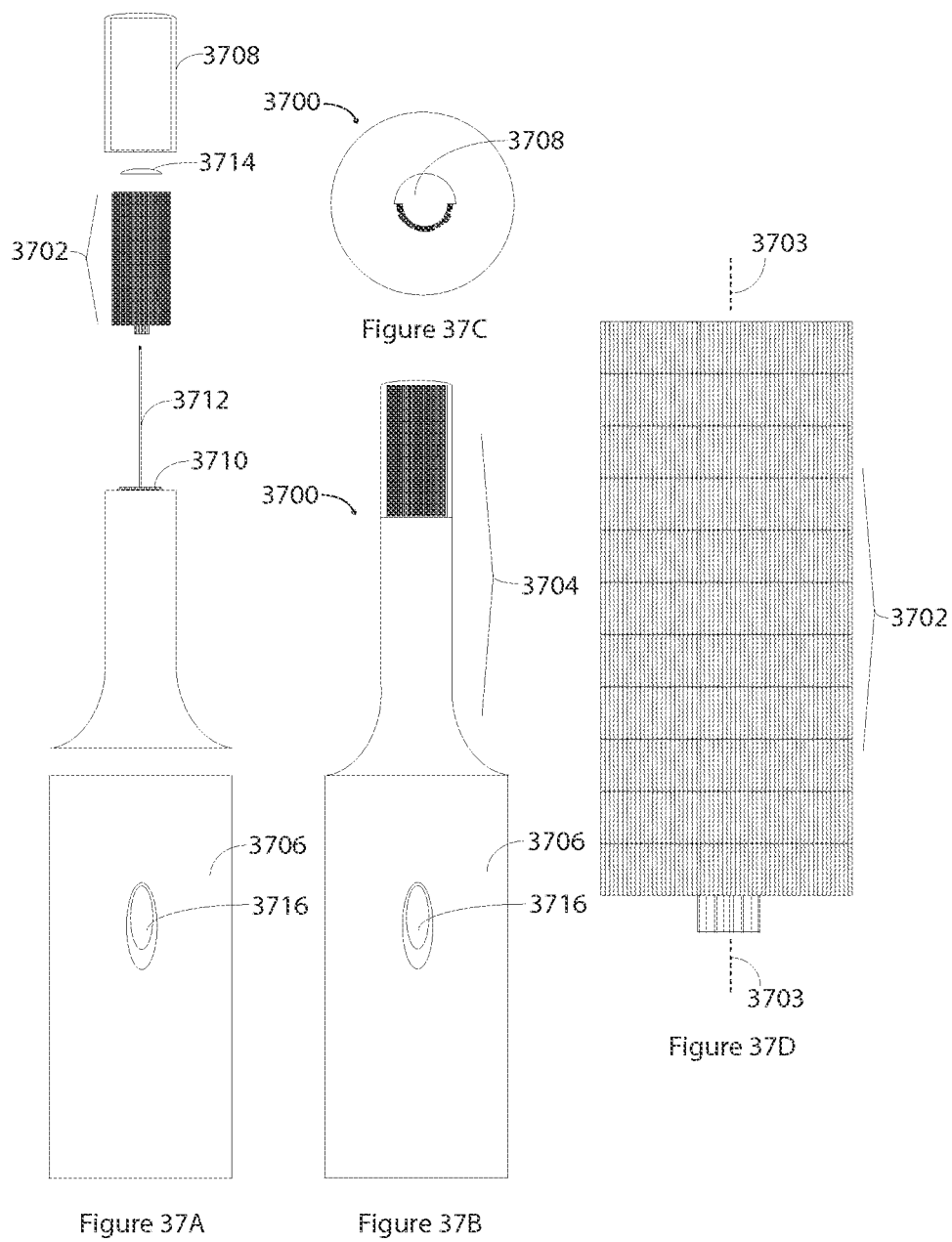

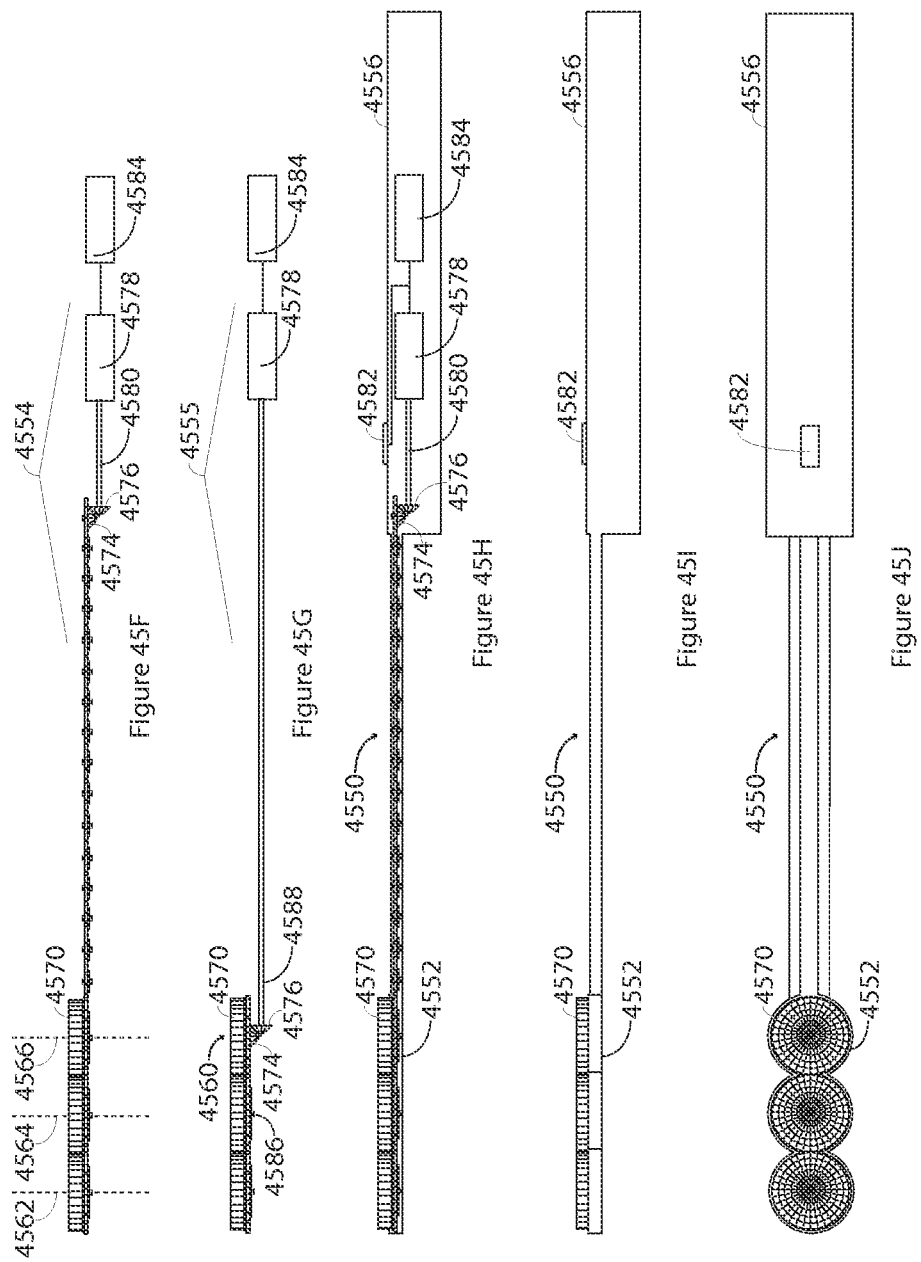

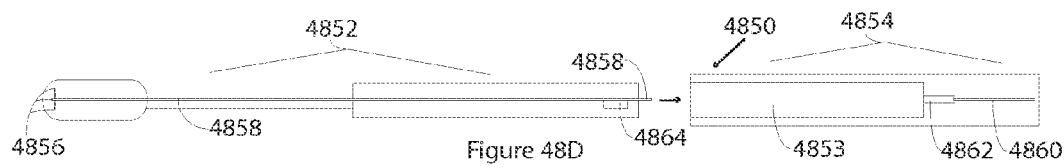
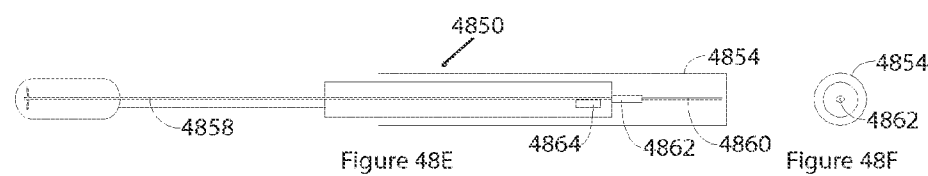
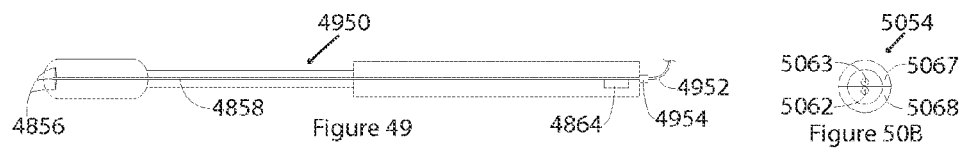
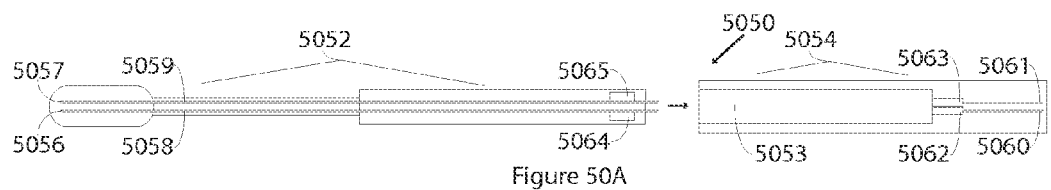
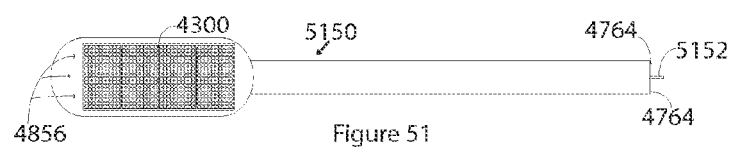

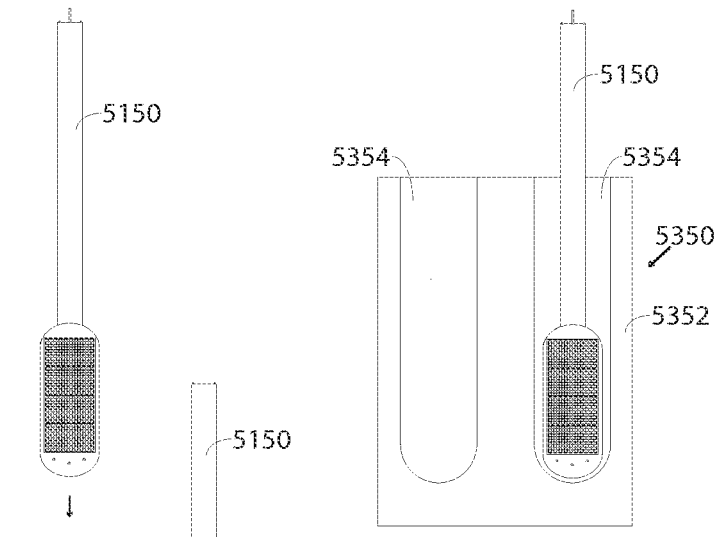
Figure 52B
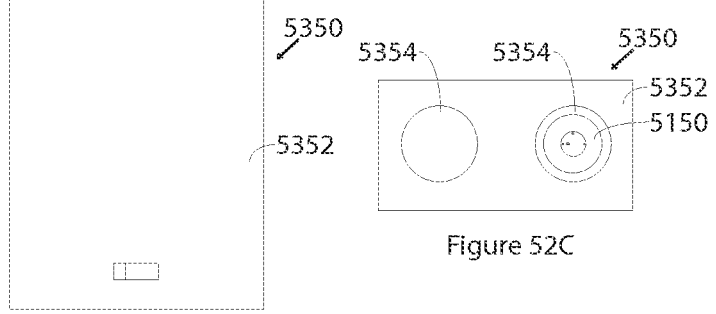
Figure 52C
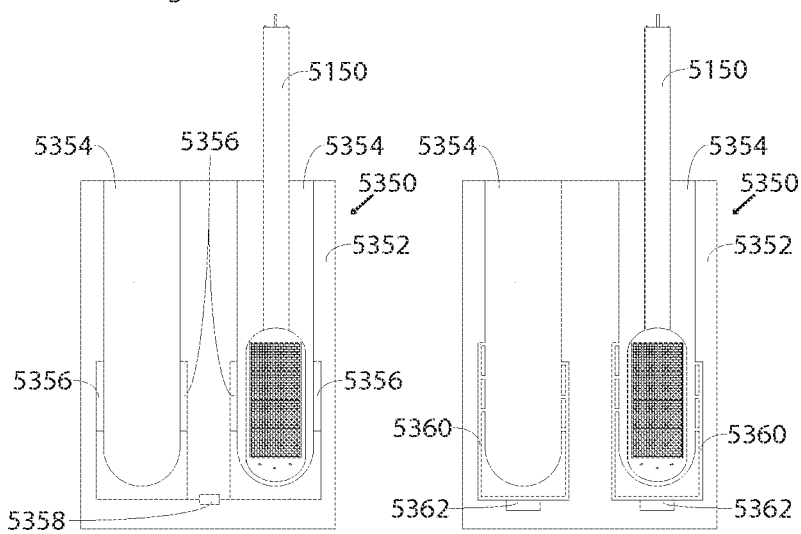
Figure 52A
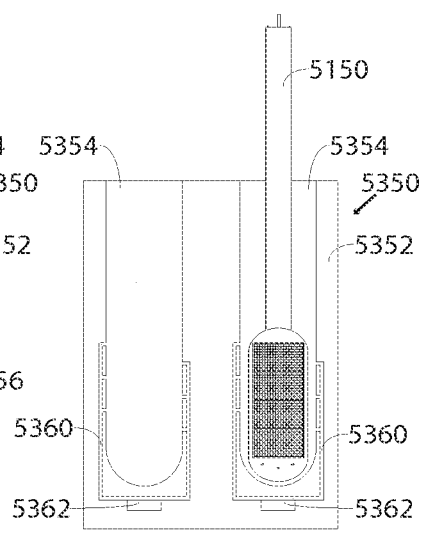
Figure 53
Figure 54

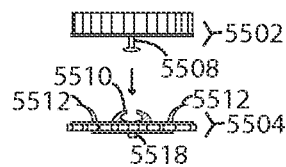
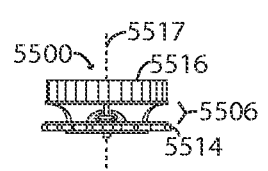
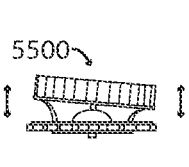
Figure 55A     Figure 55B     Figure 55C
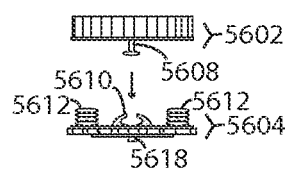
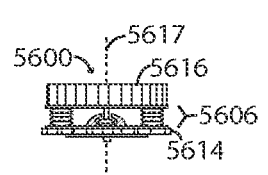
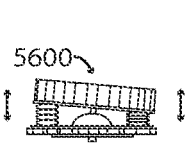
Figure 56A     Figure 56B     Figure 56C
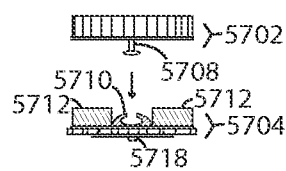
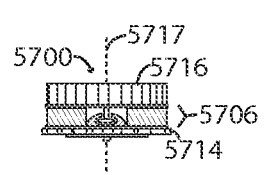
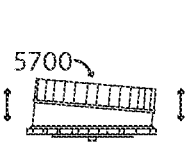
Figure 57A     Figure 57B     Figure 57C
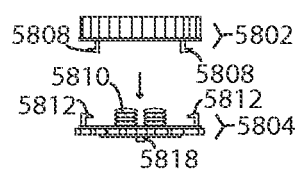
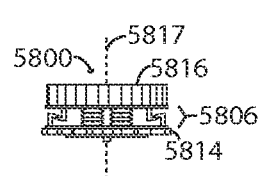
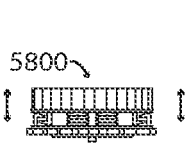
Figure 58A     Figure 58B     Figure 58C
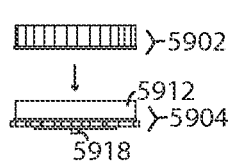
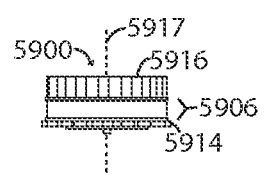
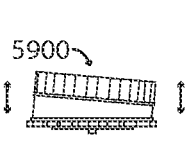
Figure 59A     Figure 59B     Figure 59C

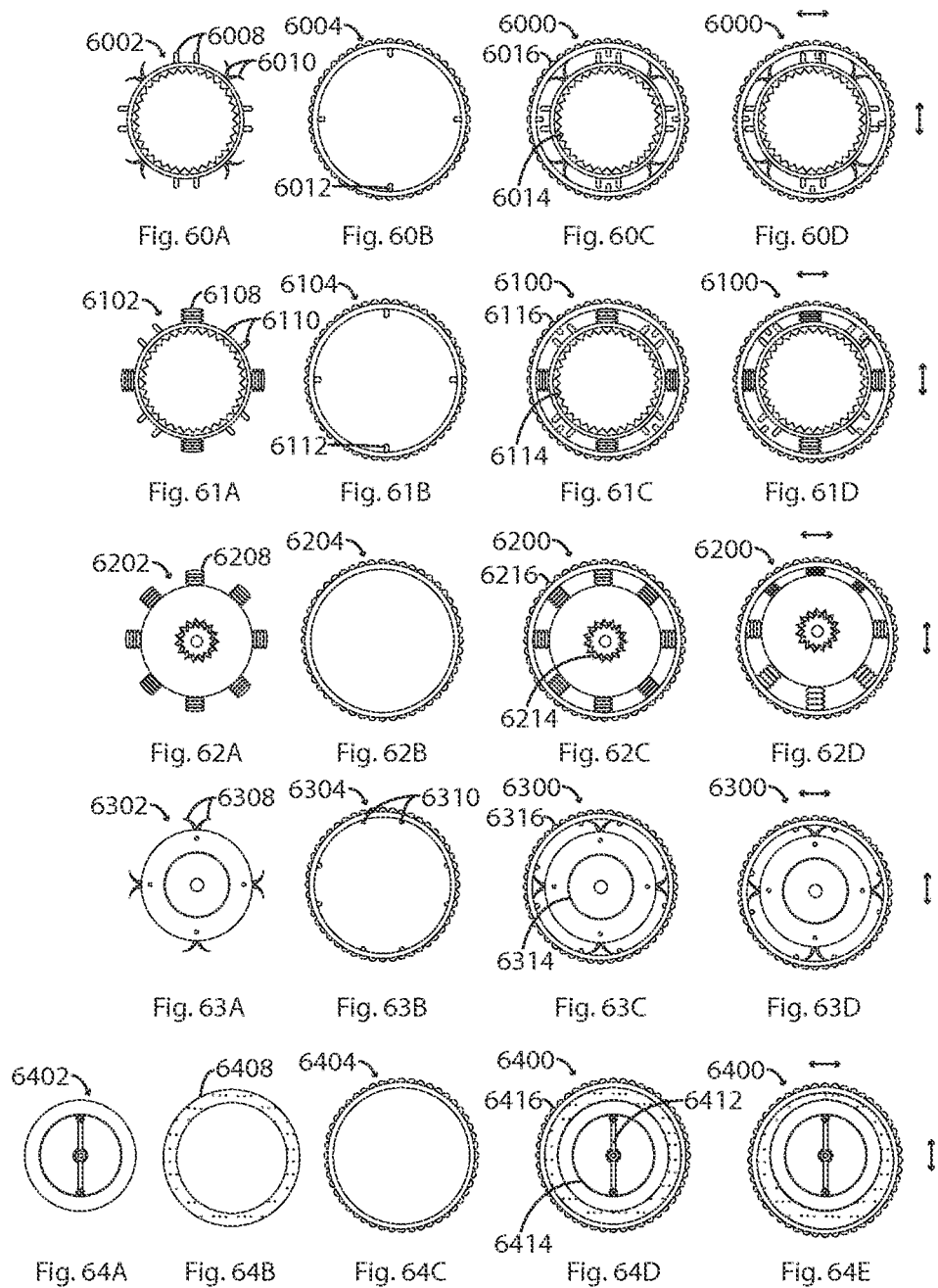

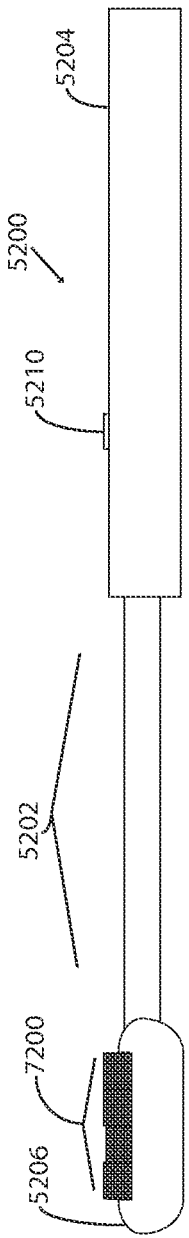
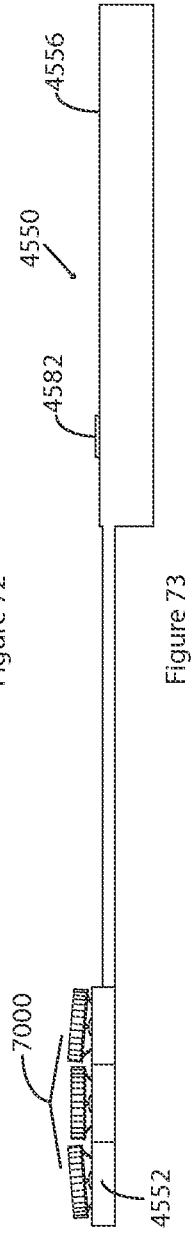
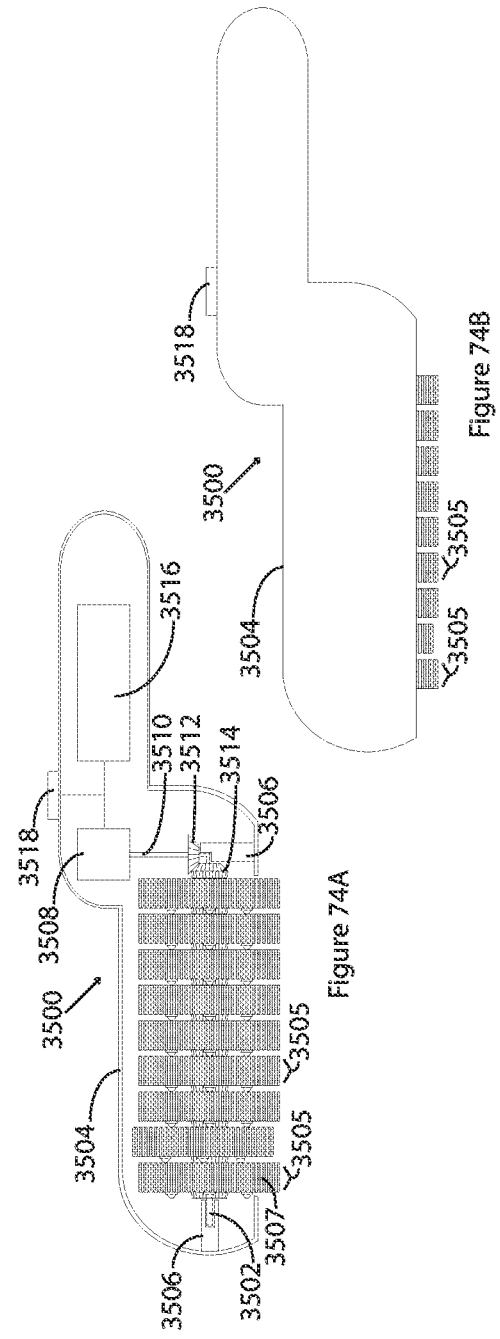

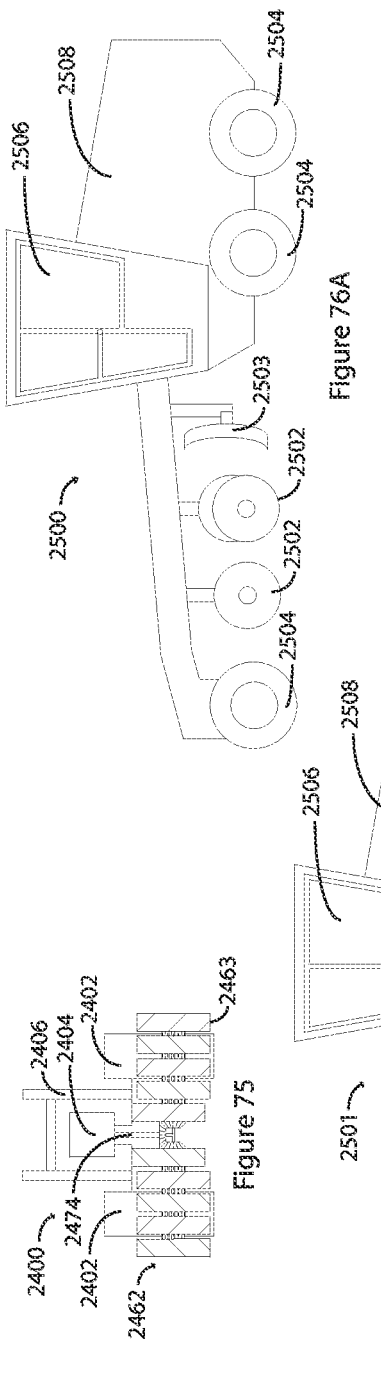
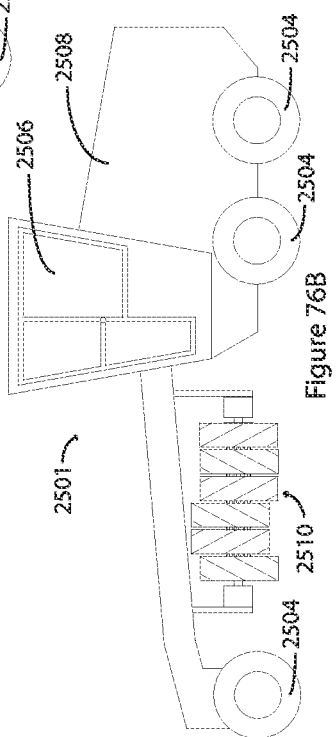
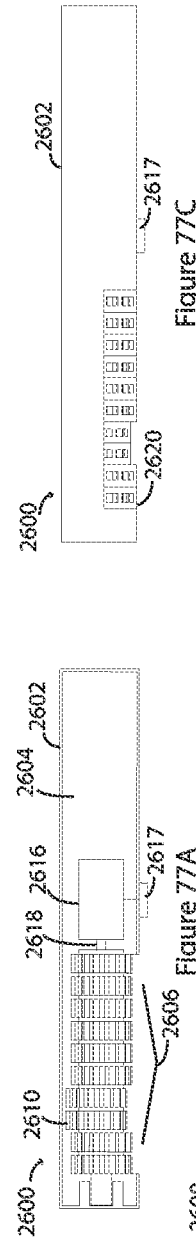
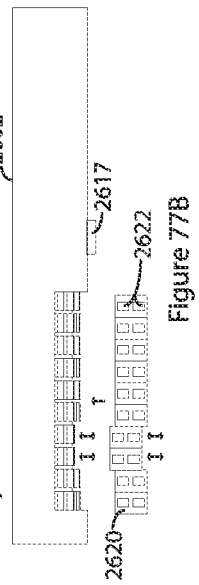

ROTARY UNITS, ROTARY MECHANISMS, AND RELATED APPLICATIONS

CROSS-REFERENCE TO RELATED APPLICATIONS

This application is a continuation-in-part of, and claims the benefit of priority from, U.S. Non-Provisional patent application Ser. No. 14/187,302, filed Feb. 23, 2014, which is a continuation of, and claims the benefit of priority from, U.S. Non-Provisional patent application Ser. No. 13/451,468, filed Apr. 19, 2012 (now U.S. Pat. No. 8,684,883, issued Apr. 1, 2014), which is a continuation-in-part of, and claims the benefit of priority from, U.S. Non-Provisional patent application Ser. No. 13/423,413, filed Mar. 19, 2012 (now U.S. Pat. No. 8,672,799, issued Mar. 18, 2014), which is a continuation-in-part of, and claims the benefit of priority from U.S. Non-Provisional patent application Ser. No. 13/219,683, filed Aug. 28, 2011 (now U.S. Pat. No. 8,715,133, issued May 6, 2014), which is a continuation-in-part of, and claims the benefit of priority from U.S. Non-Provisional patent application Ser. No. 13/184,332, filed Jul. 15, 2011 (now U.S. Pat. No. 8,668,618, issued Mar. 11, 2014), which claims the benefit of priority from U.S. Provisional Patent Application Nos. 61/365,290, filed Jul. 16, 2010 and 61/376,725, filed Aug. 25, 2010, which are each incorporated by reference in their entirety. U.S. Non-Provisional patent application Ser. No. 13/184,332, filed Jul. 15, 2011 (now U.S. Pat. No. 8,668,618, issued Mar. 11, 2014) is also continuation-in-part of, and claims the benefit of priority from, U.S. Non-Provisional patent application Ser. No. 12/577,326, filed Oct. 12, 2009 (now U.S. Pat. No. 8,152,679, issued Apr. 10, 2012), which claims the benefit of priority from U.S. Provisional Patent Application No. 61/104,748, filed on Oct. 12, 2008 and is a continuation of and claims the benefit of priority from International Patent Application No. PCT/US09/60386, filed on Oct. 12, 2009, which are each incorporated by reference in their entirety.

FIELD OF THE INVENTION

The invention relates generally to mechanical, electrical, or electromechanical devices, and provides rotary units, rotary mechanisms, methods, and related devices and other applications that are useful for a wide variety of purposes.

BACKGROUND OF THE INVENTION

Electromechanical devices are ubiquitous. Some of these devices include rotating components and are used in many different applications. Gardening took such as rotor tillers, for example, typically include rotating rotors having tines, which contact the soil during operation. Many other devices of use in agricultural and construction, among many other fields or applications also utilize various types of rotational components to achieve desired forms of work.

SUMMARY OF THE INVENTION

In one aspect, the invention provides a rotary mechanism that includes at least first, second, and third rotary units that each comprise at least one rotational component, wherein one or more of the rotational components comprise at least a first portion, at least a second portion, and at least one resilient coupling, wherein the resilient coupling resiliently couples the first and second portions to one another, and wherein at least one of the rotational components comprises at least one implement. The rotary mechanism also includes at least first and second counter-rotational mechanisms, wherein the first counter-rotational mechanism operably engages at least the rotational components of the first and second rotary units, and wherein the second counter-rotational mechanism operably engages at least the rotational components of the second and third rotary units. In addition, the rotary mechanism also includes at least one drive mechanism component or a portion thereof operably engaged with one or more of the rotational components and/or with one or more of the counter-rotational mechanisms, which drive mechanism component or portion thereof is configured at least to effect movement of the rotational components and the counter-rotational mechanisms such that the rotational components of the first and third rotary units rotate in a first direction and the rotational component of the second rotary unit rotates in a second direction. In some embodiments, the rotary mechanism includes more than three rotational components.

In certain embodiments, at least one of the rotational components comprises one or more gear components that are configured to operably engage one or more implements rotatably coupled to one or more other rotational components. In some embodiments, the implement is configured to effect the movement of one or more other components when the implement operably engages the other components. In certain embodiments, the implement comprises, e.g., one or more of: a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, a post, or the like. In some embodiments, at least a portion of the implement comprises at least one cross-sectional shape selected from the group consisting of: a circle, an oval, a square, a rectangle, a trapezoid, an irregular n-sided polygon, and a regular n-sided polygon. In certain embodiments, the implement is rotatably coupled to the rotational component. In some of these embodiments, the implement is configured to operably engage one or more gear components of one or more other rotational components.

In some embodiments, at least the first counter-rotational mechanism comprises at least a first gear component disposed on the first rotational component, at least a second gear component disposed on the second rotational component, and at least a third gear component that operably engages the first and second gear components such that when the first gear component rotates in the first direction, the second and third gear components rotate in the second direction and when the first gear component rotates in the second direction, the second and third gear components rotate in the first direction. In certain embodiments, the second gear component substantially defines a gear structure receiving area that is configured to receive at least a portion of the third gear component. In some embodiments, the rotary mechanism includes at least one gear structure that comprises at least one support component, wherein the third gear component is rotatably coupled to the support component. In certain embodiments, the gear structure is at least partially disposed in the gear structure receiving area.

In some embodiments, a device comprises one or more of the rotary mechanisms described herein. In certain embodiments, the device is selected from the group consisting of: a hand-held device, a rototiller, a hair cutting device, a massaging device, nail grooming device, a propulsion device, a woodworking device, a lathe, a woodchipping device, a machining device, a dermabrasion device, a medical device, a dental device, a cleaning device, an engine, a snowblower, a nozzle, a food preparation device, a grinder, a pencil sharpener, a lawn mower, a vacuum cleaner, a hair dryer, a plumbing device, a weapon, a surfboard, a scuba device, a component thereof, and a combination thereof.

In certain embodiments, a vehicle includes, e.g., an operably connected rotary mechanism described herein. In some embodiments, the vehicle is selected from the group consisting of: a farming vehicle, a mining vehicle, a construction vehicle, a submarine, an aircraft, a marine vehicle, a boat, a personal watercraft, and a military vehicle.

In certain embodiments, the resilient coupling comprises at least one positioning mechanism that positions the first and second portions relative to one another within a range of motion. In some embodiments, the resilient coupling comprises at least one spring mechanism. In some embodiments, the resilient coupling comprises at least one elastomeric material. In certain other exemplary embodiments, the resilient coupling comprises at least one material container component. In some of these embodiments, the material container component comprises at least one fluidic (e.g., a gas phase material, a liquid phase material, etc.) and/or semi-fluidic material.

In some embodiments, at least the first and second rotary units each comprise: at least one rotational component that comprises at least one sun gear component and at least one ring gear component. In these embodiments, the rotary mechanism typically includes at least one gear structure that comprises at least one support component and at least one planetary gear component rotatably coupled to the support component. The planetary gear component is generally configured to operably engage the ring gear component. The sun gear component of at least the first rotary unit typically operably engages the planetary gear component of at least the second rotary unit such that when the rotational component of the first rotary unit rotates in the first direction, the rotational component of the second rotary unit rotates in the second direction. In certain embodiments, the gear structure of the first rotary unit is operably connected to the gear structure of the second rotary unit such that the support components are substantially fixedly positioned relative to one another at least when the rotational component of the first rotary unit rotates in the first direction and the rotational component of the second rotary unit rotates in the second direction.

In certain embodiments, at least the first rotary unit comprises at least one rotational component that comprises at least first and second sun gear components, and at least the second rotary unit comprises at least one rotational component that comprises at least first and second ring gear components. In these embodiments, at least a first planetary gear component is typically configured to operably engage the second sun gear component of the first rotary unit and the first ring gear component of the second rotary unit such that when the rotational component of the first rotary unit rotates in the first direction, the rotational component of the second rotary unit rotates in the second direction. In some of these embodiments, the rotary mechanism includes at least one gear structure that comprises at least one support component, wherein the first planetary gear component is rotatably coupled to the support component, which support component is substantially fixedly positioned when the rotational component of the first rotary unit rotates in the first direction and the rotational component of the second rotary unit rotates in the second direction.

In some embodiments, at least the first and second rotary units each comprises: at least one rotational component that comprises at least one ring gear component, and at least one second gear component configured to operably engage the ring gear component. In certain embodiments, the drive mechanism component or portion thereof comprises at least two shaft components, wherein at least a first shaft component operably engages at least the second gear component of the first rotary unit and at least a second shaft component operably engages at least the second gear component of the second rotary unit.

In certain embodiments, at least the rotational components of the first and second rotary units each comprise at least one ring gear component, and at least one of the counter-rotational mechanisms comprises at least a first gear component that operably engages the ring gear component of at least the rotational component of the first rotary unit, at least a second gear component that operably engages the ring gear component of at least the rotational component of the second rotary unit, and at least a third gear component that operably engages at least the second gear component such that when the first gear component rotates in the first direction, the rotational component of the first rotary unit rotates in the first direction and the second gear component and the rotational component of the second rotary unit rotate in the second direction. In some of these embodiments, the drive mechanism component or portion thereof operably engages at least the first gear component, which drive mechanism component or portion thereof is configured to effect rotation of at least the first gear component.

In some embodiments, at least the rotational components of the first and second rotary units each comprise at least two ring gear components. In these embodiments, the rotary mechanism typically comprises at least a first planetary gear component that is configured to operably engage at least one of the ring gear components of the first rotary unit and at least one of the ring gear components of the second rotary unit such that when the rotational component of the first rotary unit rotates in the first direction, the rotational component of the second rotary unit rotates in the second direction. In some of these embodiments, the rotary mechanism includes at least one gear structure that comprises at least one support component, wherein the first planetary gear component is rotatably coupled to the support component, which support component is substantially fixedly positioned when the rotational component of the first rotary unit rotates in the first direction and the rotational component of the second rotary unit rotates in the second direction.

In another aspect, the invention provides a handheld device that includes a head portion comprising at least one rotary mechanism that comprises at least two rotational components, wherein at least a first rotational component is configured to rotate at least partially around a first rotational axis, wherein at least a second rotational component is configured to rotate at least partially around a second rotational axis, wherein one or more of the rotational components comprise at least a first portion, at least a second portion, and at least one resilient coupling that resiliently couples the first and second portions to one another, and wherein at least one of the rotational components comprises at least one implement. The handheld device also includes at least one drive mechanism component or portion thereof that operably engages, or is configured to operably engage, at least the rotary mechanism, which drive mechanism component or portion thereof is configured to effect rotation of at least the first rotational component at least partially around the first rotational axis in a first direction and the second rotational component at least partially around the second rotational axis in a second direction. In addition, the handheld device also includes a handle portion operably connected or connectable to the head portion.

In another aspect, the invention provides a rotary mechanism that includes at least first and second rotational components, wherein one or more of the rotational components comprise at least a first portion, at least a second portion, and at least one resilient coupling, wherein the resilient coupling resiliently couples the first and second portions to one another, and wherein at least one of the rotational components comprises at least one implement. The rotary mechanism also includes at least one counter-rotational mechanism that operably engages at least the first and second rotational components. In addition, the rotary mechanism also includes at least one drive mechanism component or a portion thereof operably engaged with one or more of the rotational components and/or with the counter-rotational mechanism, which drive mechanism component or portion thereof is configured at least to effect rotation of the rotational components such that the first rotational component rotates in a first direction and the second rotational component rotates in a second direction.

In another aspect, the invention provides a method of making a rotary unit. The method includes coupling at least two portions of at least a first rotational component together with at least one resilient coupling, wherein at least one of the portions comprises at least one implement and wherein at least one of the portions comprises at least a first gear component that is configured to operably engage at least a second gear component such that when the first rotational component is disposed proximal to at least a second rotational component and rotates in a first direction, the second rotational component rotates in a second direction, thereby making the rotary unit.

In another aspect, the invention provides a method of making a rotary mechanism. The method includes placing at least one counter-rotational mechanism into operable engagement with at least first and second rotational components, wherein one or more of the rotational components comprise at least a first portion, at least a second portion, and at least one resilient coupling, wherein the resilient coupling resiliently couples the first and second portions to one another, and wherein at least one of the rotational components comprises at least one implement. The method also includes placing at least one drive mechanism component or a portion thereof into operable engagement with one or more of the rotational components and/or with the counter-rotational mechanism, which drive mechanism component or portion thereof is configured at least to effect rotation of the rotational components such that the first rotational component rotates in a first direction and the second rotational component rotates in a second direction, thereby making the rotary mechanism.

BRIEF DESCRIPTION OF THE DRAWINGS

The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 1A schematically illustrates a rotary unit from a front side view according to one embodiment of the invention. FIG. 1B schematically shows the rotary unit of FIG. 1A from a rear side view. FIG. 1C schematically depicts the rotary unit of FIG. 1A from a side view. FIG. 1D schematically shows a gear structure of the rotary unit of FIG. 1A from a rear side view. FIG. 1E schematically illustrates the gear structure of FIG. 1D from a front side view. FIG. 1F schematically shows the gear structure of FIG. 1D from a side view. FIG. 1G schematically illustrates a sectional view of the rotary unit of FIG. 1A. FIG. 1H schematically shows a sectional view of the rotary unit of FIG. 1A. FIG. 1I schematically depicts a partially exploded view of the rotary unit of FIG. 1A.

FIGS. 2 A-F schematically show side elevational views of various exemplary implements.

FIG. 3A schematically illustrates a rotary unit from a front side view according to one embodiment of the invention. FIG. 3B schematically shows the rotary unit of FIG. 3A from a rear side view. FIG. 3C schematically shows the rotary unit of FIG. 3A from a side view. FIG. 3D schematically depicts a sectional view of the rotary unit of FIG. 3A. FIG. 3E schematically shows a gear structure of the rotary unit of FIG. 3A from a rear side view. FIG. 3F schematically shows a gear structure of the rotary unit of FIG. 3A from a front side view. FIG. 3G schematically shows a gear structure of the rotary unit of FIG. 3A from a side view.

FIG. 4A schematically illustrates a rotary unit from a front side view according to one embodiment of the invention. FIG. 4B schematically shows the rotary unit of FIG. 4A from a rear side view. FIG. 4C schematically shows the rotary unit of FIG. 4A from a side view, FIG. 4D schematically depicts a sectional view of the rotary unit of FIG. 4A. FIG. 4E schematically shows a gear structure of the rotary unit of FIG. 4A from a front side view. FIG. 4F schematically shows a gear structure of the rotary unit of FIG. 4A from a rear side view. FIG. 4G schematically shows a gear structure of the rotary unit of FIG. 4A from a side view.

FIG. 5A schematically illustrates a rotary unit from a side view according to one embodiment of the invention. FIG. 5B schematically shows a sectional view of the rotary unit of FIG. 5A.

FIG. 6A schematically shows a rotary unit from a front side view according to one embodiment of the invention. FIG. 6B schematically illustrates the rotary unit of FIG. 6A from a side view. FIG. 6C schematically depicts the rotary unit of FIG. 6A from a rear side view. FIG. 6D schematically shows a sectional view of the rotary unit of FIG. 6A. FIG. 6E schematically illustrates a gear structure of the rotary unit of FIG. 6A from a rear side view. FIG. 6F schematically shows the gear structure of FIG. 6E from a front side view. FIG. 6G schematically illustrates the gear structure of FIG. 6E from a side view.

FIG. 7A schematically shows a rotary unit from a front side view according to one embodiment of the invention. FIG. 7B schematically shows the rotary unit of FIG. 7A from a rear side view. FIG. 7C schematically depicts the rotary unit of FIG. 7A from a side view.

FIG. 8A schematically shows a rotary unit from a front side view according to one embodiment of the invention. FIG. 8B schematically shows the rotary unit of FIG. 8A from a rear side view. FIG. 8C schematically depicts the rotary unit of FIG. 8A from a side view.

FIG. 9A schematically illustrates a rotary unit from a front side view according to one embodiment of the invention. FIG. 9B schematically shows the rotary unit of FIG. 9A from a rear side view. FIG. 9C schematically depicts the rotary unit of FIG. 9A from a side view. FIG. 9D schematically shows a sectional view of the rotary unit of FIG. 9A. FIG. 9E schematically illustrates a sectional view of the rotary unit of FIG. 9A. FIG. 9F schematically shows a gear structure of the rotary unit of FIG. 9A from a rear side view. FIG. 9G schematically illustrates the gear structure of FIG. 9F from a front side view. FIG. 9H schematically shows the gear structure of FIG. 9F from a side view. FIG. 9I schematically depicts a partially exploded view of the rotary unit of FIG. 9A. FIG. 9J schematically shows the rotary unit of FIG. 9A with implements from a rear side view. FIG. 9K schematically shows the rotary unit of FIG. 9A with implements from a front side view. FIG. 9L schematically shows the rotary unit of FIG. 9A with implements from a side view.

FIG. 10A schematically illustrates a rotary unit from a front side view according to one embodiment of the invention. FIG. 10B schematically shows the rotary unit of FIG. 10A from a rear side view. FIG. 10C schematically depicts the rotary unit of FIG. 10A from a side view. FIG. 10D schematically shows a sectional view of the rotary unit of FIG. 10A. FIG. 10E schematically shows a gear structure of the rotary unit of FIG. 10A from a front side view. FIG. 10F schematically illustrates the gear structure of FIG. 10E from a rear side view. FIG. 10G schematically shows the gear structure of FIG. 10E from a side view. FIG. 10H schematically illustrates a sectional view of the rotary unit of FIG. 10A. FIG. 10I schematically depicts the rotary unit of FIG. 10A including a friction reducing material from a front side view. FIG. 10J schematically depicts the rotary unit of FIG. 10A including a friction reducing material from a side view. FIG. 10K schematically shows the rotary unit of FIG. 10I with implements from a front side view. FIG. 10L schematically shows the rotary unit of FIG. 10A with implements from a rear side view. FIG. 10M schematically shows the rotary unit of FIG. 10I with implements from a side view.

FIG. 11A schematically illustrates a rotary unit from a front side view according to one embodiment of the invention. FIG. 11B schematically shows the rotary unit of FIG. 11A from a rear side view. FIG. 11C schematically depicts the rotary unit of FIG. 11A from a side view. FIG. 11D schematically shows a sectional view of the rotary unit of FIG. 11A. FIG. 11E schematically shows the rotary unit of FIG. 11A with implements from a front side view. FIG. 11F schematically shows the rotary unit of FIG. 11A with implements from a rear side view. FIG. 11G schematically shows the rotary unit of FIG. 11A with implements from a side view.

FIG. 12A schematically illustrates a rotary unit from a front side view according to one embodiment of the invention. FIG. 12B schematically shows the rotary unit of FIG. 12A from a rear side view. FIG. 12C schematically depicts the rotary unit of FIG. 12A from a side view. FIG. 12D schematically shows a gear structure of the rotary unit of FIG. 12A from a front side view. FIG. 12E schematically illustrates the gear structure of FIG. 12D from a rear side view. FIG. 12F schematically shows the gear structure of FIG. 12D from a side view.

FIG. 13A schematically illustrates a rotational component of a rotary unit from a front side view according to one embodiment of the invention. FIG. 13B schematically shows a sectional view of the rotational component of FIG. 13A. FIG. 13C schematically depicts the rotational component of FIG. 13A from a side view. FIG. 13D schematically shows a gear component used in the rotary unit referred to with respect to FIG. 13A from a front side view. FIG. 13E schematically illustrates the gear component of FIG. 13D from a side view.

FIG. 14A schematically illustrates a rotary unit from a front side view according to one embodiment of the invention. FIG. 14B schematically depicts the rotary unit of FIG. 14A from a side view. FIG. 14C schematically shows the rotary unit of FIG. 14A from a rear side view. FIG. 14D schematically shows a sectional view of the gear structure of FIG. 14A.

FIG. 15A schematically illustrates a rotary unit from a front side view according to one embodiment of the invention. FIG. 15B schematically shows the rotary unit of FIG. 15A from a rear side view. FIG. 15C schematically depicts the rotary unit of FIG. 15A from a side view. FIG. 15D schematically shows a sectional view of the rotary unit of FIG. 15A.

FIG. 16A schematically illustrates a rotary unit from a front side view according to one embodiment of the invention. FIG. 16B schematically shows the rotary unit of FIG. 16A from a rear side view. FIG. 16C schematically depicts the rotary unit of FIG. 16A from a side view. FIG. 16D schematically shows a sectional view of the rotary unit of FIG. 16A. FIG. 16E schematically illustrates a planetary gear component from a front side view according to one embodiment of the invention. FIG. 16F schematically illustrates the planetary gear component of FIG. 16E from a side view. FIG. 16G schematically shows an exploded side view of a gear structure according to one embodiment of the invention. FIG. 16H schematically depicts the gear structure of FIG. 16G from a side view. FIG. 16I schematically shows the gear structure of FIG. 16H from a rear side view. FIG. 16J schematically shows the gear structure of FIG. 16H from a front side view. FIG. 16K schematically illustrates a gear structure prior to assembly with another gear structure from a side view according to one embodiment of the invention. FIG. 16L schematically shows an assembly that includes two gear structures from a side view according to one embodiment of the invention. FIG. 16M schematically shows an exploded view of the rotary unit of FIG. 16A with the gear structure of FIG. 16G from a side view according to one embodiment of the invention. FIG. 16N schematically shows the rotary unit of FIG. 16A with the gear structure of FIG. 16G from a front side view. FIG. 16O schematically shows the rotary unit of FIG. 16A with the gear structure of FIG. 16G from a rear side view. FIG. 16P schematically shows the rotary unit of FIG. 16A with the gear structure of FIG. 16G from a side view. FIG. 16Q schematically shows a sectional view of the rotary unit of FIG. 16A with the gear structure of FIG. 16G.

FIG. 17A schematically depicts rotary units and a shaft from side elevational views prior to assembly according to one embodiment of the invention. FIG. 17B schematically illustrates the rotary units and the shaft from FIG. 17A from side elevational views in an assembled format.

FIG. 18A schematically shows rotary units prior to assembly of a rotary mechanism from side views according to one embodiment of the invention. FIG. 18B schematically shows a partially assembled rotary mechanism with the rotary units of FIG. 18A from side views. FIG. 18C schematically illustrates a rotary mechanism that includes the rotary units of FIG. 18A from a side view.

FIG. 19A schematically illustrates a rotary mechanism that includes the rotary unit of FIG. 9A from a sectional view prior to assembly according to one embodiment of the invention. FIG. 19B schematically depicts the rotary mechanism of FIG. 19A from a sectional view following assembly. FIG. 19C schematically shows a portion of a rotary mechanism that includes the rotary unit of FIG. 9A with implements from a side view according to one embodiment of the invention.

FIG. 20A schematically illustrates a positioning component of a rotary mechanism from a side view according to one embodiment of the invention. FIG. 20B schematically depicts a portion of a rotary mechanism that includes the rotational component of FIG. 13A from a side view according to one embodiment of the invention. FIG. 20C schematically depicts a portion of a rotary mechanism that includes the rotational component of FIG. 13A and gear component of FIG. 13D from a side view according to one embodiment of the invention. FIG. 20D schematically shows the portion of the rotary mechanism of FIG. 20B from a sectional view. FIG. 20E schematically depicts the positioning component of FIG. 20A from a side view. FIG. 20F schematically shows the positioning component of FIG. 20A with a drive mechanism from a side view. FIG. 20G schematically illustrates a positioning component of a rotary mechanism from a side view according to one embodiment of the invention. FIG. 20H schematically illustrates a rotary mechanism that includes the rotational component of FIG. 13A from a side view according to one embodiment of the invention. FIG. 20I schematically shows the rotary mechanism of FIG. 20H from a sectional view. FIG. 20J schematically shows the rotary mechanism of FIG. 20H from a front side view. FIG. 20K schematically shows the rotary mechanism of FIG. 20H from a rear side view. FIG. 20L schematically depicts a portion of a drive mechanism from a side view according to one embodiment of the invention. FIG. 20M schematically depicts a portion of a drive mechanism from a side view according to one embodiment of the invention. FIG. 20N schematically depicts the portion of the drive mechanism of FIG. 20M without a motor from a side view. FIG. 20O schematically depicts the portion of the drive mechanism of FIG. 20M from a side view.

FIG. 21A schematically illustrates a rotary mechanism that includes the rotary unit of FIG. 14A from a sectional view prior to assembly according to one embodiment of the invention. FIG. 21B schematically depicts the rotary mechanism of FIG. 21A from a sectional view following assembly. FIG. 21C schematically shows the rotary of FIG. 21A from a side view. FIG. 21D schematically illustrates a rotary mechanism that includes the rotary unit of FIG. 14A with implements from a side view according to one embodiment of the invention. FIG. 21E schematically illustrates a rotary mechanism that includes the rotary unit of FIG. 14A with implements from a side view according to one embodiment of the invention.

FIG. 22A schematically illustrates a gear structure from the rotary unit of FIG. 14A prior to assembly with another gear structure from a side view according to one embodiment of the invention. FIG. 22B schematically shows an assembly of multiple gear structures from a side view according to one embodiment of the invention. FIG. 22C schematically depicts the gear structure assembly of FIG. 22B from a rear side view. FIG. 22D schematically depicts the gear structure assembly of FIG. 22B from a front side view. FIG. 22E schematically shows a rotary mechanism that includes the gear structure assembly of FIG. 22B from a sectional view according to one embodiment of the invention. FIG. 22F schematically shows a rotary mechanism that includes the gear structure assembly of FIG. 22B from a side view according to one embodiment of the invention.

FIG. 23A schematically depicts a rotational or rotary mechanism from an exploded side view according to one embodiment of the invention. FIG. 23B schematically depicts the rotational mechanism from FIG. 23A from a side view. FIG. 23C schematically depicts the rotational mechanism from FIG. 23A from an exploded sectional view. FIG. 23D schematically depicts the rotational mechanism from FIG. 23A from a sectional side view. FIG. 23E schematically shows a portion of a drive mechanism component from a front side view according to one embodiment of the invention. FIG. 23F schematically shows the portion of the drive mechanism component of FIG. 23E from a rear side view. FIG. 23G schematically shows the portion of the drive mechanism component of FIG. 23E from a side view. FIG. 23H schematically shows the portion of the drive mechanism component of FIG. 23E from a sectional side view. FIG. 23I schematically shows an exploded side view of a gear structure according to one embodiment of the invention. FIG. 23J schematically depicts the gear structure from FIG. 23I from a rear side view. FIG. 23K schematically depicts the gear structure from FIG. 23I from a side view. FIG. 23L schematically depicts the gear structure from FIG. 23I from a front side view. FIG. 23M schematically shows an exploded side view of the drive mechanism component of FIG. 23E and the gear structure of FIG. 23I according to one embodiment of the invention. FIG. 23N schematically shows an exploded sectional side view of the drive mechanism component of FIG. 23E and the gear structure of FIG. 23I according to one embodiment of the invention. FIG. 23O schematically depicts the drive mechanism component of FIG. 23E and the gear structure of FIG. 23I from a side view. FIG. 23P schematically depicts the drive mechanism component of FIG. 23E and the gear structure of FIG. 23I from sectional side view. FIG. 23Q schematically depicts an exploded side view of the rotational mechanism from FIG. 23B and the portion of the drive mechanism component of FIG. 23E according to one embodiment of the invention. FIG. 23R schematically depicts an exploded side sectional view of the rotational mechanism from FIG. 23B and the portion of the drive mechanism component of FIG. 23E according to one embodiment of the invention.

FIG. 24A schematically illustrates a partially exploded view of a tooth brushing device according to one embodiment of the invention. FIG. 24B schematically shows an assembled tooth brushing device from FIG. 24A from a side view. FIG. 24C schematically depicts the tooth brushing device of FIG. 24B from a top side view. FIG. 24D schematically depicts a rotary mechanism from the tooth brushing device of FIG. 24B from a side view.

FIG. 25A schematically shows a rotary mechanism for a tooth brushing device from a side view according to one embodiment of the invention. FIG. 25B schematically depicts a toothbrush head component that includes the rotary mechanism of FIG. 25A from a side view according to one embodiment of the invention.

FIG. 26 schematically illustrates a cleaning device from a side view according to one embodiment of the invention.

FIGS. 27 A-G schematically illustrate rotary units or components thereof from various views according to one exemplary embodiment of the invention. FIG. 27A schematically shows a rotational component from a front side view according to one embodiment of the invention. FIG. 27B schematically shows the rotational component from FIG. 27A from a side sectional view. FIG. 27C schematically depicts the rotational component from FIG. 27A from a side view. FIG. 27D schematically depicts the rotational component from FIG. 27A from a side view with a surface including implements. FIG. 27E schematically shows the rotational component from FIG. 27D from a front side view. FIG. 27F schematically shows a rotary unit that includes the rotational component from FIG. 27A and first and third gear components from a front side view according to one exemplary embodiment of the invention. FIG. 27G schematically shows a rotary unit that includes the rotational component from FIG. 27A and a second gear component from a front side view according to one exemplary embodiment of the invention.

FIGS. 28 A-I schematically illustrate a rotary mechanism or components thereof from various views according to one exemplary embodiment of the invention. FIG. 28A schematically shows a rotary mechanism from a front side view according to one embodiment of the invention.

FIGS. 29 A-C schematically illustrate a rotary mechanism or components thereof from various views according to one exemplary embodiment of the invention. FIG. 29A schematically shows portions of a rotational component prior to assembly from a side view. FIG. 29B schematically depicts a rotary mechanism that includes the rotational component from FIG. 29A prior to assembly from a front side view. FIG. 29C schematically depicts the rotary mechanism from FIG. 29B from a side view.

FIGS. 30A and B schematically show gear and drive mechanism components prior to and following assembly, respectively, according to one exemplary embodiment of the invention.

FIGS. 31A and B schematically show gear and drive mechanism components prior to and following assembly, respectively, according to one exemplary embodiment of the invention.

FIG. 32A schematically shows a detailed front side view of a drive mechanism component receiving area according to one embodiment of the invention.

FIG. 32B schematically shows a detailed front side view of a drive mechanism portion configured to be received by the drive mechanism component receiving area from FIG. 32A according to one embodiment of the invention.

FIG. 33 schematically shows a rotary mechanism prior to assembly from a side view according to one embodiment of the invention.

FIGS. 34 A-C schematically depict a tooth brushing device or components thereof from various views according to one exemplary embodiment of the invention. FIG. 34A schematically shows a rotary mechanism and drive mechanism components from a side view according to one exemplary embodiment of the invention. FIG. 34B schematically illustrates a tooth brushing device that includes the rotary mechanism and drive mechanism components from FIG. 34A from a partially transparent side view. FIG. 34C schematically shows a tooth brushing device that includes the rotary mechanism and drive mechanism components from FIG. 34A from a side view.

FIGS. 35 A-F schematically show a rotary mechanism or components thereof from various views according to one exemplary embodiment of the invention. FIG. 35D schematically shows the rotary mechanism from FIG. 35C from a front side view. FIG. 35E schematically shows the rotary mechanism from FIG. 35C from a side view. FIG. 35F schematically shows a drive mechanism positioning component from a front side view according to one exemplary embodiment of the invention.

FIGS. 36 A and B schematically show a tooth brushing device or components thereof from various views according to one exemplary embodiment of the invention. FIG. 36A schematically depicts a tooth brushing device from a partially transparent side view according to one exemplary embodiment of the invention. FIG. 36B schematically depicts the tooth brushing device from FIG. 36A from a side view.

FIG. 37A schematically illustrates a partially exploded view of a tooth brushing device according to one embodiment of the invention. FIG. 37B schematically shows an assembled tooth brushing device from FIG. 37A from a side view. FIG. 37C schematically depicts the tooth brushing device of FIG. 37B from a top side view. FIG. 37D schematically depicts a rotary mechanism from the tooth brushing device of FIG. 37B from a side view.

FIGS. 45A-J schematically illustrate tooth brushing devices or components thereof from various views according to certain embodiments of the invention. FIGS. 45A-C schematically show a rotational component from bottom, top, and side views, respectively. FIGS. 45D and E schematically show rotational components and drive mechanism components or portions thereof from bottom and top views according to one embodiment of the invention. FIG. 45F schematically illustrates the rotational components and drive mechanism components or portions thereof from FIG. 45E operably connected to motor and power source components from a side view. FIG. 45G schematically depict rotational components operably connected to drive mechanism components from a side view according to one embodiment of the invention. FIG. 45H schematically shows a tooth brushing device that includes the rotational components and drive mechanism components from FIG. 45F from a partially transparent side view according to one embodiment of the invention. FIGS. 45 I and J schematically show the tooth brushing device of FIG. 45H from side and top views, respectively.

FIGS. 46 A and B schematically show a tooth brushing device or components thereof from various views according to one exemplary embodiment of the invention.

FIGS. 47 A and B schematically illustrate a tooth brushing device or components thereof from various views according to one exemplary embodiment of the invention.

FIGS. 48A-F schematically illustrate a tooth brushing device or components thereof from various views according to one exemplary embodiment of the invention. FIG. 48A schematically depicts a tooth brushing device detached from a material container from a partially transparent side view according to one exemplary embodiment of the invention. FIG. 48B schematically depicts the tooth brushing device from FIG. 48A operably connected to the material container from a partially transparent side view. FIG. 48C schematically depicts the tooth brushing device from FIG. 48B from a side view. FIG. 48D schematically depicts portions of the tooth brushing device and material container from FIG. 48A from a partially transparent side view according to one exemplary embodiment of the invention. FIG. 48E schematically depicts portions of the tooth brushing device and material container from FIG. 48B from a partially transparent side view. FIG. 48F schematically shows the material container from FIG. 48A from a top view.

FIG. 49 schematically depicts portions of a tooth brushing device from a partially transparent side view according to one exemplary embodiment of the invention.

FIGS. 50 A and B schematically illustrate a tooth brushing device or components thereof from various views according to one exemplary embodiment of the invention. FIG. 50A schematically shows portions of a tooth brushing device detached from a material container from a partially transparent side view according to one exemplary embodiment of the invention. FIG. 50B schematically shows the material container from FIG. 50A from a top view.

FIG. 51 schematically shows a head portion of a tooth brushing device from a side view according to one exemplary embodiment of the invention.

FIGS. 52A-C schematically illustrate a sanitizing component from various views according to one exemplary embodiment of the invention. FIG. 52A schematically shows a head portion of a toothbrushing device being positioned relative to a sanitizing component from a side view. FIG. 52B schematically shows a head portion of a toothbrushing device positioned relative to the sanitizing component from FIG. 52A from a partially transparent side view. FIG. 52C schematically depicts the head portion of a toothbrushing device and sanitizing component from FIG. 52B from a top view.

FIG. 53 schematically shows a head portion of a toothbrushing device positioned relative to a sanitizing component from a partially transparent side view according to one exemplary embodiment of the invention.

FIG. 54 schematically shows a head portion of a toothbrushing device positioned relative to a sanitizing component from a partially transparent side view according to one exemplary embodiment of the invention.

FIGS. 55A-C schematically illustrate a rotational component, or portions thereof, that include at least one resilient coupling from side views according to one exemplary embodiment of the invention. FIGS. 55 A and B are shown from partial sectional side views.

FIGS. 56A-C schematically illustrate a rotational component, or portions thereof, that include at least one resilient coupling from side views according to one exemplary embodiment of the invention. FIGS. 56 A and B are shown from partial sectional side views.

FIGS. 57A-C schematically illustrate a rotational component, or portions thereof, that include at least one resilient coupling from side views according to one exemplary embodiment of the invention. FIGS. 57 A and B are shown from partial sectional side views.

FIGS. 58A-C schematically illustrate a rotational component, or portions thereof, that include at least one resilient coupling from side views according to one exemplary embodiment of the invention.

FIGS. 59A-C schematically illustrate a rotational component, or portions thereof, that include at least one resilient coupling from side views according to one exemplary embodiment of the invention.

FIGS. 60A-D schematically illustrate a rotational component, or portions thereof, that include at least one resilient coupling from side views according to one exemplary embodiment of the invention.

FIGS. 61A-D schematically illustrate a rotational component, or portions thereof, that include at least one resilient coupling from side views according to one exemplary embodiment of the invention.

FIGS. 62A-D schematically illustrate a rotational component, or portions thereof, that include at least one resilient coupling from side views according to one exemplary embodiment of the invention.

FIGS. 63A-D schematically illustrate a rotational component, or portions thereof, that include at least one resilient coupling from side views according to one exemplary embodiment of the invention.

FIGS. 64A-E schematically illustrate a rotational component, or portions thereof, that include at least one resilient coupling from side views according to one exemplary embodiment of the invention.

FIG. 72 schematically shows a tooth brushing device that includes rotational components having resilient couplings from a side view according to one embodiment of the invention.

FIG. 73 schematically shows a handheld device that includes rotational components having resilient couplings from a side view according to one embodiment of the invention.

FIG. 74A schematically illustrates a cleaning device that includes rotational components having resilient couplings from a sectional view according to one embodiment of the invention.

FIG. 74B schematically illustrates the cleaning device of FIG. 74A from a side view.

FIG. 75 schematically illustrates a rotor tiller that includes rotational components having resilient couplings from a front elevational view according to one embodiment of the invention.

FIG. 76A schematically illustrates a vehicle that includes rotational components having resilient couplings from a side elevational view according to one embodiment of the invention.

FIG. 76B schematically illustrates a vehicle that includes rotational components having resilient couplings from a side elevational view according to one embodiment of the invention.

FIG. 77A schematically illustrates a hair cutting device that includes rotational components having resilient couplings from a partial cross-sectional view according to one embodiment of the invention.

FIG. 77B schematically illustrates the rotational components of FIG. 77A positioned in a housing of the hair cutting device prior to placing a removable structure in an opening of the housing from side elevational views according to one embodiment of the invention.

FIG. 77C schematically illustrates the hair cutting device from FIG. 77B with the removable structure positioned in the opening of the housing from a side elevational view according to one embodiment of the invention.

DETAILED DESCRIPTION

I. Introduction

Figure 23S:
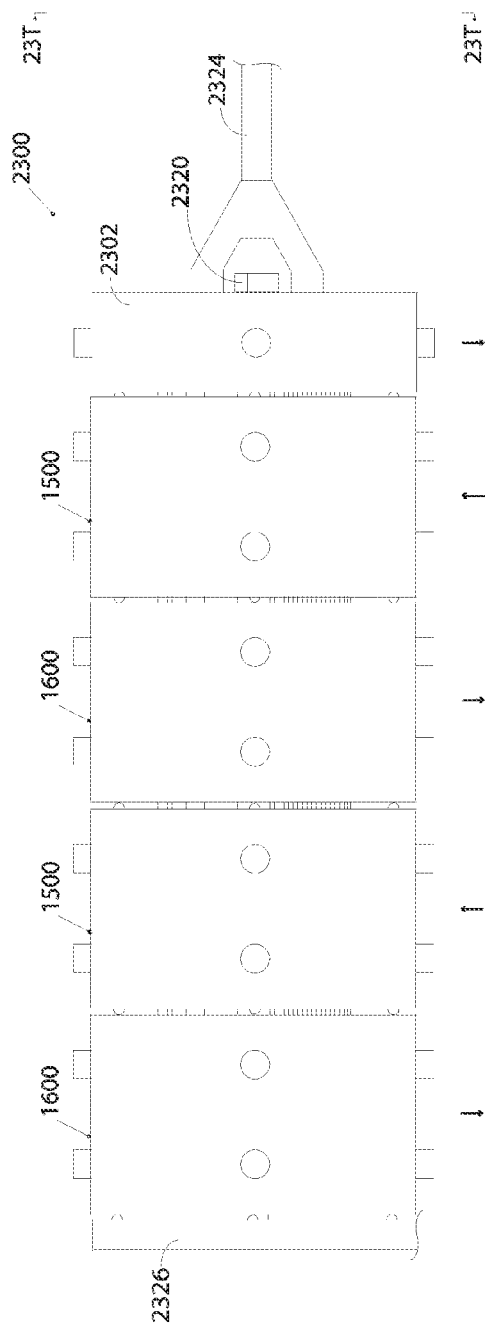
FIG. 23S schematically depicts a side view of the rotational mechanism from FIG. 23B and the portion of the drive mechanism component of FIG. 23E according to one embodiment of the invention.

Before describing the invention in detail, it is to be understood that this invention is not limited to particular methods, rotary units, rotary mechanisms, devices, or systems, which can vary. As used in this specification and the appended claims, the singular forms "a," "an," and "the" also include plural referents unless the context clearly provides otherwise. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the invention, the following terminology, and grammatical variants thereof, will be used in accordance with the definitions set forth below.

The term "coaxially positioned" refers to objects that are positioned relative to one another such that they can rotate about a substantially coincident axis.

The term "fixed position" refers to objects that are positioned relative to one another such that they do not move separately from one another. In some embodiments, for example, gear components (e.g., sun gear components) are attached (e.g., integrally fabricated, bonded, welded, adhered, or the like) to rotational components, such that when the rotational components move in one direction, the gear components move in the same direction as the rotational components.

The term "counter-rotate" or "contra-rotate" refers to objects that rotate in opposite directions relative to one another. In some embodiments, for example, rotary mechanisms include rotational components that are configured to rotate in opposite directions.

The term "communicate" refers to the direct or indirect transfer or transmission, and/or capability of directly or indirectly transferring or transmitting, something at least from one thing to another thing. In some embodiments, for example, devices include housings having openings through which hair, finger nails, or the like can be transferred to contact implements within housing cavities of the devices.

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate. The representative embodiments described herein are intended to illustrate, but not to limit, the invention. Essentially any combination of components or portions thereof described herein are optionally utilized or adapted for use together in certain embodiments.

II. Exemplary Rotary Units

FIGS. 1 A-H schematically show a rotary unit or components thereof according to one embodiment of the invention. As shown, rotary unit 100 includes rotational component 102, which includes first gear component 104 disposed on a first side of rotational component 102 (e.g., in an inner region of the first side) and second gear component 106 disposed on a second side of rotational component 102 (e.g., in an outer region of the second side). As shown, the first and second sides substantially oppose one another. Gear components used with the rotary units, rotary mechanisms, and other applications of the invention typically include gear teeth. Any operable gear tooth configuration and/or type are optionally used in the rotary units, rotary mechanisms and applications of the invention. Second gear component 106 substantially defines gear structure receiving area 108, which is configured to receive gear structure 110. Gear structure 110 includes support component 112 and third gear components 114. Third gear components 114 are configured to operably engage second gear component 106 such that when third gear components 114 rotate in a first direction, second gear component 106 and rotational component 102 also rotate the first direction. Third gear components 114 are configured to operably engage other gear components, such as a first gear component of another rotary unit such that when the other gear components rotate in a second direction, third gear components 114, second gear component 106, and rotational component 102 all rotate in the first direction. Rotary unit 100 also includes retaining mechanism 116 (shown as a wall or lip in this exemplary embodiment) that is structured to retain gear structure 110 at least partially in gear structure receiving area 108. As further shown in FIG. 1I, for example, in some embodiments during rotary unit assembly retaining mechanism 116 is attached to rotational component 102, once gear structure 110 is positioned in gear structure receiving area 108, via attachment components 118 (e.g., which clip into corresponding notches (not within view) in rotational component 102 in this representative embodiment).

Rotary unit 100 also includes implements 120 shown as beads that can be used, for example, as part of a massaging device or the like. Essentially any implement (e.g., type(s) and/or number on a given rotational component, etc.) is optionally adapted for use with the rotary units of the present invention, e.g., depending on the intended application of a given rotary unit. Representative implements that are optionally used include one or more of, e.g., a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, a post, or the like. Some exemplary implements 200-210 are also illustrated from side elevational views in, e.g., FIGS. 2A-F.

In addition, rotary unit 100 also includes drive mechanism component receiving area 122 (shown as a hole disposed through rotational component 102) that is configured to receive a drive mechanism component, such as a drive shaft or a portion thereof. Other exemplary drive mechanism components are described herein or otherwise known in the art.

FIGS. 3 A-G schematically illustrate a rotary unit or components thereof according to one embodiment of the invention. As shown, rotary unit 300 includes rotational component 302, which includes first gear component 304 extending from a first side, and second gear component 306 on a second side and substantially defining gear structure receiving area 308. Rotary unit 300 also includes gear structure 310, which includes third gear components 312 rotatably coupled to support component 314. As also shown, gear structure 310 includes hole 316 that is structured to align with drive mechanism component receiving area 318 of rotational component 302, e.g., to receive a drive mechanism component, such as a drive shaft about which gear structure 310 and rotational component 302 rotate.

Rotary unit 300 also includes a retaining mechanism that is configured to retain gear structure 310 in position relative to rotational component 302 such that the components can operably engage one another during operation. The retaining mechanism of rotary unit 300 includes groove or track 320 disposed approximately around gear structure receiving area 308 in rotational component 302. In addition, the retaining mechanism also includes projections 322 of gear structure 310 that insert into groove or track 320 such that gear structure 310 is retained and rotates within gear structure receiving area 308.

In some embodiments, the rotational components of the rotary units of the invention include implements that are configured to effect the movement of one or more other components (e.g., propeller components or the like) when the rotational components rotate and the implements operably engage the other components. To illustrate, rotational component 302 of rotary unit 300 also includes gear component 324 that is configured to operably engage other gear components of other components, e.g., to effect rotation of those components when rotational component 302 rotates.

FIGS. 4 A-G schematically show another exemplary embodiment of a rotary unit of the invention. As shown, rotary unit 400 includes rotational component 402 that includes first and second surfaces that substantially oppose one another. First gear component 404 is disposed on the first surface of rotational component 402 and is configured to operably engage third gear components of another rotary unit. Second gear component 406 is disposed on the second surface of rotational component 402 and substantially defines gear structure receiving area or cavity 408.

Rotary unit 400 also include gear structure 410, which includes support structure 412 and third gear components 414 rotatably coupled to support structure 412. Rotary unit 400 also includes a retaining mechanism formed, in part, by groove or track 416 formed in rotational component 402. Circular projection 418 disposed on support structure 412 of gear structure 410 is configured to fit within groove or track 416 such that gear structure 410 is retained, yet permitted to rotate, within gear structure receiving area 408. As also shown, rotary unit 400 also includes implements 420 (shown as blades) extending from a surface of rotational component 402.

FIGS. 5 A and B schematically illustrate a rotary unit according to another exemplary embodiment of the invention. As shown, rotary unit 500 includes rotational component 502. First gear component 504 extends from a first side of rotational component 502, while gear structure 506 engages a second gear component in a gear structure receiving area on a second side of rotational component 502 and partially extends from the gear structure receiving area. Gear structure 506 includes third gear components 508 rotatably coupled to support structure 510. Rotary unit 500 also includes a retaining mechanism formed, in part, by groove or track 512 formed in the gear structure receiving area of rotational component 502. Circular projection 514 disposed on support structure 510 of gear structure 506 is configured to fit within groove or track 512 such that gear structure 506 is retained, yet permitted to rotate, within the gear structure receiving area of rotational component 502. First gear component 504 is configured to engage one or more third gear components of another rotary unit. Third gear components 508 are configured to engage the second gear component in the gear structure receiving area and a first gear component of another rotary unit.

FIGS. 6 A-G schematically show a rotary unit or components thereof according to another representative embodiment of the invention. As shown, rotary unit 600 includes rotational component 602. Rotational component 602 includes first gear component 604 on a first side and second gear component 606 on a second side. Second gear component 606 substantially defines a gear structure receiving area of rotational component 602. Rotary unit 600 also includes gear structure 608 disposed within the gear structure receiving area. Gear structure 608 includes third gear components 610 rotatably coupled to support component 612. Third gear components 610 are configured to operably engage second gear component 606 of rotational component 602 and the first gear component of another rotary unit or another gear component, such as a component of a drive mechanism or the like. Gear structure 608 also includes hole or aperture 614, which is structured to align with drive mechanism component receiving area 616 of rotational component 602, e.g., to receive a drive mechanism component, such as a drive shaft about which gear structure 608 and rotational component 602 rotate. Rotary unit 600 also includes a retaining mechanism that is configured to retain and permit gear structure 608 to rotate within the gear structure receiving area of rotational component 602. In particular, support component 612 of gear structure 608 includes partially circular indentation 618 and rotational component 602 comprises projection 620 (e.g., an elevated circular track or the like). Projection 620 is configured to at least partially fit and move within partially circular indentation 618 to retain gear structure 608 at least partially within the gear structure receiving area when second gear component 606 and third gear components 610 operably engage one another. In some embodiments, gear structures comprise projections, such as projection 620 and rotational components comprise the substantially or partially circular indentation (e.g., a circular track or groove structured to receive the projection).

Rotary unit 600 also includes implements 622 that are rotatably coupled to rotational component 602. As shown, rotatably coupled implements 622 include gear components 624 that are configured to operably engage a corresponding gear component on a neighboring rotary unit when the neighboring rotary unit is disposed suitably proximal to rotary unit 600. In these embodiments, during operation, as neighboring rotary units counter-rotate relative to one another, rotatably coupled implements, such as implements 622 (e.g., shown as bristles suitable for a toothbrush, household cleaning device, or the like) also rotate. To further illustrate, rotary unit 600 includes gear component 626 that is configured to operably engage rotatably coupled implements disposed on a neighboring rotary unit.

FIGS. 7A-C schematically show a rotary unit according to one embodiment of the invention. As shown, rotary unit 700 includes rotational component 702, which includes first gear component 704 on a first side. Rotary unit 700 also includes a gear structure 706 disposed and able to rotate within a gear structure receiving area of rotational component 702. Lip or wall 708 retains gear structure 706 in the gear structure receiving area. Rotary unit 700 also includes alignment components that are structured to align rotary units relative to one another, e.g., in a given device or other application. In particular, the first side of rotational component 702 includes circular groove 710, while the second side of rotational component 702 includes circular ridge 712. Circular groove 710 is configured to receive a circular ridge (e.g., circular ridge 812) of another rotary unit (e.g., rotary unit 800), which circular ridge is configured to rotate within circular groove 710. In contrast, circular ridge 712 is configured to fit and rotate within a circular groove (e.g., circular groove 810) of another rotary unit (e.g., rotary unit 800). In some embodiments, the first side of rotational component 702 includes circular ridge 712, while the second side of rotational component 702 includes circular groove 710.

Rotary unit 700 also includes drive mechanism component receiving area 714 that is configured to receive a drive mechanism component (e.g., drive mechanism component 816 (shown as a drive shaft) of rotary unit 800). Rotational component 702 is configured to rotate about a drive mechanism component (e.g., drive mechanism component 816 of rotary unit 800), while first gear component 704 operably engages a gear component (e.g., a gear component of a gear structure) of another rotary unit e.g., a rotary unit, such as a rotary unit 800) and gear components of gear structure 706 operably engage another gear component (e.g., a first gear component) of yet another rotary unit (e.g., another rotary unit, such as another rotary unit 800). As also shown, a surface of rotational component 702 also includes multiple implements 716 (shown as razors or cutting edges) that are optionally used in hair cutting devices or other applications. Other implements are also optionally used.

FIGS. 8A-C schematically show a rotary unit according to one embodiment of the invention. As shown, rotary unit 800 includes rotational component 802, which includes first gear component 804 on a first side. Rotary unit 800 also includes a gear structure 806 disposed and able to rotate within a gear structure receiving area of rotational component 802. Lip or wall 808 retains gear structure 806 in the gear structure receiving area. Rotary unit 800 also includes alignment components that are structured to align rotary units relative to one another, e.g., in a given device or other application. In particular, the first side of rotational component 802 includes circular groove 810, while the second side of rotational component 802 includes circular ridge 812. Circular groove 810 is configured to receive a circular ridge (e.g., circular ridge 712) of another rotary unit (e.g., rotary unit 700), which circular ridge is configured to rotate within circular groove 810. In contrast, circular ridge 812 is configured to fit and rotate within a circular groove (e.g., circular groove 710) of another rotary unit (e.g., rotary unit 700). In some embodiments, the first side of rotational component 802 includes circular ridge 812, while the second side of rotational component 802 includes circular groove 810.

Rotary unit 800 also includes drive mechanism component receiving area 814 that is configured to receive a drive mechanism component (e.g., drive mechanism component 816 of a rotary unit 800). In the embodiment shown, drive mechanism component receiving area 814 includes a female threaded region that is configured to receive a male threaded region of drive mechanism component 816 of another rotary unit 800. As described above, another rotary unit (such as a rotary unit 700) is configured to fit between two rotary units 800 and rotate around a drive mechanism component 816 of one of the rotary units 800. As also shown, a surface of rotational component 802 also includes multiple implements 818 (shown as razors or cutting edges) that are optionally used in hair cutting devices or other applications. Other implements are also optionally used.

FIGS. 9A-L schematically depict an exemplary rotary unit or components thereof according to one embodiment of the invention. As shown, rotary unit 900 includes rotational component 902 that is configured to rotate around rotational axis 904. Rotational component 902 includes first surface 906 and second surface 908. First surface 906 includes gear component 910 (e.g., a sun gear component, etc.) that is configured to operably engage one or more gear components of at least a second rotational component (not shown) when rotational component 902 is disposed proximal to the second rotational component such that when the rotational component 902 rotates in a first direction, the second rotational component rotates in a second direction. In addition, second surface 908 comprises gear component 912 (e.g., a ring gear component, etc.) that is configured to operably engage one or more gear components (via gear components 914) of a third rotational (not shown) component when rotational component 902 is disposed proximal to the third rotational component such that when rotational component 902 rotates in the first direction, the second rotational component rotates in the second direction.

Gear structure 915 includes support component 917 and gear components 914 (e.g., planetary gear components or the like), which are rotatably coupled to support component 917. Support component 917 of gear structure 915 also includes friction reducing materials 919 (shown as elevated or pointed surface features) to reduce friction as rotational component 902 rotates relative to support component 917. As also shown in, for example, FIGS. 9J-L, surface 916 of the rotational component 902 comprises implement 918 (shown as a plurality of bristles), which surface 916 is configured to rotate substantially non-perpendicular to rotational axis 904. In this embodiment, for example, surface 916 of rotational component 902 is configured to rotate substantially parallel to rotational axis 904.

Rotary unit 900 also includes friction reducing materials 920 (shown as roller balls) disposed on first surface 906 of rotational component 902 to reduce friction as rotational component 902 rotates relative to another rotational component. In the embodiments in which friction reducing materials are utilized, essentially any friction reducing material is optionally adapted for use with the rotary units of the invention. Other exemplary embodiments include, for example, coatings (e.g., TEFLON®, etc.), lubricants, surface features, and/or the like. Rotational or rotary mechanisms typically include one or more rotary units 900. Exemplary rotational mechanisms are described further herein.

As further shown in FIG. 9I, for example, in some embodiments during rotary unit assembly retaining mechanism 922 is attached to another portion of rotational component 902, once gear structure 915 is positioned in a gear structure receiving area, via attachment components 924 (e.g., which clip into corresponding notches (not within view) in the portion of the rotational component that includes retaining mechanism 922 in this representative embodiment).

In addition, rotary unit 900 also includes drive mechanism component receiving area 925 (shown as a hole disposed through rotational component 902) that is configured to receive a drive mechanism component, such as a drive shaft or a portion thereof. Other exemplary drive mechanism components are described herein or otherwise known in the art.

FIGS. 10A-M schematically depict an exemplary rotary unit or components thereof according to one embodiment of the invention. As shown, rotary unit 1000 includes rotational component 1002 that is configured to rotate around rotational axis 1004. Rotational component 1002 includes first surface 1006 and second surface 1008. First surface 1006 includes gear component 1010 (e.g., a sun gear component, etc.) that is configured to operably engage one or more gear components of at least a second rotational component (not shown) when rotational component 1002 is disposed proximal to the second rotational component such that when the rotational component 1002 rotates in a first direction, the second rotational component rotates in a second direction. In addition, second surface 1008 comprises gear component 1012 (e.g., a ring gear component, etc.) that is configured to operably engage one or more gear components (via gear components 1014) of a third rotational (not shown) component when rotational component 1002 is disposed proximal to the third rotational component such that when rotational component 1002 rotates in the first direction, the third rotational component rotates in the second direction (e.g., in the same direction as the second rotational component).

Gear structure 1015 includes support component 1017 and gear components 1014 (e.g., planetary gear components or the like), which are rotatably coupled to support component 1017. Support component 1017 of gear structure 1015 also includes friction reducing materials 1019 (shown as elevated or pointed surface features) to reduce friction as rotational component 1002 rotates relative to support component 1017. As also shown in, for example, FIGS. 10K-M, surface 1016 of the rotational component 1002 comprises implement 1018 (shown as a plurality of bristles), which surface 1016 is configured to rotate substantially non-perpendicular to rotational axis 1004. In this embodiment, for example, surface 1016 of rotational component 1002 is configured to rotate substantially parallel to rotational axis 1004.

Rotary unit 1000 also includes friction reducing materials 1020 (shown as elevated surface features) disposed on first surface 1006 of rotational component 1002 to reduce friction as rotational component 1002 rotates relative to another rotational component. In the embodiments in which friction reducing materials are utilized, essentially any friction reducing material is optionally adapted for use with the rotary units of the invention. Other exemplary embodiments include, for example, coatings (e.g., TEFLON®, etc.), lubricants, surface features, and/or the like. In some embodiments of the rotary units of the invention, friction reducing materials are not utilized. Rotational mechanisms typically include one or more rotary units 1000. Exemplary rotational or rotary mechanisms are described further herein.

In addition, rotary unit 1000 also includes drive mechanism component receiving area 1024 (shown as a hole disposed through rotational component 1002) that is configured to receive a drive mechanism component, such as a drive shaft or a portion thereof. Other exemplary drive mechanism components are described herein or otherwise known in the art.

To further illustrate, FIGS. 11A-G schematically show a rotary unit or components thereof according to an exemplary embodiment of the invention. As shown, rotary unit 1100 includes rotational component 1102 that is configured to rotate around rotational axis 1104. Rotational component 1102 includes first surface 1106 and second surface 1108. First surface 1106 includes gear component 1110 (e.g., a sun gear component, etc.) that is configured to operably engage one or more gear components (via gear components 1114) of at least a second rotational component (not shown) when rotational component 1102 is disposed proximal to the second rotational component such that when the rotational component 1102 rotates in a first direction, the second rotational component rotates in a second direction. In addition, second surface 1108 comprises gear component 1112 (e.g., a ring gear component, etc.) that is configured to operably engage one or more gear components of a third rotational (not shown) component when rotational component 1102 is disposed proximal to the third rotational component such that when rotational component 1102 rotates in the first direction, the third rotational component rotates in the second direction (e.g., in the same direction as the second rotational component).

Gear structure 1115 includes support component 1117 and gear components 1114 (e.g., planetary gear components or the like), which are rotatably coupled to support component 1117. Support component 1117 of gear structure 1115 also includes friction reducing materials 1119 (shown as elevated or pointed surface features) to reduce friction as rotational component 1102 rotates relative to support component 1117. As also shown in, for example, FIGS. 11E-G, surface 1116 of the rotational component 1102 comprises implement 1118 (shown as a plurality of bristles in this exemplary embodiment), which surface 1116 is configured to rotate substantially non-perpendicular to rotational axis 1104. In this embodiment, for example, surface 1116 of rotational component 1102 is configured to rotate substantially parallel to rotational axis 1104. Rotational mechanisms typically include one or more rotary units 1100. Exemplary rotational or rotary mechanisms are described further herein.

In addition, rotary unit 1100 also includes drive mechanism component receiving area 1124 (shown as a hole disposed through rotational component 1102) that is configured to receive a drive mechanism component, such as a drive shaft or a portion thereof. Other exemplary drive mechanism components are described herein or otherwise known in the art.

FIGS. 12A-F schematically show a rotary unit or components thereof according to an exemplary embodiment of the invention. As shown, rotary unit 1200 includes rotational component 1202 that includes gear component 1210 (e.g., a sun gear component, etc.) that is configured to operably engage one or more gear components of at least a second rotational component (not shown) when rotational component 1202 is disposed proximal to the second rotational component such that when the rotational component 1202 rotates in a first direction, the second rotational component rotates in a second direction. In addition, rotational component 1202 comprises gear component 1212 (e.g., a ring gear component, etc.) that is configured to operably engage one or more gear components (via gear components 1214) of a third rotational (not shown) component when rotational component 1202 is disposed proximal to the third rotational component such that when rotational component 1202 rotates in the first direction, the third rotational component rotates in the second direction. Rotational component 1202 is structured similar to rotational component 1002 described herein, but further includes recessed area 1203, which is described below.

Gear structure 1215 includes support component 1217 and gear components 1214 (e.g., planetary gear components or the like), which are rotatably coupled to support component 1217. Support component 1217 of gear structure 1215 also includes friction reducing materials 1219 (shown as elevated or pointed surface features) to reduce friction as rotational component 1202 rotates relative to support component 1217. As also shown, gear structure 1215 also includes retaining features 1220 that are structured to fit and move within recessed area 1203 when gear structure 1215 is disposed in the gear structure receiving area of rotational component 1202. Retaining features 1220 further align and retain gear structure 1215 relative to rotational component 1202. In some embodiments, retaining features 1220 are not included. Although not shown, rotary unit 1200 also typically includes one or more implements. Rotational or rotary mechanisms typically include one or more rotary units 1200. Exemplary rotational mechanisms are described further herein.

In addition, rotary unit 1200 also includes drive mechanism component receiving area 1224 (shown as a hole disposed through rotational component 1202) that is configured to receive a drive mechanism component, such as a drive shaft or a portion thereof. Other exemplary drive mechanism components are described herein or otherwise known in the art.

FIGS. 13A-E schematically show components of rotary unit according to one exemplary embodiment of the invention. As shown, the rotary unit includes rotational component 1302 and gear component 1304 (e.g., a planetary gear component or the like). Although not shown, rotational component 1302 typically includes one or more implements (e.g., gear components, bristles, prongs, blades, etc.). Rotational component 1302 includes gear component 1310 (e.g., a ring gear component, etc.) that is configured to operably engage or mesh with gear component 1304. Rotational mechanisms that include these components are described further herein.

FIGS. 14A-D schematically show a rotary unit or components thereof according to an exemplary embodiment of the invention. As shown, rotary unit 1400 includes rotational component 1402 that includes gear component 1410 (e.g., a sun gear component, etc.), gear component 1412 (e.g., a ring gear component, etc.), and gear structure receiving area 1413. Gear component 1410 substantially fixedly extends from first surface 1406 of rotational component 1402. Gear component 1410 is configured to operably engage or mesh with one or more other gear components of another rotary unit when gear component 1410 is disposed proximal to the other gear components. Gear component 1412 substantially fixedly extends from second surface 1408 of rotational component 1402. Gear component 1412 communicates with gear structure receiving area 1413. Gear structure receiving area 1413 is configured to receive gear structure 1415.

Gear structure 1415 includes support component 1417 and gear components 1414 (e.g., planetary gear components or the like), which are rotatably coupled to support component 1417. Gear components 1414 are configured to operably engage or mesh with one or more other gear components when gear components 1414 are disposed proximal to the other gear components. Rotational component 1402 is configured to rotate relative to support component 1417, which support component 1417 is substantially fixedly positioned when rotational component 1402 rotates relative to support component 1417. Gear components 1414 are configured to rotate relative to rotational component 1402. Gear structures that include support components 1417 are described further herein. Although not shown, rotary unit 1400 also typically includes one or more implements. Rotational or rotary mechanisms typically include one or more rotary units 1400. Exemplary rotational mechanisms are described further herein.

FIGS. 15A-D schematically illustrate a rotary unit according to one embodiment of the invention. As shown, rotary unit 1500 includes rotational component 1502 that includes first sun gear component 1504 and second sun gear component 1506 on first and second surfaces, respectively, of rotational component 1502, which substantially oppose one another. First sun gear component 1504 is configured to operably engage one or more gear components of at least a second rotational component (not shown) when rotational component 1502 is disposed proximal to the second rotational component such that when rotational component 1502 rotates in a first direction, the second rotational component rotates in a second direction. Second sun gear component 1506 is configured to operably engage one or more gear components of at least a third rotational component (not shown) when rotational component 1502 is disposed proximal to the third rotational component such that when rotational component 1502 rotates in the first direction, the third rotational component rotates in the second direction. Exemplary gears that are optionally adapted for use with the rotary units, rotational mechanisms, and related applications of the invention are also described in, e.g., Dudley, *Handbook of Practical Gear Design* (*Mechanical Engineering Series*), CRC Press, $1^{st}$ Ed. (1994) and Litvin and Fuentes, *Gear Geometry and Applied Theory*, Cambridge University Press; $2^{nd}$ Ed. (2004), which are both incorporated herein in their entirety for all purposes.

Rotary unit 1500 also includes hole 1508 disposed through rotational component 1502. Hole 1508 is configured to receive, e.g., a drive mechanism component (e.g., an axle, a shaft, a gear structure component, etc.) or a support component such that rotational component 1502 can rotate around the drive mechanism component, the support component, or the like. Rotational component 1502 also includes friction reducing materials 1510 (shown as elevated or pointed surface features) to reduce friction as rotational component 1502 rotates relative to, e.g., other rotational components. In addition, rotational component 1502 also includes implements 1512 on a surface of rotational component 1502 that is configured to rotate substantially non-perpendicular to a rotational axis of rotary unit 1500. Essentially any implement is optionally adapted for use with rotary unit 1500, including the exemplary implements described herein. Rotary unit 1500 is typically included in a rotational or rotary mechanism, a device or the like. Exemplary rotational mechanisms that include rotary unit 1500 are described herein. In addition, representative devices that are optionally adapted to include rotary unit 1500 are also described herein.

FIGS. 16A-Q schematically illustrate a rotary unit or components thereof according to one embodiment of the invention. As shown, rotary unit 1600 includes rotational component 1602 that includes first ring gear component 1604 and second ring gear component 1606 on first and second surfaces, respectively, of rotational component 1602, which substantially oppose one another. First ring gear component 1604 is configured to operably engage one or more gear components of at least a second rotational component (not shown) when rotational component 1602 is disposed proximal to the second rotational component such that when rotational component 1602 rotates in a first direction, the second rotational component rotates in a second direction. Second ring gear component 1606 is configured to operably engage one or more gear components of at least a third rotational component (not shown) when rotational component 1602 is disposed proximal to the third rotational component such that when rotational component 1602 rotates in the first direction, the third rotational component rotates in the second direction.

Rotary unit 1600 also includes hole 1608 disposed through rotational component 1602. Hole 1608 is configured to receive, e.g., a drive mechanism component (e.g., an axle, a shaft, a gear structure component, etc.) or a support component such that rotational component 1602 can rotate around the drive mechanism component, the support component, or the like. Exemplary drive mechanism components and support components are described herein. Although not shown, rotational component 1602 optionally also includes friction reducing materials (e.g., elevated or pointed surface features, surface coatings, roller balls, etc.) to reduce friction as rotational component 1602 rotates relative to, e.g., other rotational components. In addition, rotational component 1602 also includes implements 1610 on a surface of rotational component 1602 that is configured to rotate substantially non-perpendicular to a rotational axis of rotary unit 1600. Essentially any implement is optionally adapted for use with rotary unit 1600, including the exemplary implements described herein. Rotary unit 1600 is typically included in a rotational or rotary mechanism, a device or the like. Exemplary rotational mechanisms that include rotary unit 1600 are described herein. In addition, representative devices that are optionally adapted to include rotary unit 1600 are also described herein.

In some embodiments, rotary unit 1600 also includes gear structure 1612, which includes support component 1614 and first planetary gear components 1616 and second planetary gear components 1618 rotatably coupled to support component 1614. As shown, first planetary gear components 1616 are configured to operably engage or mesh with first ring gear component 1604, second planetary gear components 1618 are configured to operably engage or mesh with second ring gear component 1606, and rotational component 1602 is configured to rotate relative to support component 1614, which is substantially fixedly positioned (e.g., in an assembled rotational mechanism, device, etc.) when rotational component 1602 rotates relative to support component 1614. As also shown, for example, in FIGS. 16 A and B, respectively, first ring gear component 1604 at least partially defines first gear structure receiving area 1605 and second ring gear component 1606 at least partially defines second gear structure receiving area 1607. First gear structure receiving area 1605 and second gear structure receiving area 1607 are configured to receive first portion 1622 and second portion 1624, respectively, of support component 1614 of gear structure 1612. First portion 1622 and second portion 1624 of support component 1614 of gear structure 1612 are described, e.g., further below.

FIG. 16G schematically shows an exploded side view of gear structure 1612 according to one embodiment of the invention. As shown, threaded region 1620 of first portion 1622 of support component 1614 inserts into a threaded region receiving area (not within view in FIG. 16G) of second portion 1624 of support component 1614 during assembly of gear structure 1612. In addition, first planetary gear components 1616 are rotatably coupled to second portion 1624 of support component 1614 via pronged retaining elements 1626 and second planetary gear components 1618 are rotatably coupled to first portion 1622 of support component 1614 via pronged retaining elements 1628 during assembly of gear structure 1612. As also shown, first portion 1622 and second portion 1624 of support component 1614 include friction reducing materials 1630 (shown as elevated or pointed surface features), e.g., to minimize friction when rotational component 1602 rotates relative to support component 1614 during operation of assembled rotary unit 1600. To further illustrate, FIG. 16M schematically shows an exploded view of rotary unit 1600 with first portion 1622 and second portion 1624 of support component 1614 of gear structure 1612 prior to assembly with rotational component 1602.

To further illustrate, FIG. 16K schematically illustrates gear structure 1612 prior to assembly with another gear structure 1612 from a side view according to one embodiment of the invention. As shown, during assembly, threaded region 1632 of one support component 1614 is inserted into threaded region receiving area 1634 of another support component 1614 such that the assembled support components 1614 are substantially fixedly positioned relative to one another, e.g., when rotational components 1602 of rotary units 1600 rotate relative to support components 1614. Essentially any attachment technique is optionally utilized to attach support components 1614 of gear structures 1612 to one another or first portion 1622 and second portion 1624 of support component 1614 to one another. Some exemplary techniques include, for example, bonding, welding, adhering, or the like. In some embodiments, multiple support components 1614 are fabricated as single integral part (e.g., as a molded part or the like).

FIGS. 27 A-G schematically illustrate rotary units or components thereof from various views according to one exemplary embodiment of the invention. As shown, rotary unit 4200 or rotary unit 4202 each include rotational component 4204, which includes gear component 4206 (e.g., a ring gear component) and surface 4208 that includes implements 4210. Rotational component 4204 is configured to rotate around rotational axis 4212. Surface 4208, which includes implements 4210 is configured to rotate substantially non-perpendicular to rotational axis 4212. In some of these embodiments, surface 4208 is configured to rotate substantially parallel to rotational axis 4212 of rotational component 4204. Rotary unit 4200 includes first gear component 4214 and third gear component 4216. First gear component 4214 operably engages (e.g., meshes with) gear component 4206 such that when first gear component 4214 rotates in a first direction, rotational component 4204 rotates in the first direction. Rotary unit 4202 includes second gear component 4218 operably engages (e.g., meshes with) gear component 4206 of rotational component 4204. Second gear component 4218 operably engages (e.g., meshes with) third gear component 4216 when rotational component 4204 of rotary unit 4200 is disposed proximal to (e.g., operably engages) rotational component 4204 of rotary unit 4202 such that when first gear component 4214 rotates in the first direction, the rotational component 4204 of rotary unit 4200 rotates in the first direction and second gear component 4218 and rotational component 4204 of rotary unit 4202 rotate in a second direction.

Rotational component 4204 also includes alignment component 4220 and alignment component receiving area 4222. Alignment component 4220 and alignment component receiving area 4222 are configured to align rotational component 4204 relative to other rotational components when the other rotational components are disposed proximal to rotational component 4202. For example, alignment component 4220 of rotational component 4204 is configured to be received by an alignment component receiving area of another rotational component, while alignment component receiving area 4222 of rotational component 4204 is configured to receive an alignment component of another rotational component.

The drive mechanism components or portions thereof of the rotary units of the invention include various embodiments. Rotary unit 4200, for example, includes drive mechanism component or portion thereof 4224 (e.g., shown as a shaft component), which operably engages first gear component 4214 and at least one other gear component (i.e., third gear component 4216 in this embodiment). Drive mechanism component or portion thereof 4224 is configured to effect rotation of first gear component 4214 and third gear component 4216. To further illustrate, rotary unit 4202 includes drive mechanism component or portion thereof 4226 (e.g., shown as a shaft component), which operably engages second gear component 4218. Drive mechanism components or portions thereof, including drive mechanism component receiving areas are described further herein.

FIGS. 55A-C schematically illustrate a rotational component, or portions thereof, that include at least one resilient coupling from side views according to one exemplary embodiment of the invention. FIGS. 55 A and B are shown from partial sectional side views. As shown, rotational component 5500 includes first portion 5502 and second portion 5504. Rotational component 5500 also includes resilient coupling 5506, which resiliently couples first portion 5502 and second portion 5504 to one another. Resilient coupling 5506 includes a positioning mechanism (post 5508 and post retainer 5510) that positions the first and second portions relative to one another within a range of motion (see, e.g., directional arrows in FIG. 55C). Resilient coupling 5506 also includes flexible prongs 5512, which resiliently position first portion 5502 relative to second portion 5504. Rotational component 5500 also includes gear component 5514 that is configured to mesh with one or more gear components of neighboring rotational components and/or drive mechanism components. In the embodiment shown, rotational component 5500 includes implements 5516 (shown as bristles) disposed on a surface that is configured to rotate substantially perpendicular to rotational axis 5517 of rotational component 5500. Exemplary implements and rotary mechanisms that are optionally adapted for use with rotational components are described herein. Rotational component 5500 also includes alignment component 5518 (shown as a peg in this embodiment) that align rotational component 5500 relative, e.g., to a housing or other component.

FIGS. 56A-C schematically illustrate a rotational component, or portions thereof, that include at least one resilient coupling from side views according to one exemplary embodiment of the invention. FIGS. 56 A and B are shown from partial sectional side views. As shown, rotational component 5600 includes first portion 5602 and second portion 5604. Rotational component 5600 also includes resilient coupling 5606, which resiliently couples first portion 5602 and second portion 5604 to one another. Resilient coupling 5606 includes a positioning mechanism (post 5608 and post retainer 5610) that positions the first and second portions relative to one another within a range of motion (see, e.g., directional arrows in FIG. 56C). Resilient coupling 5606 also includes spring mechanisms 5612, which resiliently position first portion 5602 relative to second portion 5604. Rotational component 5600 also includes gear component 5614 that is configured to mesh with one or more gear components of neighboring rotational components and/or drive mechanism components. In the embodiment shown, rotational component 5600 includes implements 5616 (shown as bristles) disposed on a surface that is configured to rotate substantially perpendicular to rotational axis 5617 of rotational component 5600. Exemplary implements and rotary mechanisms that are optionally adapted for use with rotational components are described herein. Rotational component 5600 also includes alignment component 5618 (shown as a peg in this embodiment) that align rotational component 5600 relative, e.g., to a housing or other component.

FIGS. 57A-C schematically illustrate a rotational component, or portions thereof, that include at least one resilient coupling from side views according to one exemplary embodiment of the invention. FIGS. 57 A and B are shown from partial sectional side views. As shown, rotational component 5700 includes first portion 5702 and second portion 5704. Rotational component 5700 also includes resilient coupling 5706, which resiliently couples first portion 5702 and second portion 5704 to one another. Resilient coupling 5706 includes a positioning mechanism (post 5708 and post retainer 5710) that positions the first and second portions relative to one another within a range of motion (see, e.g., directional arrows in FIG. 57C). Resilient coupling 5706 also includes flexible or elastomeric material 5712, which resiliently positions first portion 5702 relative to second portion 5704. Rotational component 5700 also includes gear component 5714 that is configured to mesh with one or more gear components of neighboring rotational components and/or drive mechanism components. In the embodiment shown, rotational component 5700 includes implements 5716 (shown as bristles) disposed on a surface that is configured to rotate substantially perpendicular to rotational axis 5717 of rotational component 5700. Exemplary implements and rotary mechanisms that are optionally adapted for use with rotational components are described herein. Rotational component 5700 also includes alignment component 5718 (shown as a peg in this embodiment) that align rotational component 5700 relative, e.g., to a housing or other component.

FIGS. 58A-C schematically illustrate a rotational component, or portions thereof, that include at least one resilient coupling from side views according to one exemplary embodiment of the invention. As shown, rotational component 5800 includes first portion 5802 and second portion 5804. Rotational component 5800 also includes resilient coupling 5806, which resiliently couples first portion 5802 and second portion 5804 to one another. Resilient coupling 5806 includes a positioning mechanism (shown as interlocking retainer components 5808 and 5812) that positions the first and second portions relative to one another within a range of motion (see, e.g., directional arrows in FIG. 58C). Resilient coupling 5806 also includes spring mechanisms 5810, which resiliently position first portion 5802 relative to second portion 5804. Rotational component 5800 also includes gear component 5814 that is configured to mesh with one or more gear components of neighboring rotational components and/or drive mechanism components. In the embodiment shown, rotational component 5800 includes implements 5816 (shown as bristles) disposed on a surface that is configured to rotate substantially perpendicular to rotational axis 5817 of rotational component 5800. Exemplary implements and rotary mechanisms that are optionally adapted for use with rotational components are described herein. Rotational component 5800 also includes alignment component 5818 (shown as a peg in this embodiment) that align rotational component 5800 relative, e.g., to a housing or other component.

FIGS. 59A-C schematically illustrate a rotational component, or portions thereof, that include at least one resilient coupling from side views according to one exemplary embodiment of the invention. As shown, rotational component 5900 includes first portion 5902 and second portion 5904. Rotational component 5900 also includes resilient coupling 5906, which resiliently couples first portion 5902 and second portion 5904 to one another. Resilient coupling 5906 includes material container component 5912 (e.g., a flexible bladder or the like that is at least partially filled with a fluidic (e.g., a gas, a liquid, etc.) and/or semi-fluidic (e.g., a gel, etc.) material) that resiliently positions the first and second portions relative to one another (see, e.g., directional arrows in FIG. 59C). Rotational component 5900 also includes gear component 5914 that is configured to mesh with one or more gear components of neighboring rotational components and/or drive mechanism components. In the embodiment shown, rotational component 5900 includes implements 5916 (shown as bristles) disposed on a surface that is configured to rotate substantially perpendicular to rotational axis 5917 of rotational component 5900. Exemplary implements and rotary mechanisms that are optionally adapted for use with rotational components are described herein. Rotational component 5900 also includes alignment component 5918 (shown as a peg in this embodiment) that align rotational component 5900 relative, e.g., to a housing or other component.

FIGS. 60A-D schematically illustrate a rotational component, or portions thereof, that include at least one resilient coupling from side views according to one exemplary embodiment of the invention. As shown, rotational component 6000 includes first portion 6002 and second portion 6004. FIGS. 60 A and B schematically depict first portion 6002 and second portion 6004 prior to assembly of rotational component 6000, while FIGS. 60 C and D schematically illustrate first portion 6002 and second portion 6004 following the assembly of rotational component 6000. Rotational component 6000 also includes a resilient coupling that resiliently couples first portion 6002 and second portion 6004 to one another. The resilient coupling includes a positioning mechanism (shown as retainer components 6008 and 6012) that positions the first and second portions relative to one another within a range of motion (see, e.g., directional arrows in FIG. 60D). The resilient coupling also includes flexible prongs 6010, which resiliently position first portion 6002 relative to second portion 6004. Rotational component 6000 also includes gear component 6014 that is configured to mesh with, e.g., one or more other gear components of rotational component 6000, one or more gear components of other rotational components and/or one or more gear components of drive mechanism components. In the embodiment shown, rotational component 6000 includes implements 6016 disposed on a surface that is configured to rotate substantially parallel to a rotational axis of rotational component 6000. Exemplary implements and rotary mechanisms that are optionally adapted for use with rotational components are described herein.

FIGS. 61A-D schematically illustrate a rotational component, or portions thereof, that include at least one resilient coupling from side views according to one exemplary embodiment of the invention. As shown, rotational component 6100 includes first portion 6102 and second portion 6104. FIGS. 61A and B schematically depict first portion 6102 and second portion 6104 prior to assembly of rotational component 6100, while FIGS. 61C and D schematically illustrate first portion 6102 and second portion 6104 following the assembly of rotational component 6100. Rotational component 6100 also includes a resilient coupling that resiliently couples first portion 6102 and second portion 6104 to one another. The resilient coupling includes a positioning mechanism (shown as retainer components 6110 and 6112) that positions the first and second portions relative to one another within a range of motion (see, e.g., directional arrows in FIG. 61D). The resilient coupling also includes spring mechanisms 6108, which resiliently position first portion 6102 relative to second portion 6104. Rotational component 6100 also includes gear component 6114 that is configured to mesh with, e.g., one or more other gear components of rotational component 6100, one or more gear components of other rotational components and/or one or more gear components of drive mechanism components. In the embodiment shown, rotational component 6100 includes implements 6116 disposed on a surface that is configured to rotate substantially parallel to a rotational axis of rotational component 6100. Exemplary implements and rotary mechanisms that are optionally adapted for use with rotational components are described herein.

FIGS. 62A-D schematically illustrate a rotational component, or portions thereof, that include at least one resilient coupling from side views according to one exemplary embodiment of the invention. As shown, rotational component 6200 includes first portion 6202 and second portion 6204. FIGS. 62 A and B schematically depict first portion 6202 and second portion 6204 prior to assembly of rotational component 6200, while FIGS. 62 C and D schematically illustrate first portion 6202 and second portion 6204 following the assembly of rotational component 6200. Rotational component 6200 also includes a resilient coupling that resiliently couples first portion 6202 and second portion 6204 to one another. The resilient coupling includes spring mechanisms 6208, which resiliently position first portion 6202 relative to second portion 6204 within a range of motion (see, e.g., directional arrows in FIG. 62D). Rotational component 6200 also includes gear component 6214 that is configured to mesh with, e.g., one or more gear components of other rotational components and/or drive mechanism components. In the embodiment shown, rotational component 6200 includes implements 6216 disposed on a surface that is configured to rotate substantially parallel to a rotational axis of rotational component 6200. Exemplary implements and rotary mechanisms that are optionally adapted for use with rotational components are described herein.

FIGS. 63A-D schematically illustrate a rotational component, or portions thereof, that include at least one resilient coupling from side views according to one exemplary embodiment of the invention. As shown, rotational component 6300 includes first portion 6302 and second portion 6304. FIGS. 63 A and B schematically depict first portion 6302 and second portion 6304 prior to assembly of rotational component 6300, while FIGS. 63 C and D schematically illustrate first portion 6302 and second portion 6304 following the assembly of rotational component 6300. Rotational component 6300 also includes a resilient coupling that resiliently couples first portion 6302 and second portion 6304 to one another. The resilient coupling includes a positioning mechanism (shown as retainer components 6310 and flexible prongs 6308) that resiliently position the first and second portions relative to one another within a range of motion (see, e.g., directional arrows in FIG. 63D). Rotational component 6300 also includes gear component 6314 that is configured to mesh with, e.g., one or more gear components of other rotational components and/or drive mechanism components. In the embodiment shown, rotational component 6300 includes implements 6316 disposed on a surface that is configured to rotate substantially parallel to a rotational axis of rotational component 6300. Exemplary implements and rotary mechanisms that are optionally adapted for use with rotational components are described herein.

FIGS. 64A-E schematically illustrate a rotational component, or portions thereof, that include at least one resilient coupling from side views according to one exemplary embodiment of the invention. As shown, rotational component 6400 includes first portion 6402 and second portion 6404. Rotational component 6400 also includes a resilient coupling, which resiliently couples first portion 6402 and second portion 6404 to one another. The resilient coupling includes material container component 6408 (e.g., a flexible bladder or the like that is at least partially filled with a fluidic (e.g., a gas, a liquid, etc.) and/or semi-fluidic (e.g., a gel, etc.) material) that resiliently positions the first and second portions relative to one another (see, e.g., directional arrows in FIG. 64E). FIGS. 64 A-C schematically depict first portion 6402, material container component 6408, and second portion 6404, respectively, prior to assembly of rotational component 6400, while FIGS. 64 D and E schematically illustrate first portion 6402, material container component 6408, and second portion 6404 following the assembly of rotational component 6400. Rotational component 6400 also includes gear component 6414 that is configured to mesh with, e.g., gear structure 6412 and/or drive mechanism components. In the embodiment shown, rotational component 6400 includes implements 6416 disposed on a surface that is configured to rotate substantially parallel to a rotational axis of rotational component 6400. Exemplary implements and rotary mechanisms that are optionally adapted for use with rotational components are described herein.

III. Exemplary Rotary Mechanisms

In certain embodiments, the invention provides rotary or rotational mechanisms that include two or more rotational components or rotary units (e.g., 2, 3, 4, 5, 6, 7, 8, 9, 10, 11, 12, 13, 14, 15, or more rotational components or rotary units). Rotary mechanisms also typically include at least one counter-rotational mechanism operably coupled to one or more of the rotational components. The counter-rotational mechanism is generally configured to effect substantially simultaneous counter-rotation of the rotational components relative to one another when movement of at least a portion of the counter-rotational mechanism is effected. Rotary mechanisms also typically include drive mechanisms operably coupled to the counter-rotational mechanism and/or rotational components. Drive mechanisms are typically configured to effect movement of at least the portion of the counter-rotational mechanisms such that the rotational components substantially simultaneously counter-rotate relative to one another. In some embodiments, for example, multiple rotary units are included as components (e.g., rotational components and counter-rotational mechanisms, etc.) of rotary mechanisms.

In some embodiments, rotary units are operably coupled to one another via one or more shafts. To illustrate one embodiment, FIG. 17A schematically depicts rotary units 100 and drive mechanism component 1702 (shown as a shaft) prior to assembly. As shown, gear component 1704 is fixedly coupled to shaft 1702 and is configured to operably engage third gear components 114 (not within view in FIGS. 17 A and B) of a rotary unit 100 in assembled rotary mechanism 1700. During assembly, shaft 1702 is inserted through drive mechanism component receiving areas 122 (shown as holes, e.g., in FIG. 1A) of rotary units 100 to operably couple rotary units 100 to one another. FIG. 17B schematically illustrates rotary units 100 and shaft 1702 following assembly. Suitable shafts include a variety of cross-sectional shapes (e.g., circular, oval, triangular, square, rectangular, polygonal, etc.). In some embodiments, a given shaft includes multiple cross-sectional shapes. In some of these embodiments, individual rotary units include drive mechanism component receiving areas (e.g., holes, apertures, etc.) that correspond to those different cross-sectional shapes. In some embodiments, for example, one member of a pair of neighboring rotary units includes a square hole that fits on a square cross-section of a shaft, while the other member of the pair includes a circular hole that fits on a circular cross-section of the shaft. In these embodiments, the rotary unit with the square hole typically rotates in a substantially fixed position relative to the shaft, whereas the rotary unit with the circular hole typically rotates substantially free or independent relative to the shaft.

Figure 65:
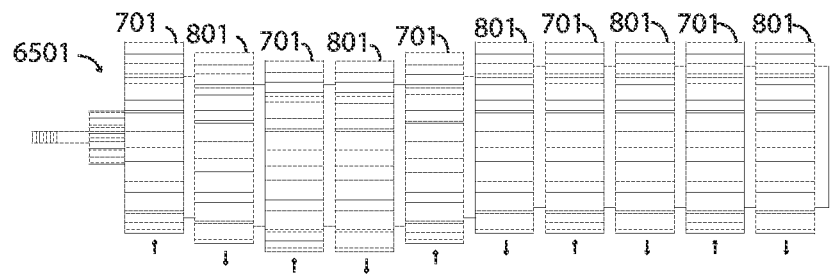
FIG. 65 schematically shows a rotary mechanism that includes rotational components having resilient couplings from a side view according to one exemplary embodiment of the invention.

To further illustrate, FIGS. 18 A-C schematically show rotary mechanism 1800 assembled from pairs of rotary units 700 and 800, which are both described further herein. More specifically, FIG. 18A schematically shows an individual pair of rotary units 700 and 800 prior to assembly of rotary mechanism 1800 from side views. FIG. 18B schematically shows partially assembled rotary mechanism 1800 with the rotary units of FIG. 18A from side views. FIG. 18C schematically illustrates rotary mechanism 1800 that includes multiple pairs of rotary units 700 and 800. FIG. 65 schematically shows rotary mechanism 6501 that includes rotational components 701 and 801 having resilient couplings see, e.g., directional arrows from a side view according to one exemplary embodiment of the invention.

In some embodiments, rotary units are operably coupled to one another via one or more shafts. To illustrate one embodiment, FIG. 19A schematically depicts rotary units 900, drive mechanism component 1902 (shown as a shaft), and cap component 1903 prior to assembly. As shown, gear component 1904 is fixedly coupled to shaft 1902 and is configured to operably engage or mesh with gear components 914 of a rotary unit 900 in assembled rotary mechanism 1900. During assembly, shaft 1902 is inserted through drive mechanism component receiving areas 925 (shown as a hole, e.g., in FIG. 9A) of rotary units 900 to operably couple rotary units 900 to one another. Shaft 1902 operably connects with cap component 1903 in assembled rotary mechanism 1900, e.g., to hold rotary units 900 in position relative to one another. FIG. 19B schematically illustrates rotary units 900, shaft 1902, and cap component 1903 following assembly of rotary mechanism 1900. The directional arrows in FIG. 19B schematically depict that neighboring pairs of rotary units 900 in rotary mechanism 1900 are configured to counter-rotate relative to one another. FIG. 19C schematically shows a portion of a rotary mechanism that includes rotary units 900 with implements 918.

Figure 68:
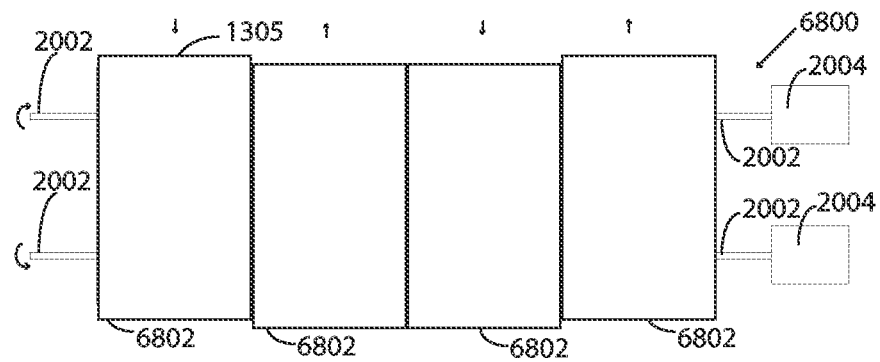
FIG. 68 schematically shows a rotary mechanism that includes rotational components having resilient couplings from a side view according to one exemplary embodiment of the invention.

FIGS. 20A-O schematically show a rotary mechanism or components thereof according to exemplary embodiments of the invention. As shown, rotary mechanism 2000 includes four rotary units that each include rotational component 1302 and gear component 1304. Rotary mechanism 2000 also includes a drive mechanism that includes shafts 2002 and motors 2004. Motors 2004 are configured to effect rotation of shafts 2002. As shown, the drive mechanism is configured to effect rotation of gear components 1304 such that rotational components 1302 of neighboring or adjacent pairs of rotary units rotate in opposite directions. See, e.g., the directional arrows in FIG. 20H, which schematically depict the counter-rotation of neighboring pairs of rotational components 1302. As shown, one shaft 2002 is operably connected to a first set of two non-neighboring gear components 1304, while the other shaft 2002 is operably connected to a second set of two non-neighboring gear components 1304 that is different from the first set of two non-neighboring of gear components 1304. The two shafts 2002 are configured to rotate in opposite directions. See, e.g., the directional arrows associated with shafts 2002 in FIGS. 20 H and I. As also shown, surfaces 1305 of rotational components 1302 are configured to rotate substantially non-perpendicular to a rotational axis of rotational components 1302 or rotational components 6802. FIG. 68 schematically shows rotary mechanism 6800 that includes rotational components 6802 having resilient couplings from a side view according to one exemplary embodiment of the invention.

Any suitable drive mechanism is optionally utilized with these rotary mechanisms. For example, FIG. 20L schematically depicts a portion of a drive mechanism from a side view. As shown, the drive mechanism includes motor 2004 (depicted as a dual shaft motor) that is configured to effect rotation of shafts 2002 in opposite directions via meshing pairs of gear components 2006. To further illustrate, FIGS. 20M-O schematically depict portions of a drive mechanism. As shown, motor 2004 is configured to effect rotation of shafts 2002 in opposite directions via a gear train that includes gear components 2008.

In addition, rotary mechanism 2000 also includes positioning component 2010 (shown as a frame structure) that is configured to position rotary units relative to one another. As shown, shafts 2002 are positioned relative to positioning component 2010 via mount brackets 2012, which permit rotation of shafts 2002. As also shown, positioning component 2010 also includes a plurality of friction reducing materials 2014 (shown as roller balls) disposed on a surface of positioning component 2010 to reduce friction as rotational components 1302 rotates relative to positioning component 2010. In the embodiments in which friction reducing materials are utilized, essentially any friction reducing material is optionally adapted for use with the rotary mechanisms of the invention. Other exemplary embodiments include, for example, coatings (e.g., TEFLON®, etc.), lubricants, surface features, and/or the like. FIG. 20G schematically depicts positioning component 2016 according to another exemplary embodiment.

Figure 66:
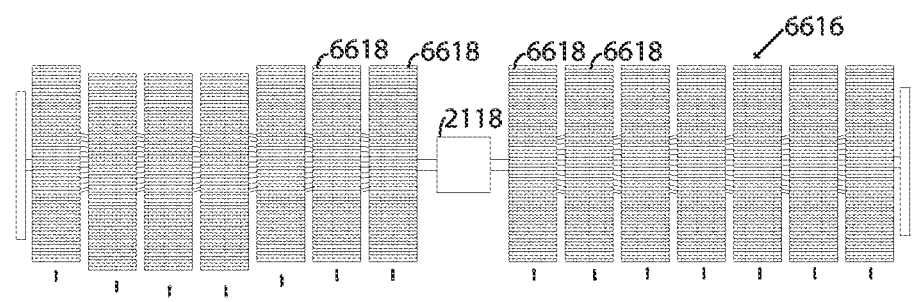
FIG. 66 schematically shows a rotary mechanism that includes rotational components having resilient couplings from a side view according to one exemplary embodiment of the invention.

FIGS. 21A-E schematically show rotary mechanisms or components thereof according to exemplary embodiments of the invention. As shown, rotary mechanism 2100 includes drive mechanism component 2102, which includes ring gear component 2104 and a gear structure. The gear structure includes support component 2106 and planetary gear components 2108 rotatably coupled to support component 2106. Planetary gear components 2108 are configured to operably engage ring gear component 2104 of drive mechanism component 2102 and gear component 1410 of rotary unit 1400. Drive mechanism component 2102 also includes motor 2110, which is configured to effect rotation of ring gear component 2104 via shaft 2112. Shaft 2112 is fixedly connected to ring gear component 2104. When ring gear component 2104 rotates, it effects the counter-rotation of neighboring pairs of rotary units 1400 relative to one another. See, e.g., the directional arrows associated with FIGS. 21B and C, which schematically depict the counter-rotation of neighboring pairs of rotary units 1400. As also shown, in assembled rotary mechanism 2100, support component 2106 is operably connected to support components 1417 of rotary units 1400 such that support component 2106 and support components 1417 are substantially fixedly positioned relative to one another when ring gear component 2104 effects the counter-rotation of neighboring pairs of rotary units 1400 relative to one another. Gear structures that include support components 1417 are described further herein. To further illustrate, FIG. 21D schematically depicts rotary mechanism 2114, which includes rotary units 1400 with implements 1418. In addition, FIG. 21E schematically illustrates rotary mechanism 2116, which includes rotary units 1400 with implements 1418 and dual shaft motor 2118. FIG. 66 schematically shows rotary mechanism 6616 that includes rotational components 6618 having resilient couplings (see, e.g., directional arrows) from a side view according to one exemplary embodiment of the invention.

The gear structures of the invention include various embodiments. To illustrate, FIG. 22A schematically illustrates gear structure 1415 prior to assembly with another gear structure 1415 from a side view according to one embodiment of the invention. As shown, gear structure 1415 includes support component 1417 and gear components 1414 (e.g., planetary gear components or the like), which are rotatably coupled to support component 1417. Gear components 1414 are configured to operably engage or mesh with one or more other gear components when gear components 1414 are disposed proximal to the other gear components. During assembly, threaded region 1429 of one support component 1417 is inserted into threaded region receiving area 1427 of another support component 1417 such that the assembled support components 1417 are substantially fixedly positioned relative to one another when rotational components 1402 of rotary units 1400 rotate relative to support components 1417 and to one another. Essentially any attachment technique is optionally utilized to attach support components 1417 to one another. Some exemplary techniques include, for example, bonding, welding, adhering, or the like. In some embodiments, multiple support components 1417 are fabricated as single integral part (e.g., as a molded part or the like). FIG. 22B schematically shows an assembly of four gear structure 1415 from a side view. FIG. 22C schematically depicts the gear structure assembly of FIG. 22B from a rear side view, while FIG. 22D schematically depicts the gear structure assembly of FIG. 22B from a front side view.

To further illustrate, FIG. 22E schematically shows rotary mechanism 2200 that includes the gear structure assembly of FIG. 22B from a sectional view according to one embodiment of the invention. As shown, rotary mechanism 2200 includes four rotary units 1400. Counter-rotation of neighboring rotational components 1402 in rotary mechanism 2200 is effected by drive mechanism component 2202, which includes shaft component 2206 and gear component 2204. FIG. 22F schematically shows rotary mechanism 2200 from a side view. Rotational components 1402 of rotary units 1400 of rotation mechanism 2200 are configured to rotate relative to support components 1417, which support components 1417 are substantially fixedly positioned when rotational components 1402 rotates relative to support components 1417. Gear components 1414 are configured to rotate relative to rotational components 1402.

Figure 23T:
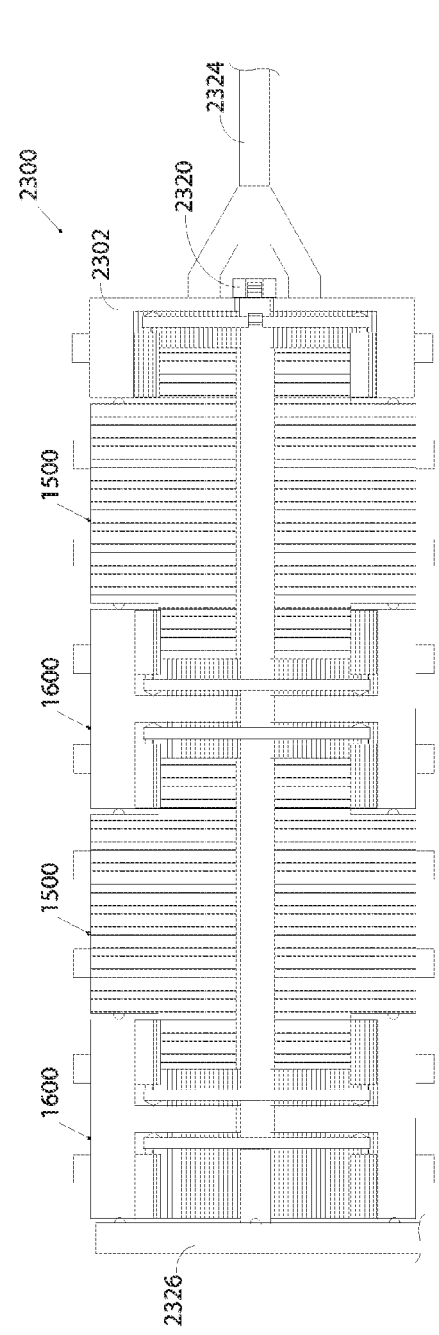
FIG. 23T schematically depicts a sectional side view of the rotational mechanism from FIG. 23B and the portion of the drive mechanism component of FIG. 23E according to one embodiment of the invention.
Figure 28B:
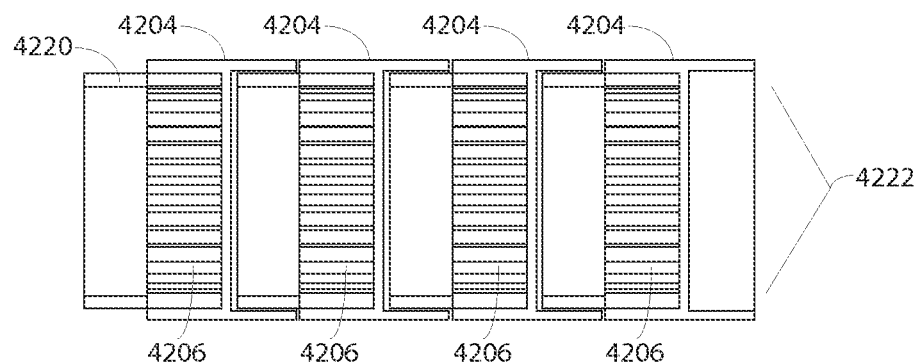
FIG. 28B schematically shows rotational components positioned relative to one another from a cross-sectional view according to one embodiment of the invention.
Figure 28C:
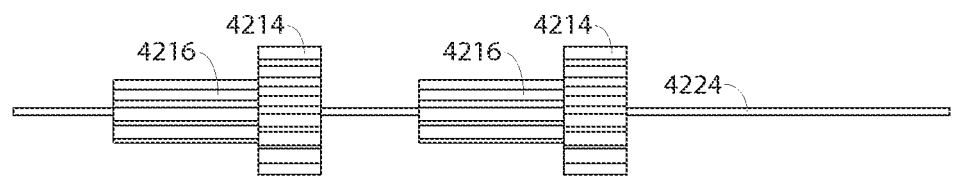
FIG. 28C schematically illustrates gear components of a counter-rotational mechanism operably engaging a drive mechanism component from a side view according to one embodiment of the invention.
Figure 28D:
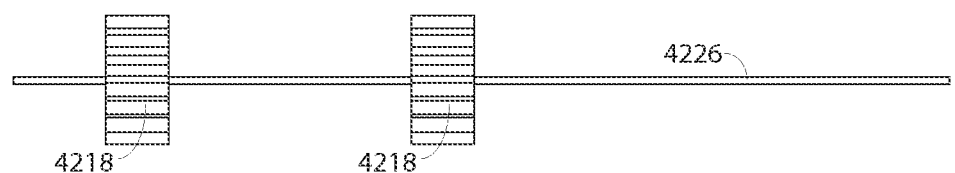
FIG. 28D schematically illustrates gear components of a counter-rotational mechanism operably engaging a drive mechanism component from a side view according to one embodiment of the invention.
Figure 28E:
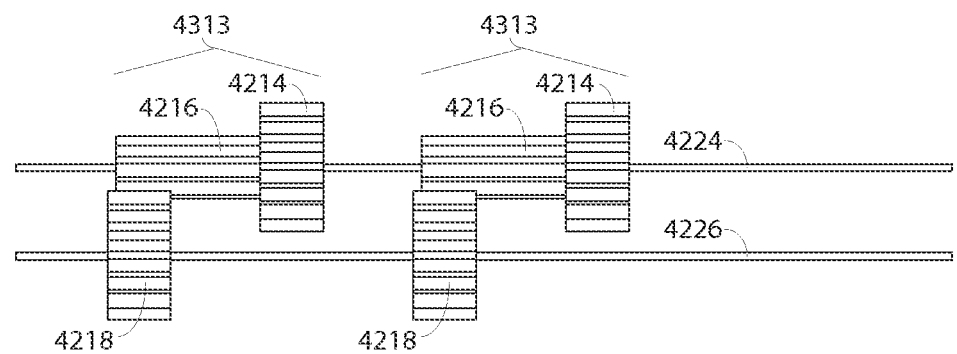
FIG. 28E schematically shows the gear and drive mechanism components from FIGS. 28 C and D positioned relative to one another from a side view.
Figure 28F:
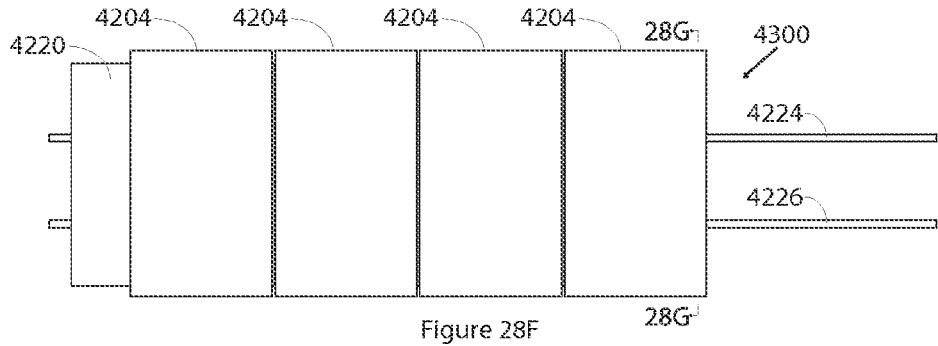
FIG. 28F schematically shows the rotary mechanism from FIG. 28A from a side view.
Figure 28G:
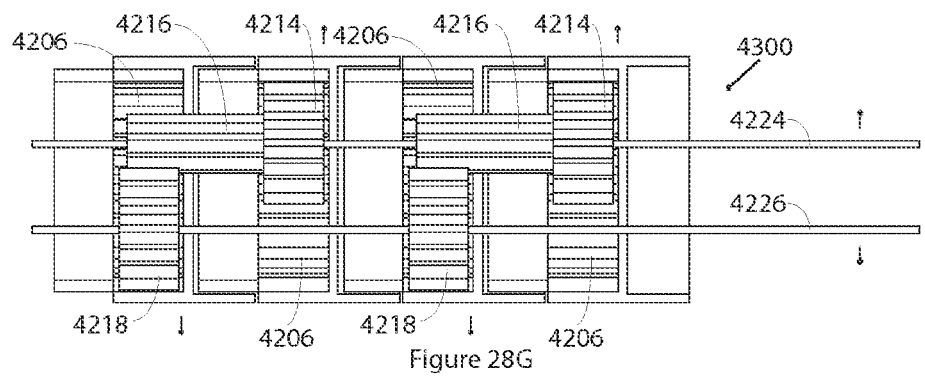
FIG. 28G schematically depicts the rotary mechanism from FIG. 28A from a side sectional view.
Figure 28H:
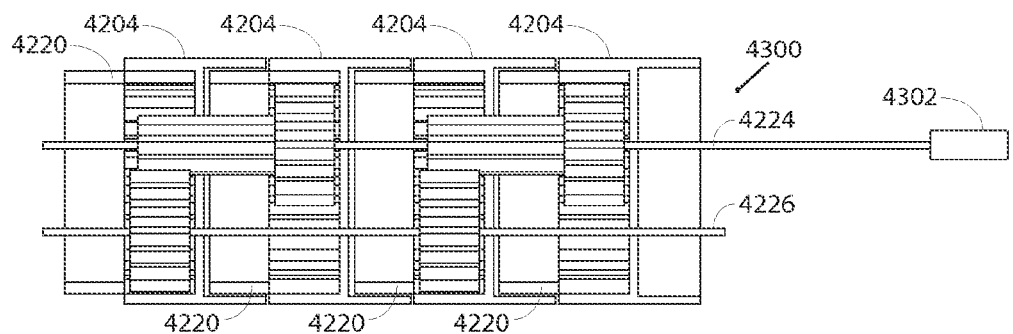
FIG. 28H schematically depicts the rotary mechanism from FIG. 28G from a side sectional view with an exemplary motor.
Figure 28I:
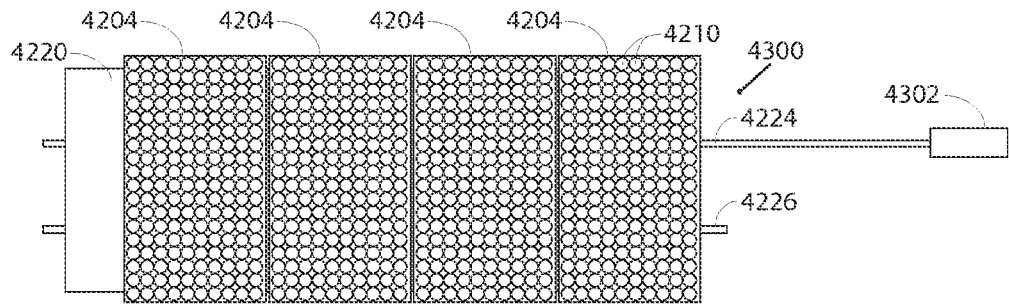
FIG. 28I schematically shows the rotary mechanism from FIG. 28H from a side view with rotational components including implements.

FIGS. 23A-T schematically depict a rotational mechanism or components thereof according to one embodiment of the invention. To illustrate, FIGS. 23A and C, for example, schematically depicts a portion of rotational or rotary mechanism 2300 from an exploded side and exploded side sectional views, respectively. During assembly of rotational mechanism 2300, support component 1614 of one rotary unit 1600 is inserted through hole 1508 of rotary unit 1500 and threaded region 1632 of that support component 1614 is received and retained in threaded region receiving area of another rotary unit 1600.

FIGS. 23E-P schematically show a portion of a drive mechanism component that is utilized to effect counter-rotation of neighboring pairs of rotary unit 1500 and rotary unit 1600 of rotational mechanism 2300. As shown, the portion of the drive mechanism component includes rotational component 2302, which includes ring gear component 2304, hole 2306, and implements 2308. The portion of the drive mechanism component also includes gear structure 2310, which includes support structure 2312 and planetary gear components 2314 rotatably coupled to support structure 2312. Support structure 2312 also includes friction reducing materials 2316 (shown as elevated or pointed surface features) to, e.g., reduce friction between support structure 2312 and rotational component 2302 when rotational component 2302 rotates relative to support structure 2312. Support structure 2312 also includes threaded region 2318, which is received by a corresponding threaded region receiving area of fastener 2320 (e.g., a nut or the like) through hole 2306 to hold gear structure 2310 in position relative to rotational component 2302, yet permit rotational component 2302 to rotate relative to support structure 2312 and planetary gear components 2314. In addition, support structure 2312 also includes threaded region receiving area 2322, which is configured to receiving thread region 1632 of a rotary unit 1600, e.g., in assembled rotational mechanism 2300.

Figure 67:
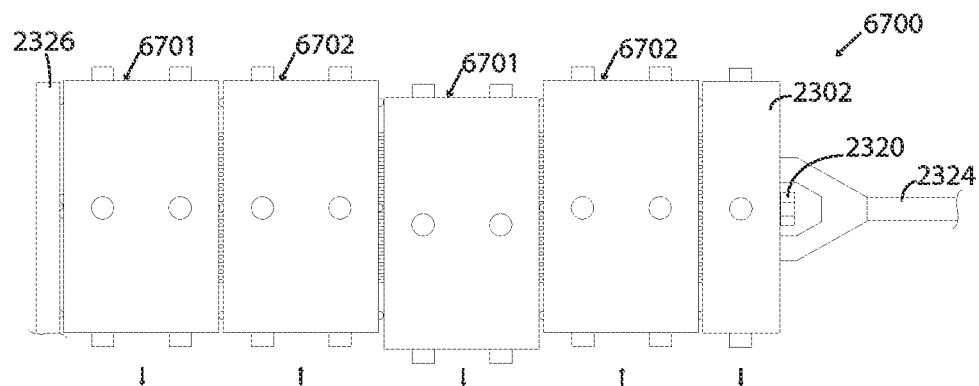
FIG. 67 schematically shows a rotary mechanism that includes rotational components having resilient couplings from a side view according to one exemplary embodiment of the invention.

As also shown, a shaft 2324 is also fixedly connected to rotational component 2302. Although not shown, a motor or the like is typically operably connected to shaft 2324, which effects the rotation of shaft 2324 and the counter-rotation of neighboring pairs of rotary unit 1500 and rotary unit 1600 of rotational mechanism 2300 (e.g., as schematically depicted by the directional arrows shown, e.g., in FIG. 23S) during operation. In addition, a rotary unit 1600 also operably connects to support component 2326 via threaded region receiving area 1634 of support structure 1614, e.g., such that support structures 1614 of rotary units 1600 and support structure 2312 of gear structure 2310 are substantially fixedly positioned when rotary units 1500, rotary units 1600, and rotational component 2302 rotate relative to one another in rotational mechanism 2300. Essentially any support component is optionally used. In some embodiments, support components are included in or as part of devices, apparatus, or other applications of the rotational mechanisms of the invention. Exemplary support components and applications are described herein. FIG. 67 schematically shows rotary mechanism 6700 that includes rotational components 6701 and 6702 having resilient couplings (see, e.g., directional arrows) from a side view according to one exemplary embodiment of the invention.

FIGS. 28 A-I schematically illustrate a rotary mechanism or components thereof from various views according to one exemplary embodiment of the invention. As shown, rotary mechanism 4300 includes rotational components 4204, which include gear components 4206 (e.g., ring gear components). Rotary mechanism 4300 also includes counter-rotational mechanism 4313 that includes first gear components 4214 that operably engage (e.g., mesh with) a ring gear component 4206 of a first rotational component 4204 of a neighboring pair of rotational components. Counter-rotational mechanism 4313 also includes second gear components 4218 that operably engage (e.g., mesh with) a ring gear component 4206 of a second rotational component 4204 of a neighboring pair of rotational components. Counter-rotational mechanism 4313 also includes third gear components 4216 that operably engage (e.g., mesh with second gear components 4218 such that when first gear components 4214 rotate in a first direction, first rotational components 4204 of neighboring pairs of rotational components rotate in the first direction and second gear components 4218 and second rotational components 4204 of neighboring pairs of rotational components rotate in a second direction (e.g., substantially opposite the first direction).

Rotational components 4204 include alignment components 4220 and alignment component receiving areas 4222 that are configured to align rotational components 4204 relative to one another, e.g., when rotational components 4204 rotate. As shown, an alignment component receiving area 4222 of a given rotational component 4204 is configured to receive at least a portion of an alignment component 4220 of another rotational component 4204. In this exemplary embodiment, alignment components 4220 are shown as circular ridge structures. Other alignment components or mechanisms are also optionally used to align rotational components relative to one another in the rotary mechanisms of the invention. In some embodiments, friction reducing materials are disposed between neighboring pairs of rotational components in a rotary mechanism to reduce friction between the rotational components when the rotational components rotate relative to one another. In some embodiments, for example, one or more lubricants are disposed between at least one neighboring pair of rotational components 4204 before and/or after the alignment component 4220 of one rotational component 4204 is inserted into the alignment component receiving area 4222 of another rotational component 4204. Other exemplary friction reducing materials that are optionally used or adapted for use with the rotary mechanisms of the invention are described herein or otherwise known to those of skill in the art.

Figure 69:
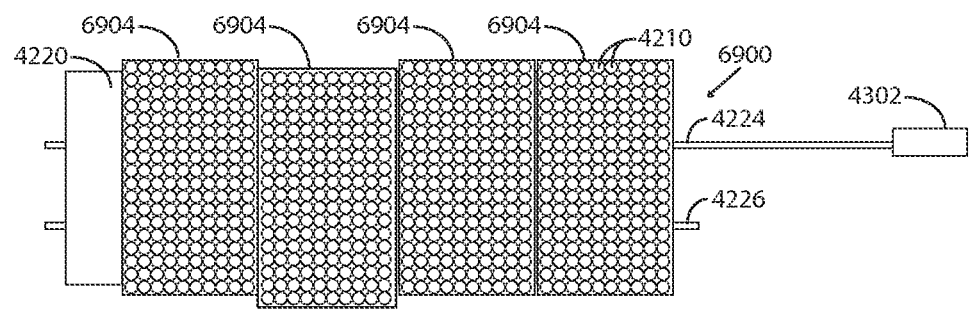
FIG. 69 schematically shows a rotary mechanism that includes rotational components having resilient couplings from a side view according to one exemplary embodiment of the invention.

Rotary mechanism 4300 also includes drive mechanism components or portions thereof 4224 and 4226 (e.g., shown as shaft components in this exemplary embodiment). As shown, shaft component 4224 operably engages first gear components 4214 and third gear components 4216, while shaft component 4226 operably engages second gear components 4218. As also shown, rotary mechanism 4300 also includes drive mechanism components or portions thereof 4302 (e.g., shown as motor in this exemplary embodiment) operably connected to shaft component 4224. Motor 4302 is configured to effect rotation of shaft component 4224 and thereby first gear components 4214 and third gear components 4216 as well as shaft component 4226 and second gear components 4218 such that when first gear components 4214 rotate in a first direction, first rotational components 4204 of neighboring pairs of rotational components rotate in the first direction and second gear components 4218 and second rotational components 4204 of neighboring pairs of rotational components rotate in a second direction (e.g., substantially opposite the first direction). Rotary mechanism 4300 is typically operably incorporated into, or otherwise operably associated with, a device, vehicle, or the like. Exemplary devices, vehicles, or other applications that are optionally used or adapted for use with rotary mechanism 4300 or the like are, e.g., described further herein. FIG. 69 schematically shows rotary mechanism 6900 that includes rotational components 6904 having resilient couplings from a side view according to one exemplary embodiment of the invention.

The rotary mechanisms of the invention or components thereof are fabricated or assembled using various techniques. In some embodiments, rotary mechanisms are assembled using rotational components that include multiple portions. As shown in FIGS. 29 A-C, for example, a rotary mechanism is optionally assembled using rotational components 4400, which each include rotational component portion 4402 and rotational component portion 4404. Rotational component portions 4402 and rotational component portions 4404 include portions of the ring gear components, alignment components, and alignment component receiving areas described herein, e.g., with respect to rotational components 4204. Rotational component portions 4402 also include alignment features 4406 and rotational component portions 4404 also include corresponding alignment feature receiving areas (not within view) that are configured to receive alignment features 4406. As shown, during assembly, rotational component portions 4402 and rotational component portions 4404 are joined (e.g., adhered, bonded, welded, etc.) with one another and positioned in operable engagement with first gear components 4214 and second gear components 4218 to form rotary mechanisms.

In certain embodiments, rotary mechanisms are assembled using shaft components that include multiple portions. FIGS. 30 A and B, 31 A and B, 32 A and B, and 33 show aspects of one of these exemplary embodiments. As shown, shaft component portion 4500 includes drive mechanism component receiving area 4700 and shaft component portion 4502 includes notched portion 4702 that is configured to be received by drive mechanism component receiving area 4700 of shaft component portion 4500. Shaft component portion 4500 and shaft component portion 4502 are each operably connected to a first gear component 4214 and a third gear component 4216. In addition, shaft component portion 4504 includes drive mechanism component receiving area 4700 and shaft component portion 4506 includes notched portion 4702 that is configured to be received by drive mechanism component receiving area 4700 of shaft component portion 4504. Shaft component portion 4504 and shaft component portion 4506 are each operably connected to a second gear component 4218. As shown, for example, in FIG. 33 rotational components 4204 are positioned relative to first gear components 4214 operably connected to shaft component portion 4500 or shaft component portion 4502 or second gear components 4218 operably connected to shaft component portion 4504 or shaft component portion 4506 and corresponding drive mechanism component receiving areas 4700 and notched portions 4702 are joined together during the assembly of a rotary mechanism in this exemplary embodiment. In some embodiments, multiple shaft portions and multiple rotational component portions are used together in the assembly of rotary mechanisms. Other exemplary rotary mechanism or component fabrication and assembly techniques are described herein.

As also shown, rotational components 4204 of rotary mechanism 4300 also include implements 4210. Other exemplary implements that are optionally used or adapted for use with rotational components 4204 are described further herein. In some embodiments, for example, implements are rotatably coupled to rotation components. In some of these embodiments, implements are configured to operably engage one or more gear components of one or more other rotational components. Rotatably coupled implements are described further herein, for example, with respect to FIGS. 6A-G, 24A-D, 25 A and B, and 26.

Figure 35A:
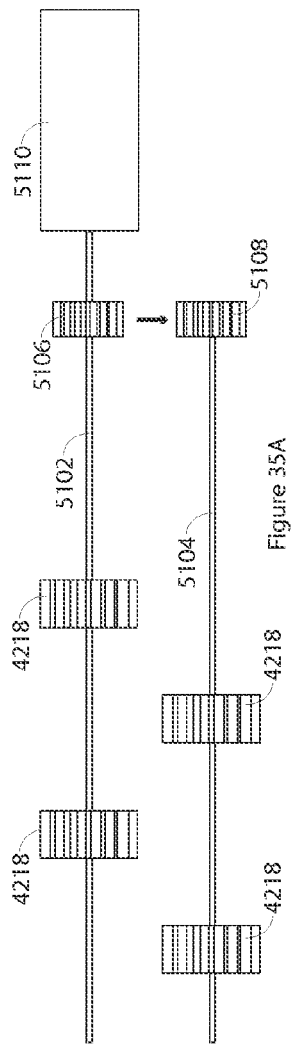
FIG. 35A schematically illustrates gear and drive mechanism components of a rotary mechanism prior to assembly from a side view.
Figure 35B:
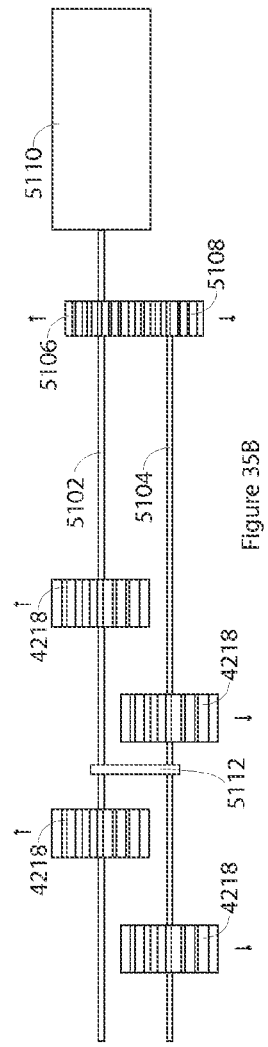
FIG. 35B schematically illustrates gear and drive mechanism components of a rotary mechanism from a side view.
Figure 35C:
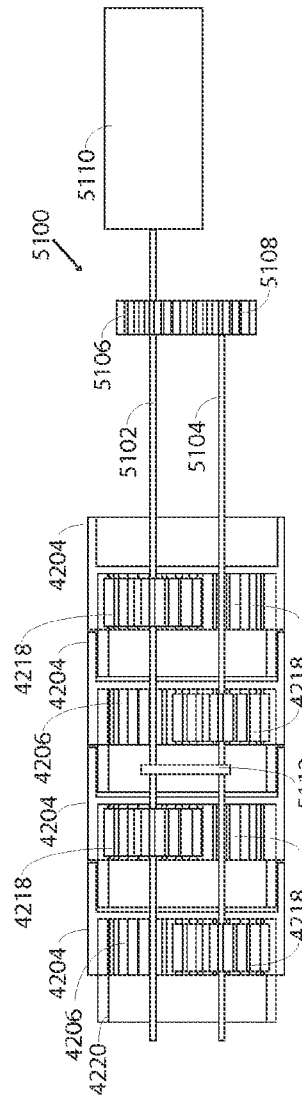
FIG. 35C schematically illustrates the gear and drive mechanism components from FIG. 35B positioned relative to rotational components from a sectional side view.

FIGS. 35 A-F schematically show a rotary mechanism or components thereof from various views according to one exemplary embodiment of the invention. As shown, rotary mechanism 5100 includes rotary units that include rotational components 4204. Rotational components 4204 include gear components 4206 (e.g., ring gear components). Additional details about rotational components (e.g., rotational components 4204) are described further herein. The rotary units also include second gear components 4218, which are configured to operably engage gear components 4206 of rotational components 4204. Rotary mechanism 5100 also includes a drive mechanism component or portion thereof that operably engages second gear components 4218. The drive mechanism component or portion thereof is configured to effect rotation of second gear components 4218 such that rotational component 4204 of one rotary unit of a neighboring pair of rotary units rotates in a first direction and rotational component 4204 of the other rotary unit of the neighboring pair of rotary units rotates in a second direction. As shown, the drive mechanism component or portion thereof includes shaft component 5102 and shaft component 5104. Shaft component 5102 operably engages second gear components 4218 of one rotary unit of each neighboring pair of rotary units, while shaft component 5104 operably engages second gear components 4218 of the other rotary unit of each neighboring pair of rotary units. Shaft component 5102 and shaft component 5104 are also operably connected to drive gear components 5106 and 5108, respectively. In assembled rotary mechanism 5100, drive gear components 5106 and 5108 mesh with one another. As shown, shaft component 5102 is also operably connected to motor 5110. Motor 5110 is configured to effect rotation of shaft component 5102 and thereby second gear components 4218 and corresponding rotational components 4204 of one rotary unit of each neighboring pair of rotary units in a first direction and second gear components 4218 and corresponding rotational components 4204 of the other rotary unit of each neighboring pair of rotary units via drive gear components 5106 and 5108 and shaft component 5104 in a second direction. In some embodiments, rotary mechanisms also include drive mechanism positioning components that are configured to position drive mechanism components or portions thereof relative to one another. To illustrate, rotary mechanism 5100 includes drive mechanism positioning component 5112, which includes holes 5114. Shaft component 5102 and shaft component 5104 are configured to fit and rotate within holes 5114 such that shaft component 5102 and shaft component 5104 are positioned relative to one another at least during rotation. Rotary mechanism 5100 is typically operably incorporated into, or otherwise operably associated with, a device, vehicle, or the like. Exemplary devices, vehicles, or other applications that are optionally used or adapted for use with rotary mechanism 5100 or the like are, e.g., described further herein.

IV. Exemplary Applications

FIGS. 24 A-D schematically illustrate an exemplary tooth brushing device or components thereof according to one embodiment of the invention. As shown, tooth brushing device 2700 includes rotary mechanism 2702, which includes a plurality of rotary units 600, as described above. Tooth brushing device 2700 also includes toothbrush head component or portion 2704 and handle component or portion 2706.

Toothbrush head component 2704 includes rotary mechanism housing 2708, which partially exposes a portion of the bristles of rotary mechanism 2702 through an opening in rotary mechanism housing 2708 during operation. Toothbrush head gear components 2710 and drive shaft 2712 also extend into a portion of rotary mechanism housing 2708. Drive shaft 2712 is received through drive mechanism receiving areas of rotational components 602 of rotary units 600 of rotary mechanism 2702. Toothbrush head gear components 2710 operably engage gear components 604 and 624 of a rotary unit 600 to effect counter rotation of neighboring rotational components 602 and implements 622 of rotary mechanism 2702. Rotary mechanism cap 2714 attaches to drive shaft 2712 to retain rotary mechanism positioned relative to toothbrush head gear components 2710. Handle component 2706 houses a motor (not within view) that operably connects to toothbrush head gear components 2710 and drive shaft 2712. A power source, such as a rechargeable battery (e.g., induction chargeable, etc.) or the like is also housed in handle component 2706 is some embodiments. In certain embodiments, the motor is optionally connected to other types of power sources, such as photovoltaic cells attached to handle component 2706, external power sources, or the like. As also shown, handle component 2706 also includes switch 2716, which is used, e.g., to turn tooth brushing device 2700 on and off, regulate speeds or modes (e.g., oscillation modes, select direction, etc.) of rotary unit rotation, or the like.

FIGS. 25 A and B schematically show an exemplary rotary mechanism or toothbrush head component that is optionally used, e.g., with handle component 2706 of tooth brushing device 2700. As shown, rotary mechanism 2800 includes a plurality of rotary units 600 in which implements 2802 (raised elastomeric regions, e.g., for tooth polishing) have been substituted for implements 622 on several individual rotary units. FIG. 25B schematically shows toothbrush head component 2804, which includes rotary mechanism 2800.

FIG. 26 schematically illustrates an exemplary cleaning device from a side view according to one embodiment of the invention. As shown, cleaning device 2900 includes a rotary mechanism that includes rotary units similar to rotary units 600, which are described further herein. Exemplary uses of cleaning device 2900 include cleaning outdoor cooking grills, dishes, and toilets, among many possible applications.

FIGS. 34 A-C schematically depict a tooth brushing device or components thereof from various views according to one exemplary embodiment of the invention. As shown, tooth brushing device 4900 includes rotary mechanism 4300, as described herein. Tooth brushing device 4900 also includes toothbrush head component or portion 4902 and handle component or portion 4904. Toothbrush head component 4902 includes rotary mechanism housing 4906, which partially exposes a portion of the implements of rotary mechanism 4300 through an opening in rotary mechanism housing 4906. Rotary mechanism 4300 is operably connected to motor 4302 via shaft component 4908. Motor 4302 is housed in handle component 4904. A power source, such as a rechargeable battery (e.g., induction chargeable, etc.) or the like is also housed in handle component 4904 in some embodiments. As shown, for example, battery component 4910 is operably connected to motor 4302 in handle component 4904. In certain embodiments, the motor is optionally connected to other types of power sources, such as photovoltaic cells attached to head component 4902 and/or handle component 4904, external power sources, or the like. As also shown, handle component 4904 also includes switch 4912, which is used, e.g., to turn tooth brushing device 4900 on and off, regulate speeds or modes (e.g., oscillation modes, select direction, etc.) of rotary unit rotation, or the like. Additional details regarding tooth brushing devices or components thereof are described herein.

FIGS. 36 A and B schematically show a tooth brushing device or components thereof from various views according to one exemplary embodiment of the invention. As shown, tooth brushing device 5200 includes rotary mechanism 5100, as described herein. Tooth brushing device 5200 also includes toothbrush head component or portion 5202 and handle component or portion 5204. Toothbrush head component 5202 includes rotary mechanism housing 5206, which partially exposes a portion of the implements of rotary mechanism 5100 through an opening in rotary mechanism housing 5206 during operation. Rotary mechanism 5100 is operably connected to motor 5110 via shaft component 5102. Motor 5110 is housed in handle component 5204. A power source, such as a rechargeable battery (e.g., induction chargeable, etc.) or the like is also housed in handle component 5204 in some embodiments. As shown, for example, battery component 5208 is operably connected to motor 5110 in handle component 5204. In certain embodiments, the motor is optionally connected to other types of power sources, such as photovoltaic cells attached, e.g., to head component 5202 and/or handle component 5204, external power sources, or the like. As also shown, handle component 5204 also includes switch 5210, which is used, e.g., to turn tooth brushing device 5200 on and off, regulate speeds or modes (e.g., oscillation modes, select direction, etc.) of rotary unit rotation, or the like. Additional details regarding tooth brushing devices or components thereof are described herein. FIG. 72 schematically shows a tooth brushing device that includes rotational components 7200 having resilient couplings from a side view according to one embodiment of the invention.

FIGS. 37 A-D schematically illustrate an exemplary tooth brushing device or components thereof according to one embodiment of the invention. As shown, tooth brushing device 3700 includes rotary mechanism 3702, which includes a unitary rotary unit or rotational component that is configured to rotate at least partially around rotational axis 3703. Tooth brushing device 3700 also includes toothbrush head component or portion 3704 and handle component or portion 3706. In some embodiments, toothbrush head component 3704 and handle component 3706 are fabricated integral with one another. In other exemplary embodiments, toothbrush head component 3704 and handle component 3706 are detachable from one another, e.g., toothbrush head component 3704 can be purchased as a replacement part for use with handle component 3706. Other handheld devices described herein are also optionally similarly configured. Toothbrush head component 3704 includes rotary mechanism housing 3708, which partially exposes a portion of the bristles or implements of rotary mechanism 3702 through an opening in rotary mechanism housing 3708 during operation. As shown, the surface of rotary mechanism 702 that includes the bristles is configured to rotate substantially non-perpendicular to rotational axis 3703. Toothbrush head gear component 3710 and drive shaft 3712 also extend into a portion of rotary mechanism housing 3708. Drive shaft 3712 is received through drive mechanism receiving areas of rotary mechanism 3702. Toothbrush head gear component 3710 operably engages gear components of rotary mechanism 3702 to effect rotation of rotary mechanism 3702. Rotary mechanism cap 3714 attaches to drive shaft 3712 to retain rotary mechanism positioned relative to toothbrush head gear component 3710. Handle component 3706 houses a motor (not within view) that operably connects to toothbrush head gear component 3710 and drive shaft 3712. A power source, such as a rechargeable battery (e.g., induction chargeable, etc.) or the like is also housed in handle component 3706 in some embodiments. In certain embodiments, the motor is optionally connected to other types of power sources, such as photovoltaic cells attached to head component 3704 and/or handle component 3706, external power sources, or the like. As also shown, handle component 3706 also includes switch 3716, which is used, e.g., to turn tooth brushing device 3700 on and off, regulate speeds, modes, and/or direction of rotary unit rotation, or the like. In some embodiments, for example, a user uses switch 3716 to change the direction of rotary mechanism 3702 rotation away from the user's gums according to the teeth being brushed at a given point in time. In some embodiments, only a single or unitary rotational component selectively rotates in one or two directions or oscillates to effect cleaning. It can be programmed such that bristles, rubber implements, etc. always rotate toward the non-gum edge (i.e., away from the gum line) of a set of teeth (e.g., to push the gums toward that edge, rather than away from the edge) in some embodiments. For example, tooth brushing device 3700 is optionally programmed such that rotation adjusts manually or automatically depending on how the toothbrush rotational component is oriented relative to the teeth (e.g., top or bottom teeth, inside or outside of teeth).

Figure 38A:
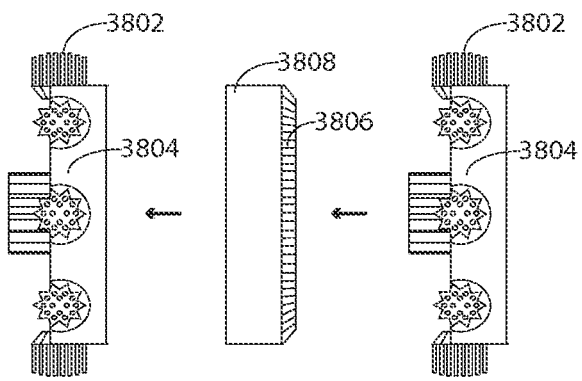
FIG. 38A schematically depicts portions of a rotational or rotary mechanism prior to assembly from a side view according to one embodiment of the invention.
Figure 38B:
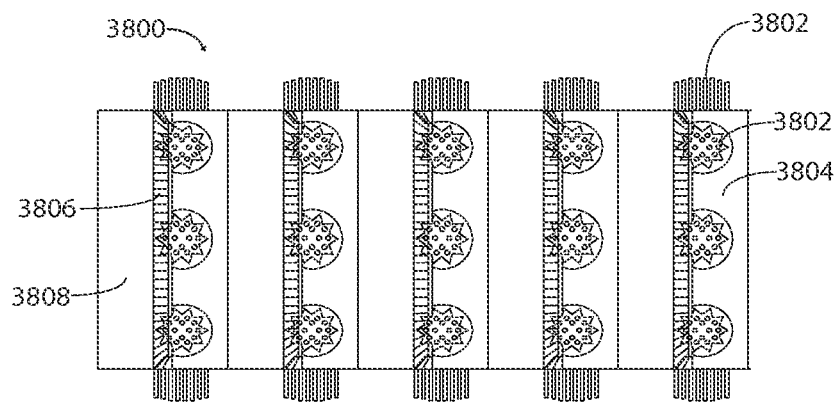
FIG. 38B schematically shows a rotational mechanism assembled from the portions illustrated in FIG. 38A from a side view.

To further illustrate, FIGS. 38 A and B schematically illustrate another exemplary embodiment of a rotational or rotary mechanism that is optionally adapted for use with the handheld devices of the invention. As shown, rotational mechanism 3800, which includes fixed gear components 3808 and rotational components 3804, which are configured to rotate relative to fixed gear components 3808. Optionally, components 3804 are fixed and gear components 3808 are configured to rotate. Rotational components 3804 include rotational implements 3802 and fixed gear components 3808 include gears 3806, which mesh with rotational implements 3802. As rotational components 3804 rotate relative to fixed gear components 3808, rotational implements 3802 also rotate. Exemplary rotational implements are also described herein, e.g., with respect to FIGS. 6A-G, 24A-D, 25 A and B, and 26. In some embodiments, one member of a pair of rotational components is fixed (e.g., does not rotate), while the other rotates. In certain embodiments, the rotatable implements can be disposed on either or both members of a given neighboring pair of rotational components. Rotatable implements are also optionally used with oscillating embodiments, e.g., as described herein.

Figure 39A:
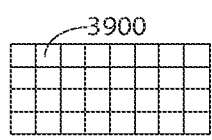
FIGS. 39 A and B schematically show top and side views, respectively, of exemplary implements according to one embodiment of the invention.
Figure 39B:
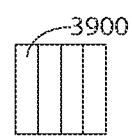
Figure 40A:
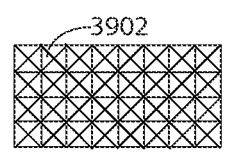
FIGS. 40 A and B schematically show top and side views, respectively, of exemplary implements according to one embodiment of the invention.
Figure 40B:
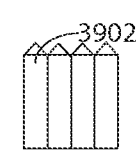
Figure 41A:
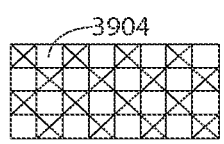
FIGS. 41. A and B schematically show top and side views, respectively, of exemplary implements according to one embodiment of the invention.
Figure 41B:
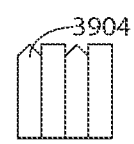
Figure 42A:
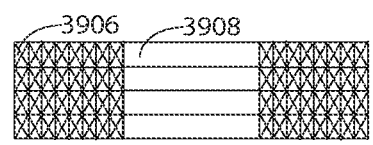
FIGS. 42A-E schematically illustrate top views of exemplary implements according to various embodiment of the invention.
Figure 42B:
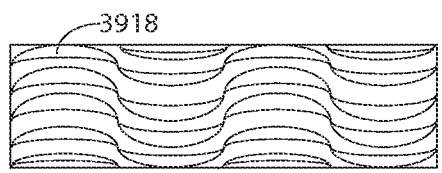
Figure 42C:
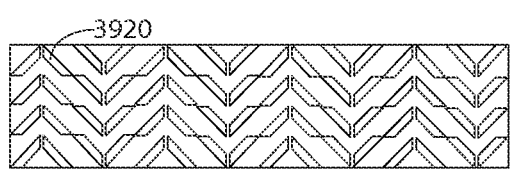
Figure 42D:
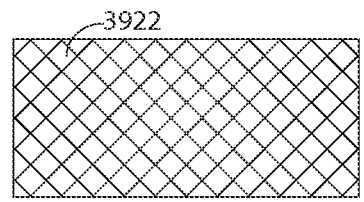
Figure 42E:
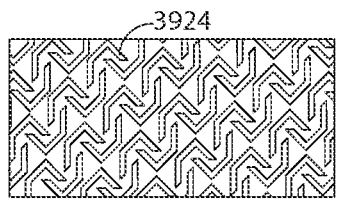
Figure 43A:
FIGS. 43A-C schematically illustrate side views of exemplary implements according to various embodiment of the invention.
Figure 43B:
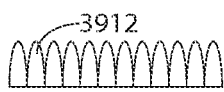
Figure 43C:
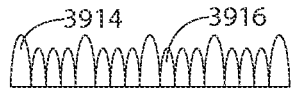

FIGS. 39 A and B, 40 A and B, 41 A and B, 42A-E, and 43A-C schematically illustrate various representative implements 3900-3920 that are optionally used (e.g., alone or in essentially any combination) in, e.g., the counter-rotating rotary mechanisms, oscillating counter-rotating rotary mechanisms, unitary or single direction rotary mechanisms, rotational implement mechanisms embodiments of the devices of the invention. The implements can be fabricated from many different materials. In some embodiments, for example, implements are made from elastomeric, rubber, and/or plastic materials (e.g., rubber typically used in dental cleaning devices). More specifically, FIGS. 39 A and B schematically depict implements 3900 organized in rows and columns of pegs from top and side views, respectively. FIGS. 40 A and B schematically depict implements 3902 organized in rows and columns of pegs with pyramid-shaped tips from top and side views, respectively. FIGS. 41A and B schematically depict implements 3904 organized in rows and columns of pegs with or without pyramid-shaped tips from top and side views, respectively. FIG. 42A schematically illustrates a combination of pyramid-shaped implements 3906 and linear ridge-shaped implements 3908 from a top view. FIG. 42B schematically illustrates curved ridge-shaped implements 3918 from a top view. FIG. 42C schematically illustrates angled ridge-shaped implements 3920 from a top view. FIG. 42D schematically shows diagonally disposed peg-shaped implements 3922 from a top view. FIG. 42E schematically depicts angled ridge-shaped implements 3924 from a top view. FIG. 43A schematically illustrates implements 3910 that include spherical portions from a side view. The spherical portions of these implements contact and clean the user's teeth during use in certain embodiments. FIGS. 43 B and C schematically depict semi-oval implements 3912, 3914, and 3916 from side views. In some embodiments, rotary mechanisms include only bristles, no bristles, or combinations of bristles with other types of implements.

Figure 44:
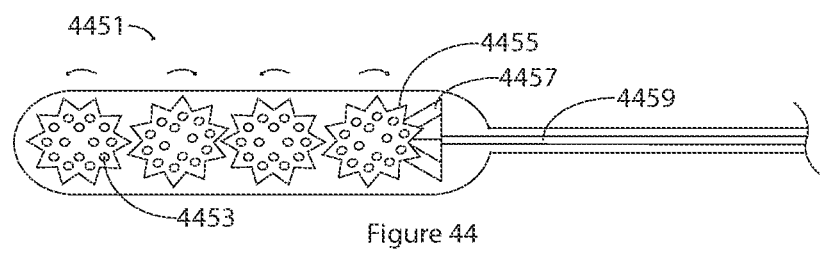
FIG. 44 schematically shows a head portion of a tooth brushing device from partially transparent top view according to one embodiment of the invention.
Figure 45A:
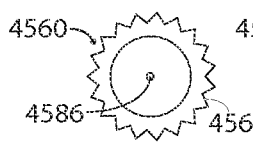
Figure 45B:
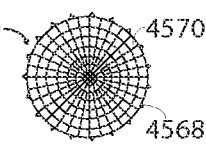
Figure 45C:
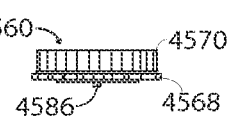
Figure 45D:
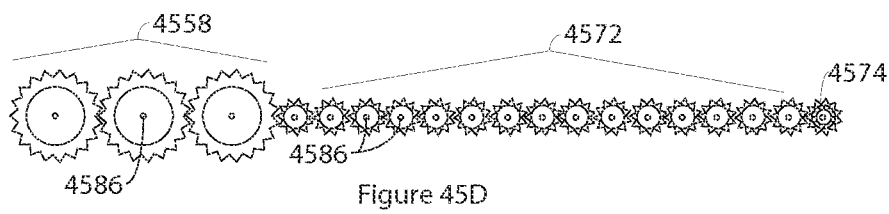
Figure 45E:
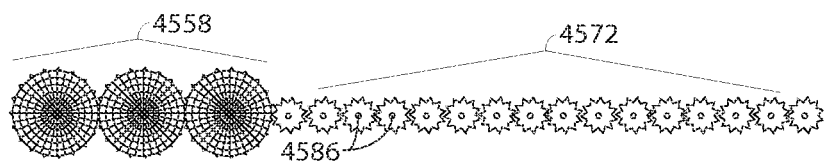

FIG. 44 schematically shows a head portion of a tooth brushing device from partially transparent top view according to one embodiment of the invention. As shown, head portion 4451 includes rotational components 4455 that include gear components that mesh with one another. Rotational components 4455 also have surfaces that are configured to rotate substantially perpendicular to rotational axes of rotational components 4455. These surfaces include implements 4453. One rotational component 4455 also meshes with gear component 4457. Gear component 4457 is operably connected to shaft component 4459, which is typically operably connected to a motor or the like (e.g., disposed in a handle portion of the tooth brushing device (not within view)) that is configured to effect rotation of shaft component 4459 and gear component 4457 (e.g., in one or both directions, in an oscillating mode, etc.). As gear component 4457 rotates, it effects the counter-rotation of rotational components 4455.

Figure 70:
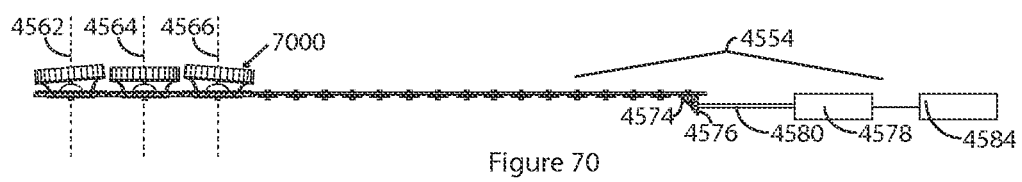
FIG. 70 schematically illustrates rotational components having resilient couplings and drive mechanism components or portions thereof operably connected to motor and power source components from a side view according to one embodiment of the invention.
Figure 71:
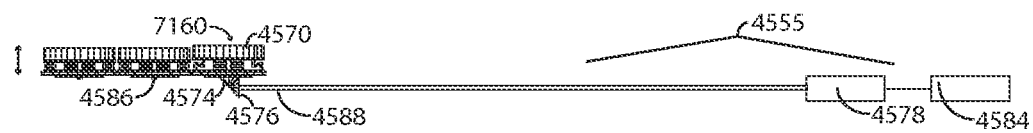
FIG. 71 schematically illustrates rotational components having resilient couplings and drive mechanism components or portions thereof operably connected to motor and power source components from a side view according to one embodiment of the invention.

FIGS. 45A-J schematically illustrate handheld devices (e.g., tooth brushing devices) or components thereof from various views according to certain embodiments of the invention. As shown, handheld device 4550 includes head portion 4552, drive mechanism component 4554, and handle portion 4556. In the embodiment shown, head portion 4552 and handle portion 4556 are fabricated integral with one another (i.e., non-detachable from one another). In other embodiments, head and handle portions (and drive mechanism components or portions thereof) are detachable from one another. Head portion 4552 includes rotary mechanism 4558, which includes three rotational components 4560 in this exemplary embodiment. Rotational components 4560 are configured to rotate at least partially around rotational axis 4562, 4564, or 4566. Rotational components 4560 include gear components 4568 that are configured to mesh with one or more gear components of neighboring rotational components and/or drive mechanism components. In the embodiment shown, each rotational component 4560 includes implements 4570 disposed on a surface that is configured to rotate substantially perpendicular to a rotational axis (e.g., rotational axis 4562, 4564, or 4566) of the rotational component 4560. In some embodiments, rotational components 4560 are selectively interchangeable with other rotational components (e.g., having the same or different implement configurations). FIG. 70 schematically illustrates rotational components 7000 having resilient couplings and drive mechanism components or portions thereof operably connected to motor and power source components from a side view according to one embodiment of the invention. FIG. 71 schematically illustrates rotational components 7160 having resilient couplings and drive mechanism components or portions thereof operably connected to motor and power source components from a side view according to one embodiment of the invention. FIG. 73 schematically shows a handheld device that includes rotational components 7000 having resilient couplings from a side view according to one embodiment of the invention.

Drive mechanism component 4554 includes a chain of meshed gear components 4572 that mesh with gear component 4568 of one rotational component 4560 and extend from head portion 4552 to handle portion 4556. As shown, one gear component 4572 includes gear 4574 that meshes with gear 4576. Gear 4576 is operably connected to motor component 4578 via shaft component 4580. Motor component 4578 is also operably connected to switch component 4582 (e.g., an on/off switch, etc.) and power source component 4584 (e.g., a rechargeable battery, etc.). During operation, motor component 4578 effects rotation of shaft component 4580, gears 4574 and 4576, and gear components 4572 such that neighboring pairs of rotational components 4560 rotate at least partially around rotational axis 4562, 4564, or 4566 in directions (see, directional arrows shown, for example, in FIG. 45E) that are substantially opposite one another. Rotary mechanism 4558 and drive mechanism component 4554 are at least partially disposed within a housing. Rotational components 4560 and gear components 4572 include alignment components 4586 (shown as pegs in this embodiment) that align rotational components 4560 and gear components 4572 relative to the housing (e.g., via corresponding seatings (not within view)).

Other drive mechanism components are also optionally used with rotational components 4560. As shown in FIG. 45G, for example, drive mechanism component 4555 includes shaft component 4588 instead of chain of meshed gear components 4572. As shown, one rotational component 4560 includes gear 4574 that meshes with gear 4576. Gear 4576 is operably connected to motor component 4578 via shaft component 4588. Motor component 4578 is also operably connected to power source component 4584 (e.g., a rechargeable battery, etc.). During operation, motor component 4578 effects rotation of shaft component 4588, gears 4574 and 4576, and gear components 4568 such that neighboring pairs of rotational components 4560 rotate at least partially around rotational axis 4562, 4564, or 4566 in directions that are substantially opposite one another.

Figure 46A:
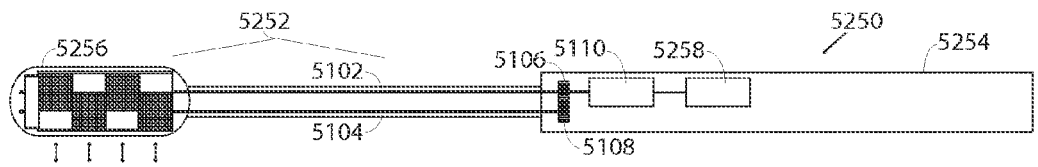
FIG. 46A schematically depicts a tooth brushing device from a partially transparent side view according to one exemplary embodiment of the invention.
Figure 46B:
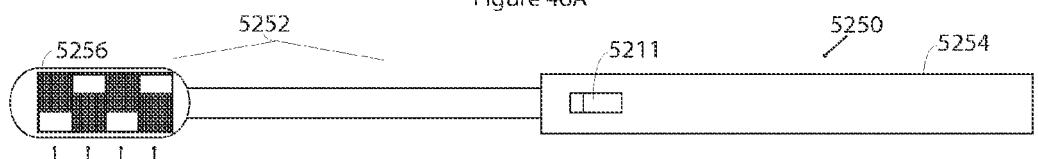
FIG. 46B schematically depicts the tooth brushing device from FIG. 46A from a side view.

FIGS. 46 A and B schematically show a tooth brushing device or components thereof from various views according to one exemplary embodiment of the invention. As shown, tooth brushing device 5250 includes rotary mechanism 5100, as described herein. Tooth brushing device 5250 also includes toothbrush head component or portion 5252 and handle component or portion 5254. Toothbrush head component 5252 includes rotary mechanism housing 5256, which partially exposes a portion of the implements of rotary mechanism 5100 through an opening in rotary mechanism housing 5256. Rotary mechanism 5100 is operably connected to motor 5110 via shaft component 5102. Motor 5110 is housed in handle component 5254. A power source, such as a rechargeable battery (e.g., induction chargeable, etc.) or the like is also housed in handle component 5254 in some embodiments. As shown, for example, battery component 5258 is operably connected to motor 5110 in handle component 5254. In certain embodiments, the motor is optionally connected to other types of power sources, such as photovoltaic cells attached, e.g., to head component 5252 and/or handle component 5254, external power sources, or the like. As also shown, handle component 5254 also include switch 5211, which is used, e.g., to turn tooth brushing device 5250 on and off, regulate speeds or modes of rotary unit rotation, or the like. In the illustrated embodiment, the exposed implements of rotary mechanism 5100 are configured to oscillate back and forth (see, directional arrows in FIGS. 46 A and B) in the opening in rotary mechanism housing 5256. Additional details regarding tooth brushing devices or components thereof are described herein.

Figure 47A:
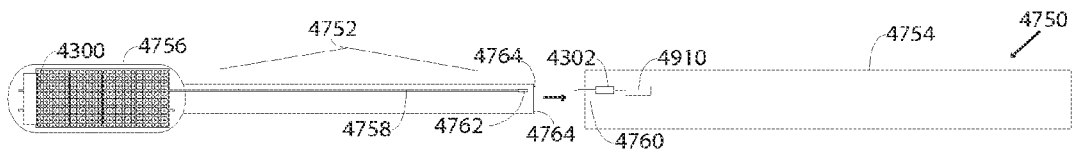
FIG. 47A schematically depicts a tooth brushing device with a head portion detached from a handle portion from a partially transparent side view according to one exemplary embodiment of the invention.
Figure 47B:
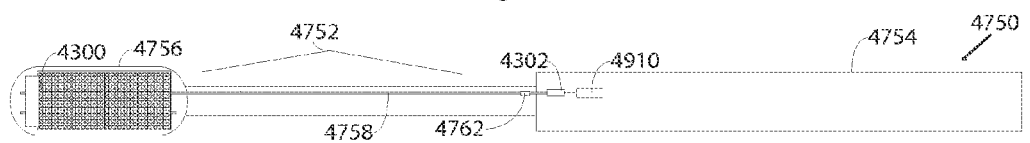
FIG. 47B schematically depicts the tooth brushing device from FIG. 47A with the head portion operably connected to the handle portion from a partially transparent side view.
Figure 48A:
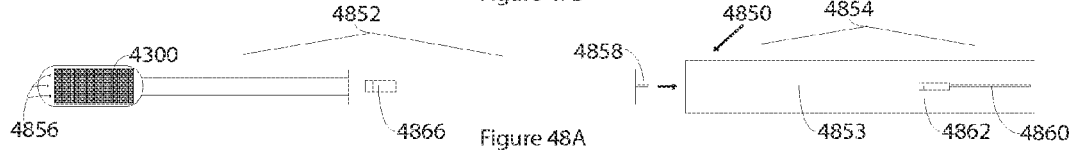
Figure 48B:
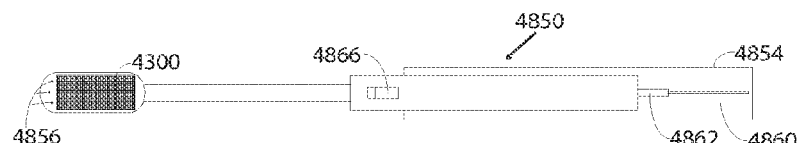
Figure 48C:
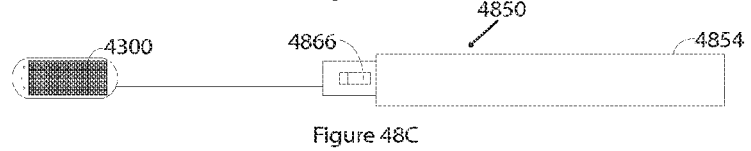

FIGS. 47 A and B schematically depict a tooth brushing device or components thereof from various views according to one exemplary embodiment of the invention. As shown, tooth brushing device 4750 includes rotary mechanism 4300, as described herein. The tooth brushing devices and other handheld devices of the invention are optionally adapted to include any of the rotary units or mechanisms described herein. Tooth brushing device 4750 also includes toothbrush head component or portion 4752 and handle component or portion 4754 that are detachable from one another. Toothbrush head component 4752 includes rotary mechanism housing 4756, which partially exposes a portion of the implements of rotary mechanism 4300 through an opening in rotary mechanism housing 4756. Rotary mechanism 4300 is operably connected or connectable to motor 4302 via rotary mechanism shaft component 4758 and motor shaft component 4760, which are reversibly operably connected to one another via drive mechanism component receiving area 4762. Toothbrush head portion 4752 is reversibly attached to handle portion 4754 via reversible attachment components 4764. Essentially any reversible attachment components are optionally utilized. Motor 4302 is housed in handle component 4754. A power source, such as a rechargeable battery or the like is also housed in handle component 4754 in some embodiments. As shown, for example, battery component 4910 is operably connected to motor 4302 in handle component 4754. In certain embodiments, the motor is optionally connected to other types of power sources, such as photovoltaic cells attached to head component 4752 and/or handle component 4754, external power sources, or the like. Additional details regarding tooth brushing devices or components thereof are described herein.

FIGS. 48A-F schematically illustrate a tooth brushing device or components thereof from various views according to one exemplary embodiment of the invention. As shown, tooth brushing device 4850 includes tooth brushing component 4852 and material container 4854 (shown as a material source or destination), which are detachable from one another. Tooth brushing component 4852 includes rotary mechanism 4300 and the drive mechanism components described, e.g., with respect to tooth brushing device 4900. Tooth brushing component receiving area 4853 of material container 4854 is configured to receive a portion of tooth brushing component 4852. In addition, tooth brushing component 4852 also includes openings 4856 that communicate with conduit 4858 and a material reservoir of material container 4854. Openings are optionally disposed essentially anywhere on the head portion of tooth brushing device 4850 and can be of essentially any number (e.g., one, two, three (as shown), four, five, six, seven, eight, nine, ten, or more) or configuration. Conduit 4858 is typically fabricated at least partially internal to a housing of tooth brushing component 4852. In addition, conduit 4858 is configured to communicate with material container conduit 4860 via junction 4862. Tooth brushing device 4850 also includes conveyance mechanism 4864 (e.g., a pump or the like), which is configured to convey material (e.g., fluidic material, semi-fluidic material, etc.) to and/or from a material reservoir of material container 4854 through openings 4856. As also shown, tooth brushing device 4850 includes switch 4866, which is operably connected to a drive mechanism component and conveyance mechanism 4864 of tooth brushing component 4852. Switch 4866 is used, e.g., to turn the drive mechanism component and/or conveyance mechanism 4864 of tooth brushing component 4852 on and off, regulate speeds or modes of rotary unit rotation and/or conveyance mechanism conveyance, or the like.

FIG. 49 schematically depicts portions of a tooth brushing device from a partially transparent side view according to one exemplary embodiment of the invention. As shown, tooth brushing device 4950 is configured similar to tooth brushing component 4852. Instead of communicating with material container 4854, conduit 4858 of tooth brushing device 4950 communicates with conduit 4952 via junction 4954. Conduit 4952 is configured to communicate with a material source or destination (not shown), such as an external fluid or material station, a faucet, or the like.

FIGS. 50A and B schematically illustrate a tooth brushing device or components thereof from various views according to one exemplary embodiment of the invention. As shown, tooth brushing device 5050 includes tooth brushing component 5052 and material container 5054 (shown as a material source or destination with two material reservoirs), which are detachable from one another. Tooth brushing component 5052 includes rotary mechanism 4300 (not within view) and the drive mechanism components described, e.g., with respect to tooth brushing device 4900. Tooth brushing component receiving area 5053 of material container 5054 is configured to receive a portion of tooth brushing component 5052. In addition, tooth brushing component 5052 also includes openings 5056 and 5057 that communicate with conduit 5058 and 5059, respectively, and material reservoirs of material container 5054. Openings are optionally disposed essentially anywhere on the head portion of tooth brushing device 5050 and can be of essentially any number (e.g., one, two (as shown), three, four, five, six, seven, eight, nine, ten, or more) or configuration. Conduits 5058 and 5059 are typically fabricated at least partially internal to a housing of tooth brushing component 5052. In addition, conduits 5058 and 5059 are configured to communicate with material container conduits 5060 and 5061 via junctions 5062 and 5063, respectively. Tooth brushing device 5050 also includes conveyance mechanisms 5064 and 5065 (e.g., pumps or the like), which are configured to convey material (e.g., fluidic material, semi-fluidic material, etc.) to and/or from material reservoirs 5067 and 5068 of material container 5054 through openings 5056 or 5057. Tooth brushing device 5050 also includes a switch (not within view), which is operably connected to a drive mechanism component and conveyance mechanisms 5064 and 5065 of tooth brushing component 5052. The switch is used, e.g., to turn the drive mechanism component and/or conveyance mechanisms 5064 and 5065 of tooth brushing component 5052 on and off, regulate speeds or modes of rotary unit rotation and/or conveyance mechanism conveyance, or the like.

FIG. 51 schematically shows a head portion of a tooth brushing device from a side view according to one exemplary embodiment of the invention. As shown, detachable head portion 5150 includes openings 4856 that communicate with conduit 5152. Detachable head portion 5150 also includes rotary mechanism 4300 and drive mechanism components described, e.g., with respect to tooth brushing devices 4750 and 4900. Detachable head portion 5150 also includes reversible attachment components 4764. Conduit 5152 is configured to communicate with a corresponding conduit in a handle portion of the toothbrushing device (not shown).

FIGS. 52A-C schematically illustrate a sanitizing component from various views according to one exemplary embodiment of the invention. As depicted, sanitizing component 5350 includes housing 5352 that forms wells 5354, which are configured to receive handheld devices or portions thereof (e.g., detachable head portion 5150) to store and/or sanitize the handheld devices or portions thereof, e.g., when not in use. For example, wells 5354 are optionally at least partially filled with a cleaning or sanitizing solution to cover at least part of the handheld devices or portions thereof when the handheld devices or portions thereof are disposed in wells 5354. In some embodiments, housing 5352 further includes ultraviolet light sources 5356 that communicate with wells 5354 and power source 5358. Ultraviolet light sources 5356 are configured to selectively expose at least part of the handheld devices or portions thereof to ultraviolet light to sanitize at least part of the head and/or handle portion of the handheld devices or portions thereof. In other exemplary embodiments, housing 5352 further includes fluidic conveyance systems that include fluid channels 5360 that fluidly communicate with wells 5354. Fluid conveyance mechanisms 5362 (e.g., pumps or the like) are also operably connected to fluid channels 5360 and configured to convey or re-circulate fluids (e.g., sanitizing fluidic materials) in wells 5354 through fluid channels 5360 to sanitize at least part of the head and/or handle portion of the handheld devices or portions thereof. In some embodiments, fluid channels 5360 are configured to also directly fluidly communicate with the conduits included in certain embodiments of the handheld devices described herein, e.g., via a tube or the like that fluidly connects the conduits to the fluid channels 5360 to also flow fluids (e.g., sanitizing fluidic materials) through the conduits.

FIG. 74A schematically illustrates cleaning device 3500 that includes rotational components having resilient couplings from a sectional view according to one embodiment of the invention. FIG. 74B schematically illustrates cleaning device 3500 from a side view. As shown, the rotary mechanism of cleaning device 3500 includes rotational components 3505 having resilient couplings. Rotational components 3505 also include implements 3507. Rotational components 3505 are aligned relative to one another and rotate around shaft 3502. The rotary mechanism is positioned relative to housing 3504 via mounting components 3506. As also shown, cleaning device 3500 also includes motor 3508, which effects the counter-rotation of rotational components 3505 in the rotary mechanism via drive shaft 3510 and meshed gear components 3512 and 3514. Cleaning device 3500 also includes power source 3516 (e.g., a battery or the like), which is operably connected to motor 3508 and switch 3518 in a handle portion of housing 3504. Cleaning device 3500 is optionally adapted for a variety of uses including, for example, cleaning dishes, cleaning countertops, cleaning floors, cleaning barbeque grills, cleaning ovens, cleaning toilets, buffing automobiles or other vehicles, and the like.

FIG. 75 schematically illustrates a rotor tiller that includes rotational components having resilient couplings from a front elevational view according to one embodiment of the invention. As shown, rotor tiller 2400 includes rotary mechanism 2462 that is operably connected to motor 2404 via shaft 2474. As also shown, rotor tiller 2400 also includes wheels 2402 and handle 2406 coupled to a support structure. Rotary mechanism 2462 includes rotational components 2463 having resilient couplings.

To further illustrate exemplary embodiments of the invention, FIG. 76A schematically shows vehicle 2500 from a side elevational view. As shown, vehicle 2500 includes two rotary mechanisms 2502 and grading blade 2503, which can each be independently raised and lowered. Rotary mechanisms 2502 include rotational components having resilient couplings. Rotary mechanisms can include various embodiments, including various types of implements (e.g., as described herein or the like). As also shown, vehicle 2500 also includes wheels 2504, driver's compartment 2506, and engine compartment 2508. Vehicle 2500 can be adapted for a wide variety of uses in, e.g., agricultural, construction, military, or other applications. In some embodiments, for example, vehicle 2500 is used to till, grade, and/or otherwise move soil. As another exemplary illustration, FIG. 76B schematically shows vehicle 2501 from a side elevational view. As shown, vehicle 2501 includes rotary mechanism 2510, which can be raised and lowered. Rotary mechanism 2501 includes rotational components having resilient couplings. As also shown, vehicle 2501 also includes wheels 2504, driver's compartment 2506, and engine compartment 2508. Vehicle 2501 can be adapted for a wide variety of uses. In some embodiments, for example, vehicle 2501 is used to till, grade, and/or otherwise move soil.

In other representative embodiments, the invention provides hair cutting devices, e.g., for cutting facial hair, leg hair, or hair on other body parts. To illustrate, FIGS. 77 A-C illustrate various aspects of a hair cutting device according to one embodiment of the invention. As shown, hair cutting device 2600 includes housing 2602, which comprises surfaces that define cavity 2604 disposed at least partially within housing 2602. Housing 2602 also includes opening 2606 that communicates with cavity 2604. A rotary mechanism is at least partially disposed within cavity 2604. The rotary mechanism includes multiple rotational components 2610 that are configured to substantially coaxially rotate (e.g., coaxially counter-rotate) relative to one another. Rotational components 2610 include resilient couplings. Rotational components 2610 also include cutting implements (e.g., razor blades or other sharp edges) that are configured to cut hair via opening 2606 when the multiple rotational components 2610 substantially coaxially rotate relative to one another and the cutting implements contact hair. The rotary mechanism also includes at least one counter-rotational mechanism, as described herein, operably coupled to rotational components 2610. The counter-rotational mechanism is configured to effect substantially simultaneous counter-rotation of neighboring pairs of rotational components 2610 relative to one another when movement of at least a portion of the counter-rotational mechanism is effected. In some embodiments, the rotational components are configured to coaxially counter-oscillate relative to one another about an axis of rotation of the rotary mechanism. In some of these embodiments, cutting implements include dual-sided cutting edges, e.g., to cutting hair in both directions of the oscillation.

As also shown, hair cutting device 2600 also includes a drive mechanism operably coupled to the counter-rotational mechanism and rotational components. In the embodiment shown, the drive mechanism includes motor 2616 (e.g., a stepper motor, a servo motor, etc.), which is configured to effect movement of the counter-rotational mechanism via shaft 2618 such that neighboring pairs of rotational components 2610 substantially simultaneously counter-rotate relative to one another. As also shown, switch 2617 (e.g., on/off switch, a variable speed control switch, and/or the like) is operably connected to motor 2616. Although not shown, hair cutting device 2600 also typically includes a power source (e.g., a power cord that plugs into a wall socket, a battery (rechargeable or not), a photovoltaic cell, etc.) operably connected to motor 2616.

Hair cutting device 2600 also includes removable structure 2620 (e.g., a shaving foil structure or the like) disposed in opening 2606. Removable structure 2620 comprises holes 2622 via which hair is cut when neighboring pairs of rotational components 2610 coaxially counter-rotate relative to one another and the cutting implements contact the hair. Individual portions of removable structure 2620 are typically configured to move as correspondingly aligned rotational components 2610 move due to the resilient couplings during operation (see, e.g., the directional arrows shown in FIG. 77B). Hair cutting devices also typically include support structures that are structured to support at least a portion of the rotational components, the counter-rotational mechanism, and/or the drive mechanism within the device housings.

Device components (e.g., rotary units, rotary mechanisms, drive mechanism components, gear components, shafts, rotational components, device housings, doors, support structures, etc.) are optionally formed by various fabrication techniques or combinations of such techniques including, e.g., cast molding, stamping, machining, embossing, extrusion, engraving, injection molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, $3.^{rd}$ Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate device components include, e.g., metal, glass, wood, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In certain embodiments, following fabrication, device components are optionally further processed, e.g., by painting, coating surfaces with a hydrophilic coating, a hydrophobic coating, or the like.

Exemplary rotary units, rotational mechanisms, related applications, and other aspects, which are optionally adapted, e.g., for use with the rotary units and rotational mechanisms described herein are also described in, e.g., U.S. patent application Ser. No. 12/577,326, entitled "ROTARY UNITS, MECHANISMS, AND RELATED DEVICES", filed on Oct. 12, 2009 (now U.S. Pat. No. 8,152,679, issued Apr. 10, 2012), U.S. Provisional Patent Application No. 61/104,748, entitled "ROTARY UNITS, MECHANISMS, AND RELATED DEVICES", filed on Oct. 12, 2008, International Application No. PCT/US2009/060386, entitled "ROTARY UNITS, MECHANISMS, AND RELATED DEVICES", filed on Oct. 12, 2009, U.S. Provisional Patent Application No. 61/365, 290, entitled "ROTARY UNITS, MECHANISMS, AND RELATED DEVICES", filed on Jul. 16, 2010, U.S. patent application Ser. No. 13/184,332, entitled "ROTARY UNITS, MECHANISMS, AND RELATED DEVICES", filed on Jul. 15, 2011, U.S. patent application Ser. No. 13/218,145, entitled "ROTARY UNITS, MECHANISMS, AND RELATED DEVICES", filed on Aug. 25, 2011, U.S. patent application Ser. No. 13/219,683, entitled "ROTARY UNITS, MECHANISMS, AND RELATED DEVICES", filed on Aug. 28, 2011, U.S. patent application Ser. No. 13/221,890, entitled "ROTARY UNITS, MECHANISMS, AND RELATED DEVICES", filed on Aug. 30, 2011, and U.S. patent application Ser. No. 13/423,413, entitled "ROTARY UNITS, MECHANISMS, AND RELATED DEVICES", filed on Mar. 19, 2012, which are each incorporated herein by reference in their entirety for all purposes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A rotary mechanism, comprising:
   at least first, second, and third rotary units that each comprise at least one rotational component, wherein one or more of the rotational components comprise at least a first portion, at least a second portion, and at least one resilient coupling, wherein the resilient coupling resiliently couples the first and second portions to one another, and wherein at least one of the rotational components comprises at least one implement;
   at least first and second counter-rotational mechanisms, wherein the first counter-rotational mechanism operably engages at least the rotational components of the first and second rotary units, and wherein the second counter-rotational mechanism operably engages at least the rotational components of the second and third rotary units; and,
   at least one drive mechanism component or a portion thereof operably engaged with one or more of the rotational components and/or with one or more of the counter-rotational mechanisms, which drive mechanism component or portion thereof is configured at least to effect movement of the rotational components and the counter-rotational mechanisms such that the rotational components of the first and third rotary units rotate in a first direction and the rotational component of the second rotary unit rotates in a second direction.

2. The rotary mechanism of claim 1, comprising more than three rotational components.

3. The rotary mechanism of claim 1, wherein at least one of the rotational components comprises one or more gear components that are configured to operably engage one or more implements rotatably coupled to one or more other rotational components.

4. The rotary mechanism of claim 1, wherein at least a portion of the implement comprises at least one cross-sectional shape selected from the group consisting of: a circle, an oval, a square, a rectangle, a trapezoid, an irregular n-sided polygon, and a regular n-sided polygon.

5. The rotary mechanism of claim 1, wherein the implement is rotatably coupled to the rotational component.

6. The rotary mechanism of claim 1, wherein at least the first counter-rotational mechanism comprises at least a first gear component disposed on the first rotational component, at least a second gear component disposed on the second rotational component, and at least a third gear component that operably engages the first and second gear components such that when the first gear component rotates in the first direction, the second and third gear components rotate in the second direction and when the first gear component rotates in the second direction, the second and third gear components rotate in the first direction.

7. A device comprising the rotary mechanism of claim 1.

8. A vehicle comprising the rotary mechanism of claim 1.

9. The rotary mechanism of claim 1, wherein the resilient coupling comprises at least one positioning mechanism that positions the first and second portions relative to one another within a range of motion.

10. The rotary mechanism of claim 1, wherein the resilient coupling comprises at least one spring mechanism.

11. The rotary mechanism of claim 1, wherein the resilient coupling comprises at least one elastomeric material.

12. The rotary mechanism of claim 1, wherein the resilient coupling comprises at least one material container component.

13. The rotary mechanism of claim 12, wherein the material container component comprises at least one fluidic and/or semi-fluidic material.

14. The rotary mechanism of claim 1, wherein at least the first and second rotary units each comprise:
   at least one rotational component that comprises at least one sun gear component and at least one ring gear component, and
   at least one gear structure that comprises at least one support component and at least one planetary gear component rotatably coupled to the support component, and wherein the planetary gear component is configured to operably engage the ring gear component,
   wherein the sun gear component of at least the first rotary unit operably engages the planetary gear component of at least the second rotary unit such that when the rotational component of the first rotary unit rotates in the first direction, the rotational component of the second rotary unit rotates in the second direction.

15. The rotary mechanism of claim 1, wherein:
   at least the first rotary unit comprises at least one rotational component that comprises at least first and second sun gear components;
   at least the second rotary unit comprises at least one rotational component that comprises at least first and second ring gear components; and,
   at least a first planetary gear component is configured to operably engage the second sun gear component of the first rotary unit and the first ring gear component of the second rotary unit such that when the rotational component of the first rotary unit rotates in the first direction, the rotational component of the second rotary unit rotates in the second direction.

16. The rotary mechanism of claim 1, wherein at least the first and second rotary units each comprises:
   at least one rotational component that comprises at least one ring gear component; and,
   at least one second gear component configured to operably engage the ring gear component.

17. The rotary mechanism of claim 1, wherein:
   at least the rotational components of the first and second rotary units each comprise at least one ring gear component; and,
   at least one of the counter-rotational mechanisms comprises at least a first gear component that operably engages the ring gear component of at least the rotational component of the first rotary unit, at least a second gear component that operably engages the ring gear component of at least the rotational component of the second rotary unit, and at least a third gear component that operably engages at least the second gear component such that when the first gear component rotates in the first direction, the rotational component of the first rotary unit rotates in the first direction and the second gear component and the rotational component of the second rotary unit rotate in the second direction.

18. The rotary mechanism of claim 1, wherein at least the rotational components of the first and second rotary units each comprise at least two ring gear components, and wherein the rotary mechanism comprises at least a first planetary gear component that is configured to operably engage at least one of the ring gear components of the first rotary unit and at least one of the ring gear components of the second rotary unit such that when the rotational component of the first rotary unit rotates in the first direction, the rotational component of the second rotary unit rotates in the second direction.

19. A rotary mechanism, comprising:
   at least first and second rotational components, wherein one or more of the rotational components comprise at least a first portion, at least a second portion, and at least one resilient coupling, wherein the resilient coupling resiliently couples the first and second portions to one another, and wherein at least one of the rotational components comprises at least one implement;
   at least one counter-rotational mechanism that operably engages at least the first and second rotational components; and,
   at least one drive mechanism component or a portion thereof operably engaged with one or more of the rotational components and/or with the counter-rotational mechanism, which drive mechanism component or portion thereof is configured at least to effect rotation of the rotational components such that the first rotational component rotates in a first direction and the second rotational component rotates in a second direction.

20. A method of making a rotary mechanism, the method comprising:
   placing at least one counter-rotational mechanism into operable engagement with at least first and second rotational components, wherein one or more of the rotational components comprise at least a first portion, at least a second portion, and at least one resilient coupling, wherein the resilient coupling resiliently couples the first and second portions to one another, and wherein at least one of the rotational components comprises at least one implement; and,
   placing at least one drive mechanism component or a portion thereof into operable engagement with one or more of the rotational components and/or with the counter-rotational mechanism, which drive mechanism component or portion thereof is configured at least to effect rotation of the rotational components such that the first rotational component rotates in a first direction and the second rotational component rotates in a second direction, thereby making the rotary mechanism.

* * * * *